United States Patent
Gygax et al.

(10) Patent No.: US 9,738,938 B2
(45) Date of Patent: Aug. 22, 2017

(54) **SINGLE NUCLEOTIDE POLYMORPHISMS AND COMMUNITY-ASSOCIATED METHICILLIN-RESISTANT *STAPHYLOCOCCUS AUREUS***

(75) Inventors: Scott E. Gygax, Yardley, PA (US); Sean Chadwick, Florence, NJ (US); Aditya Prasad, Marlton, NJ (US); Martin E. Adelson, East Windsor, NJ (US); Eli Mordechai, Robbinsville, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 265 days.

(21) Appl. No.: 13/068,331

(22) Filed: May 9, 2011

(65) Prior Publication Data

US 2012/0009572 A1 Jan. 12, 2012

Related U.S. Application Data

(60) Provisional application No. 61/395,130, filed on May 7, 2010.

(51) Int. Cl.
*C12Q 1/68* (2006.01)
*C07H 21/04* (2006.01)

(52) U.S. Cl.
CPC ....... *C12Q 1/689* (2013.01); *C12Q 2600/156* (2013.01)

(58) Field of Classification Search
None
See application file for complete search history.

(56) References Cited

FOREIGN PATENT DOCUMENTS

| WO | WO 94/16101 | 7/1994 |
| WO | WO 98/35060 | 8/1998 |
| WO | WO 99/10366 | 3/1999 |

OTHER PUBLICATIONS

None (no art cited by examiner).*
Kramer, Fred Russel, et al., Nature Biotechnology, Mar. 1996, vol. 14, 303-308.
Memmi, Guido, et al., Antimicrobial Agents and Chemotherapy, Nov. 2008, vol. 52, No. 11, 3955-3966.
Wittwer; C.T., et al., Biotechniques, Jan. 1997, vol. 22, No. 1, 176-181.

* cited by examiner

*Primary Examiner* — Diana B Johannsen
(74) *Attorney, Agent, or Firm* — Siu K. Lo; Jessica A. Downing

(57) ABSTRACT

The present invention is based on the discovery of polymorphisms (SNPs) in the penicillin binding protein (pbp3) gene in *Staphylococcus aureus*. The presence of G88A and/or G2047A SNPs provides an accurate, reliable biomarker for the presence of Methicillin Resistant *Staphylococcus aureus* (MRSA), specifically the community-associated MRSA (CA-MRSA). The present invention provides reagents used for detecting the SNPs as well as methods of identifying and using these variants to screen subjects for presence of CA-MRSA. The methods involve isolating a biological sample from a mammal (preferably a human) and testing for the presence of a SNP in the pbp3 gene which is associated with CA-MRSA.

16 Claims, 22 Drawing Sheets

Figure 1    *pbp1* Primer Design

*pbp1*

| OLIGO | start | len | tm | gc% | seq | |
|---|---|---|---|---|---|---|
| LEFT PRIMER #1 | 39 | 20 | 59.21 | 55.00 | AGGGGCAGTCCTACTTGTTG | SEQ ID |
| RIGHT PRIMER #2 | 587 | 20 | 54.44 | 45.00 | GCACCTTTAAGTTCACCAGTATC | SEQ ID |

SEQUENCE SIZE: 2235
PRODUCT SIZE: 549

[START]                                         >>>>>>>>>>>>>>>>>>>>pbp1F
ATGGCGAAGCAAAAAATTAAAATTAAAAAAAATAAAATAGGGGCAGTCCTACTTGTTCGTTTATTCGGAC
TGCTCTTTTTTATATTGGTTTTAAGAATTTCATATATCATGATTACTGGACATTCTAATGGTCAAGATTT
AGTCATGAAGGCAAATGAGAAGTATTTAGTTAAGAATGCACAACAACCAGAACGAGGAAAGATATATGAT
CGTAATGGTAAAGTGCTAGCAGAAGATGTAGAAAGATATAAACTTGTTGCAGTAATAGATAAAAAGGCGA
GTGCCAATTCTAAAAAACCTAGGCATGTAGTTGATAAAAAGAGACTGCAAAGAAATTATCTACAGTCAT
TGATATGAAGCCAGAGGAAATTGAAAAGAGACTTAGTCAAAAGAAAGCCTTCCAAATTGAATTTGGACGC
AAAGGAACAAATTTAACGTATCAGGACAAATTGAAAATAGAGAAAATGAATTTGCCTGGTATTTCTTTAT
TGCCTGAAACAGAACGATTTTATCCAAATGGCAATTTTGCATCACACTTAATTGGTAGAGCTCAGAAAAA
<<<<<<<<<<<<<<<<<<<<<<pbp1R
TCCGGATACTGGTGAACTTAAAGGTGCGCTTGGAGTTGAAAAGATTTTTGATAGTTATTTAAGTGGATCT
AAAGGATCTTTGAGATATATTCATGATATTTGGGGATATATTGCACCAAATACTAAAAAAGAGAAGCAGC
CTAAACGTGGTGATGATGTCCATTTAACAATCGATTCAAATATTCAAGTATTTGTTGAAGAGGCTTTAGA
TGGCATGGTTGAAAGATACCAGCCGAAAGATTTATTTGCGGTTGTCATGGATGCCAAAACTGGAGAAATT
TTAGCATACAGTCAGCGACCAACATTTAATCCTGAAACTGGTAAAGATTTTGGTAAAAAGTGGGCAAATG
ATCTATATCAAAACACATATGAGCCTGGATCAACATTTAAATCATATGGGTTAGCAGCTGCTATTCAAGA
AGGTGCTTTTGATCCTGATAAGAAATATAAATCTGGACATAGAGATATTATGGGTTCACGTATTTCAGAC
TGGAATAGAGTCGGTTGGGGTGAAATCCCAATGTCACTCGGATTTACTTATTCATCTAATACATTGATGA
TGCATTTACAAGATTTAGTTGGTGCAGACAAAATGAAATCTTGGTATGAACGATTTGGATTTGGAAAATC
AACTAAAGGTATGTTTGATGGAGAAGCACCTGGTCAAATTGGATGGAGTAATGAGTTACAACAAAAAACG
TCATCATTTGGTCAATCGACAACTGTAACACCTGTTCAAATGTTACAGGCGCAATCAGCGTTCTTTAATG
ATGGTAATATGTTAAAACCATGGTTTGTGAATAGCGTTGAAAATCCTGTTAGTAAAAGACAATTTTATAA
AGGTCAAAAACAAATCGCAGGCAAACCAATAACAAAAGATACTGCTGAAAAAGTTGAAAAGCAATTGGAT
TTAGTTGTGAATAGTAAGAAGAGTCACGCTGCAAACTATCGTATTGATGGTTATGAGGTCGAAGGTAAGA
CTGGTACAGCACAAGTCGCTGCACCTAATGGTGGTGGATACGTTAAAGGTCCAAACCCATATTTCGTAAG
TTTTATGGGTGACGCACCGAAGAAAAATCCTAAAGTTATTGTATACGCTGGTATGAGCTTGGCACAAAAA
AATGACCAAGAAGCTTATGAATTAGGTGTTAGTAAAGCGTTTAAACCAATAATGGAAAATACTTTGAAAT
ATTTAAATGTAGGTAAATCAAAAGATGACACATCTAATGCAGAGTATAGTAAAGTGCCAGATGTTGAAGG
TCAAGACAAACAAAAAGCTATTGATAATGTGAGTGCAAAATCATTAGAACCAGTTACTATCGGTTCTGGC
ACACAAATAAAAGCGCAATCTATAAAAGCAGGGAATAAAGTCTTACCTCATAGTAAAGTACTGTTATTAA
CAGATGGAGACTTAACTATGCCTGACATGTCAGGATGGACGAAAGAAGATGTCATTGCTTTTGAAAACCT
AACAAATATTAAAGTGAATTTAAAAGGTAGCGGTTTTGTGTCCCACCAATCAATTAGTAAGGGACAAAAA
CTTACTGAAAAAGATAAAATAGACGTAGAATTTTCATCAGAGAATGTAGACAGCAATTCGACGAATAATT
CTGATTCAAATTCAGATGATAAGAAGAAATCTGACAGTAAAACTGACAAAGATAAGTCGGACTAA (SEQ
ID NO. 37)
[STOP]

Figure 2  *pbp2* Primer Design

*pbp2*
```
OLIGO          start  len   tm    gc%    seq
LEFT PRIMER       49   20  59.77  45.00  GGTGGGAAATCCAACTCAAA  SEQ ID #3
RIGHT PRIMER     609   20  57.14  45.00  ACCTGTTACGCCATCAGAAT  SEQ ID #4
SEQUENCE SIZE: 980
PRODUCT SIZE: 561
```

[START]                                              >>>>>>>>>>>>>>>>>>>>pbp2F
ATGACGGAAAACAAAGGATCTTCTCAGCCTAAGAAAAATGGTAATAATGGTGGGAAATCCAACTCAAAAA
AGAATAGAAATGTGAAGAGAACGATTATTAAGATTATTGGCTTCATGATTATTGCATTTTTTGTTGTTCT
TTTACTAGGTATCTTATTGTTTGCTTATTATGCTTGGAAAGCACCTGCTTTTACCGAAGCTAAATTACAA
GATCCGATTCCTGCAAAGATATATGACAAGAACGGAGAACTTGTTAAAACATTAGATAATGGCCAAAGAC
ATGAGCATGTAAATTTAAAAGACGTGCCGAAATCAATGAAAGACGCAGTACTTGCAATTGAAGACAATCG
TTTCTACGAACATGGCGCACTTGATTATAAACGTTTATTCGGTGCAATTGGTAAGAACTTGACTGGTGGA
TTTGGTTCTGAAGGTGCCTCAACATTAACACAACAAGTTGTTAAAGATGCATTTTTATCACAACATAAAT
CTATTGGACGTAAAGCTCAAGAAGCATACTTATCATATCGTTTAGAACAAGAGTATAGTAAAGATGATAT
                   <<<<<<<<<<<<<<<<<<<<pbp2R
CTTCCAAGTATATCTAAATAAAATTTACTATTCTGATGGCGTAACAGGTATTAAAGCTGCTGCTAAGTAT
TACTTTAATAAAGATTTAAAAGATTTAAACTTAGCGGAAGAAGCTTATTTAGCCGGTTTACCTCAGGTTC
CAAACAACTATAATATTTATGATCATCCAAAAGCTGCTGAAGATCGTAAAAACACTGTTTTATACTTAAT
GCATTATCATAAACGCATTACAGATAAACAGTGGGAAGATGCTAAGAAAATCGATTTAAAAGCGAACTTA
GTAAATCGTACTGCTGAAGAACGTCAAAACATTGATACAAATCAAGATTCTGAGTATAATTCATACGTTA
ACTTTGTAAAATCTGAATTAATGAATAATAAAGCATTCAAAGATGAAAATTTAGGTAATGTATTACAAAG
TGGTATTAAAATTTATACAAACATGGATAAAGATGTTCAAAAAACATTACAAAATGATGTTGATAATGGT
AGCTTCTACAAGAATAAAGACCAACAAGTTGGTGCAACGATTCTTGATAGTAAAACTGGTGGTTTAGTTG
CTATATCTGGCGGACGTGATTTCAAAGACGTCGTTAACAGAAACCAAGCAACAGATCCACACCCTACTGG
TTCATCTTTAAAACCTTTCTTAGCGTATGGACCTGCCATTGAAAATATGAAATGGGCAACAAACCATGCG
ATTCAAGATGAATCTTCATATCAAGTTGATGGATCTACATTTAGAAACTATGATACGAAGAGTCACGGTA
CTGTATCTATTTATGATGCTTTACGACAAAGTTTCAATATCCCAGCTTTAAAAGCTTGGCAATCAGTTAA
GCAAAATGCTGGTAATGATGCACCTAAGAAATTCGCTGCCAAACTTGGCTTAAACTACGAAGGCGATATT
GGTCCATCTGAAGTACTTGGTGGTTCTGCTTCAGAATTCTCACCAACACAATTAGCATCAGCATTTGCTG
CAATCGCTAACGGTGGTACTTATAACAACGCGCATTCAATTCAAAAAGTAGTTACTCGTGATGGTGAAAC
AATCGAATACGATCATACTAGCCATAAAGCGATGAGTGATTACACTGCATACATGTTAGCTGAGATGCTA
AAAGGTACATTTAAACCATATGGTTCTGCATATGGCCATGGTGTATCTGGAGTAAATATGGGTGCTAAGA
CAGGTACTGGTACTTACGGTGCTGAAACTTATTCACAATATAATTTACCTGATAATGCAGCGAAAGACGT
GTGGATTAACGGCTTTACACCTCAATACACTATGTCAGTGTGGATGGGCTTCAGTAAAGTTAAACAATAT
GGTGAAAACTCATTTGTGGGACATAGCCAACAAGAATATCCACAGTTCTTATATGAAAATGTGATGTCAA
AAATTTCATCTAGAGATGGCGAAGACTTTAAACGTCCTAGCTCAGTAAGTGGTAGTATCCCATCAATCAA
TGTTTCTGGTAGTCAAGATAACAACACTACAAATCGTAGTACACACGGTGGTAGTGACACATCAGCAAAC
AGCAGTGGTACTGCACAATCAAATAACAATACTAGATCTCAACAATCTTGA (SEQ ID NO. 38)
[STOP]

Figure 3  *pbp3* Primer Design

|  | Start | Length | Tm | GC% | Sequence |
|---|---|---|---|---|---|
| LEFT PRIMER SEQ ID #5 | 25 | 23 | 59.46 | 26.09 | TCAAATGATGAAATCGTTCAAAA |
| RIGHT PRIMER TCCGATTGTGTTGTTTTTCG | 302 | 20 SEQ ID #6 | 59.56 | 40.00 | |

PRODUCT SIZE: 278bp

[START]

>>>>>>>>>>>>>>>>>>>>>>>>>>>>pbp3 F
TTGTTAAAAAGACTAAAAGAAAAATCAAATGATGAAATCGTTCAAAATACAATTAACAAGAG
AATTAACTTTATATTTGGTGTGATTATATTTATTTTTGCAGTACTAGTACTACGTTTAGGTTATT
TACAAATCGCACAAGGCTCACATTATAAACAAATTATAAAAAATGATGAAAACATTACAGTG
AATGAGTCTGTGCCAAGAGGTCGTATTTTAGACAGAAATGGGAAAGTTTTAGTTGATAATGCT
<<<<<<<<<<<<<<<<<<<<<<<<<pbp3 R
TCTAAAATGGCTATTACATATACTAGGGGTCGAAAAACAACACAATCGGAAATGTTGGATAC
GGCTGAAAAGTTATCAAAGCTAATCAAGATGGATACTAAGAAAATTACAGAACGTGATAAGA
AAGATTTCTGGATTCAGTTGCATCCTAAAAAAGCAAAAGCAATGATGACAAAAGAACAAGCT
ATGTTAGCAGATGGAAGTATTAAACAAGATCAATATGATAAACAACTGTTATCGAAAATCGG
AAAATCACAATTAGATGAATTGTCTTCTAAAGATTTACAAGTTTTAGCTATTTTTCGAGAGATG
AATGCAGGAACAGTTTTAGATCCACAAATGATAAAAAATGAAGATGTCAGTGAAAAAGAGTA
TGCAGCAGTTTCTCAGCAACTTTCCAAATTACCAGGTGTTAACACGTCTATGGATTGGGATAG
AAAATATCCATATGGCGATACTTTAAGAGGTATATTCGGAGATGTATCGACACCTGCTGAAGG
TATTCCAAAAGAATTGACAGAACATTACTTATCCAAAGGATATTCACGCAATGATCGTGTTGG
AAAATCTTACCTAGAATATCAATATGAAGATGTATTGCGTGGTAAGAAGAAAGAAATGAAAT
ACACAACGGACAAATCTGGTAAAGTTACATCTTCAGAAGTGTTAAATCCTGGCGCTCGCGGTC
AAGATTTGAAATTAACGATCGATATAGATCTTCAAAAAGAAGTAGAAGCATTATTAGATAAA
CAAATTAAGAAGCTTCGCAGTCAAGGTGCCAAAGATATGGATAATGCAATGATGGTTGTACA
AAATCCTAAAAATGGAGACATTCTTGCGCTTGCCGGAAAGCAGATTAATAAGAGTGGTAAAA
TGACTGATTATGACATTGGTACGTTTACTTCTCAATTTGCGGTTGGATCTTCTGTAAAAGGTGG
AACATTATTAGCCGGTTATCAGAATAAAGCTATCAAAGTTGGAGAAACAATGGTCGATGAAC
CATTACATTTCCAAGGTGGTTTGACAAAACGATCATACTTCAATAAAAACGGGCATGTAACTA
TTAATGATAAGCAAGCTTTGATGCATTCATCAAACGTATATATGTTTAAAACAGCATTAAAAT
TAGCGGGAGACCCTTATTATTCTGGTATGGCTTTACCTTCAGACATAAGTTCACCTGCCCAAA
AGCTAAGAAGAGGATTAAATCAAGTAGGCTTAGGTGTGAAAACAGGGATAGATTTACCAAAT
GAAACAAGAGGTCAAATCGAACCATTAACAAATAATCCAGGTAATTATCTAGATTTATCAATT
GGTCAATATGATACCTATACACCATTACAATTATCACAATATGTTTCAACTATAGCGAATGAT
GGTTATAGAATACAGCCACACATTGGATTAACGATTCATGAATCAACTAATAAAGATGAGGTT
GGTCCACTCAAGAAGAAAATTAATGGCACTGTCTTGAACAAGGTTAATAATACTGAAAAGGA
AATCAAACAAATTCAAGAAGGATTCAAAATGGCATTTAATGATAAAGATGGTACTGGATATG
TTAGTTTTAAAGATACAGTAGTACCTACTGCTGGTAAAACGGGTACCGCAGAAGTGTTCCAAA
ACGGAGAGCCAAGAGTTAACTCTACTTATATAGGATACGCGCCAATTGATGATCCAAAATTAG
CGTTTTCAATTGTATATACAAATCAGCCTGTACCACCACCATGGTTAACAGGTGGAGACTTAG
GTAGAGATGTAATTAACTACTACTTTAAGCAGTTAGGTAAAAATGATAAAAATAAAGACAAA
GACAAATAA (SEQ ID NO. 39)

[STOP]

Figure 4   *pbp4* Primer Design

*pbp4*

| OLIGO | start | len | tm | gc% | seq | | |
|---|---|---|---|---|---|---|---|
| LEFT PRIMER | 50 | 20 | 53.25 | 35.00 | TTATGACACCATATGCACAA | SEQ ID | #7 |
| RIGHT PRIMER | 635 | 20 | 51.91 | 40.00 | TCTAAAATGGCGTAGTCTCT | SEQ ID | #8 |

SEQUENCE SIZE: 1296
PRODUCT SIZE: 586

[START]
```
                                            >>>>>>>>>>>>>>>>>>>>pbp4F
ATGAAAAATTTAATATCTATTATCATCATTTTATGTTTAACATTAAGTATTATGACACCATATGCACAAG
CTGCTAACAGTGACGTAACCCCTGTACAAGCAGCAAATCAATATGGTTATGCAGGTTTGTCGGCTGCATA
CGAACCGACGAGTGCTGTTAATGTTAGTCAAACTGGACAATTACTGTATCAATACAATATCGATACTAAG
TGGAATCCAGCGTCTATGACTAAATTAATGACAATGTACTTAACATTGGAAGCTGTAAATAAGGGGCAGC
TTTCACTTGATGACACAGTCACAATGACGAACAAAGAATATATTATGTCTACACTACCTGAGTTGAGTAA
TACGAAACTATATCCTGGACAAGTATGGACAATCGCAGACCTATTACAAATTACAGTATCTAATTCTAGT
AATGCCGCGGCATTAATTTTAGCTAAGAAGGTATCAAAAAACACCAGCGATTTCGTTGATTTAATGAATA
ACAAAGCTAAAGCTATCGGAATGAAAAATACACATTTCGTCAATCCAACGGGTGCTGAAAATTCAAGATT
                                                         <<<<<<<<<<<<<<<
ACGTACATTTGCACCAACAAAATATAAAGACCAAGAACGTACTGTAACGACTGCTAGAGACTACGCCATT
<<<<<pbp4R
TTAGATTTACACGTGATTAAAGAGACACCTAAAATATTAGACTTTACAAAGCAGTTAGCACCAACAACGC
ATGCAGTTACGTATTACACATTCAACTTTTCATTGGAAGGTGCAAAAATGAGTTTGCCTGGTACAGATGG
TTTAAAAACTGGATCAAGTGATACAGCAAATTACAACCATACGATTACTACTAAACGAGGTAAATTTAGA
ATTAATCAAGTTATCATGGGTGCAGGAGACTATAAAAACCTTGGTGGCGAGAAGCAACGTAATATGATGG
GGAATGCATTAATGGAACGTTCATTTGATCAGTATAAATATGTAAAAATATTGCCTAAAGGTGAGCAAAG
GATAAATGGTAAGAAATATTATGTTGAAAATGATCTTTACGATGTTTTACCAAGTGATTTTAGTAAAAAA
GATTATAAACTTGTAGTCGAAGATGGTAAAGTACACGCGGACTATCCAAGAGAATTTATTAATAAAGATT
ATGGACCTCCAACTGTAGAAGTTCATCAGCCAATTATCCAAAAGGCAAATACTGTTGCTAAAAGTATGTG
GGAAGAACATCCATTATTCACTATCATTGGTGGTGCATGCCTAGTCGCTGGATTAGCACTAATTGTTCAT
ATGATAATCAATCGTTTATTTAGAAAAAGAAAATAA (SEQ ID NO. 40)
```
[STOP]

Figure 5      Alignment of MSSA, CA-MRSA, and HA-MRSA *pbp1*

```
              10                  20                  30                  40
  1   T G C T C T T T T T T A T A T T G G T T T T A A G A A T T T C A T A T A T C A T   001_PBP1-C.ab1
  1   T G C T C T T T T T T A T A T T G G T T T T A A G A A T T T C A T A T A T C A T   004_PBP1-H.ab1
  1   T G C T C T T T T T T A T A T T G G T T T T A A G A A T T T C A T A T A T C A T   003_PBP1-S.ab1

50                  60                  70                  80
 41   G A T T A C T G G A C A T T C T A A T G G T C A A G A T T T A G T C A T G A A G   001_PBP1-C.ab1
 41   G A T T A C T G G A C A T T C T A A T G G T C A A G A T T T A G T C A T G A A G   004_PBP1-H.ab1
 41   G A T T A C T G G A C A T T C T A A T G G T C A A G A T T T A G T C A T G A A G   003_PBP1-S.ab1

90                 100                 110                 120
 81   G C A A A T G A [A] A A G T A T T T A G T T A A G A A T G C A C A A C A A C C A G   001_PBP1-C.ab1
 81   G C A A A T G A [A] A A G T A T T T A G T T A A G A A T G C A C A A C A A C C A G   004_PBP1-H.ab1
 81   G C A A A T G A G A A G T A T T T A G T T A A G A A T G C A C A A C A A C C A G   003_PBP1-S.ab1

130                 140                 150                 160
121   A A C G A G G A A A G A T A T A T G A T C G T A A T G G T A A A G T G C T A G C   001_PBP1-C.ab1
121   A A C G A G G A A A G A T A T A T G A T C G T A A T G G T A A A G T G C T A G C   004_PBP1-H.ab1
121   A A C G A G G A A A G A T A T A T G A T C G T A A T G G T A A A G T G C T A G C   003_PBP1-S.ab1

170                 180                 190                 200
161   A G A A G A T G T A G A A A G A T A T A A A C T T G T T G C A G T A A T A G A T   001_PBP1-C.ab1
161   A G A A G A T G T A G A A A G A T A T A A A C T T G T T G C A G T A A T A G A T   004_PBP1-H.ab1
161   A G A A G A T G T A G A A A G A T A T A A A C T T G T T G C A G T A A T A G A T   003_PBP1-S.ab1

210                 220                 230                 240
201   A A A A G G C G A G T G C C A A T T C T A A A A A C C T A G G C A T G T A G   001_PBP1-C.ab1
201   A A A A G G C G A G T G C C A A T T C T A A A A A C C T A G G C A T G T A G   004_PBP1-H.ab1
201   A A A A G G C G A G T G C C A A T T C T A A A A A C C T A G G C A T G T A G   003_PBP1-S.ab1

250                 260                 270                 280
241   T T G A T A A A A A G A G A C T G C A A A G A A A T T A T C T A C A G T C A T   001_PBP1-C.ab1
241   T T G A T A A A A A G A G A C T G C A A A G A A A T T A T C T A C A G T C A T   004_PBP1-H.ab1
241   T T G A T A A A A A G A G A C T G C A A A G A A A T T A T C T A C A G T C A T   003_PBP1-S.ab1

290                 300                 310                 320
281   T [A] A T A T G A A G C C A G A G G A A A T T G A A A G A G A C T T A G T C A A   001_PBP1-C.ab1
281   T [A] A T A T G A A G C C A G A G G A A A T T G A A A A G A G A C T T A G T C A A   004_PBP1-H.ab1
281   T G A T A T G A A G C C A G A G G A A A T T G A A A A G A G A C T T A G T C A A   003_PBP1-S.ab1

330                 340                 350                 360
321   A A G A A A G C [T] T T C C A A A T T G A A T T T G G A C G C A A A G G A A C A A   001_PBP1-C.ab1
321   A A G A A A G C [T] T T C C A A A T T G A A T T T G G A C G C A A A G G A A C A A   004_PBP1-H.ab1
321   A A G A A A G C C T T C C A A A T T G A A T T T G G A C G C A A A G G A A C A A   003_PBP1-S.ab1

370                 380                 390                 400
361   A T T A A C G T A T C A G G A C A A A T T G A A A A T A G A A A A T G A A   001_PBP1-C.ab1
361   A T T A A C G T A T C A G G A C A A A T T G A A A A T A G A A A A T G A A   004_PBP1-H.ab1
361   A T T A A C G T A T C A G G A C A A A T T G A A A A T A G A A A A T G A A   003_PBP1-S.ab1

410                 420                 430                 440
401   T T T G C C T G G T A T T T C T T T A T T G C C T G A A A C A G A A C G [C] T T T   001_PBP1-C.ab1
401   T T T G C C T G G T A T T T C T T T A T T G C C T G A A A C A G A A C G [C] T T T   004_PBP1-H.ab1
401   T T T G C C T G G T A T T T C T T T A T T G C C T G A A A C A G A A C G A T T T   003_PBP1-S.ab1

450                 460                 470                 480
441   T A T C C A A A T G G C A A T T T T G C A T C A C A C T T A A T T G G T A G A G   001_PBP1-C.ab1
441   T A T C C A A A T G G C A A T T T T G C A T C A C A C T T A A T T G G T A G A G   004_PBP1-H.ab1
441   T A T C C A A A T G G C A A T T T T G C A T C A C A C T T A A T T G G T A G A G   003_PBP1-S.ab1

490                 500
481   C T C A G A A A A A T C C G G A T A C T       SEQ ID NO: 41 - 001_PBP1-C.ab1
481   C T C A G A A A A A T C C G G A T A C T       SEQ ID NO: 42 - 004_PBP1-H.ab1
481   C T C A G A A A A A T C C G G A T A C T       SEQ ID NO: 43 - 003_PBP1-S.ab1
```

Decoration 'Decoration #1': Box residues that differ from 003_PBP1-S.ab1.

**Figure 6  Alignment of MSSA, CA-MRSA, and HA-MRSA *pbp2***

Figure 7 Alignment of MSSA, CA-MRSA, and HA-MRSA *pbp3*

Figure 8  Alignment of MSSA, CA-MRSA, and HA-MRSA *pbp4*

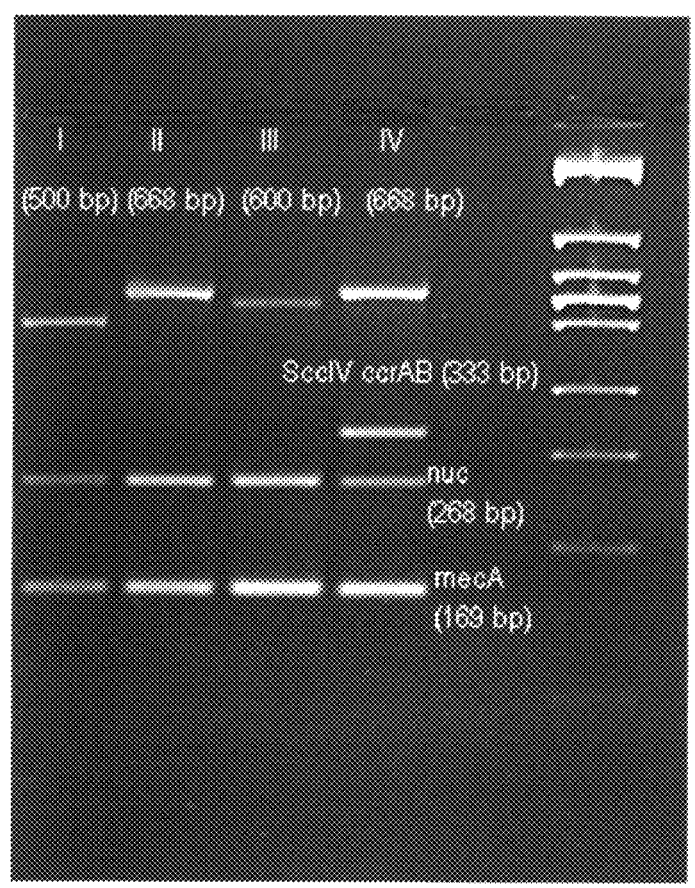
Figure 9    MRSA SCC Mec Typing Assay

Figure 10    Results of *pbp3* Sequencing in Hospital-Associated MRSA

```
               76         88                                   119
Laboratory
sccMec(I)      TTTGGTGTGATT TATTTATTTTTGCAGTACTAGTACTACGTTT
               (SEQ ID NO: 53)
sccMec(II)     TTTGGTGTGATT TATTTATTTTTGCAGTACTAGTACTACGTTT
               (SEQ ID NO: 54)
sccMec(III)    TTTGGTGTGATT TATTTATTTTTGCAGTACTAGTACTACGTTT
               (SEQ ID NO: 55)
43300          TTTGGTGTGATT TATTTATTTTTGCAGTACTAGTACTACGTTT
               (SEQ ID NO: 56)

Clinical
5565(I)        TTTGGTGTGATT TATTTATTTTTGCAGTACTAGTACTACGTTT
               (SEQ ID NO: 57)
7085(IV)       GTTGCTGTGATT ATTTATTTTTGCTGCTCTCGA-ACTACGTTT
               (SEQ ID NO: 58)
```

Figure 11    Results of *pbp3* Sequencing in Community-Associated MRSA

```
                76            88                              119
Laboratory
USA300      TTTGGTGTGATTATATTTATTTTTGCAGTACTAGTACTACGTTT
            (Bases 76-119 of SEQ ID NO: 39)
Clinical
1646        TTTGGTGTGATTATATTTATTTTTGCAGTACTAGTACTACGTTT (SEQ ID NO:59)
5427        TTTGGTGTGATTATATTTATTTTTGCAGTACTAGTACTACGTTT (SEQ ID NO:60)
5624        TTTGGTGTGATTATATTTATTTTTGCAGTACTAGTACTACGTTT (SEQ ID NO:61)
4091        TTTGGTGTGATTATATTTATTTTTGCAGTACTAGTACTACGTTT (SEQ ID NO:62)
5974        TTTGGTGTGATTATATTTATTTTTGCAGTACTAGTACTACGTTT (SEQ ID NO:63)
6634        TTTGGTGTGATTATATTTATTTTTGCAGTACTAGTACTACGTTT (SEQ ID NO:64)
6729        TTTGGTGTGATTATATTTATTTTTGCAGTACTAGTACTACGTTT (SEQ ID NO:65)
8038        TTTGGTGTGATTATATTTATTTTTGCAGTACTAGTACTACGTTT (SEQ ID NO:66)
8050        TTTGGTGTGATTATATTAATTTTTGCAGTACTAGTACTACGTTT (SEQ ID NO:67)
8741        TTTGGTGTGATTATATTTATTTTTGCAGTACTAGTACTACGTTT (SEQ ID NO:68)
1728        TTTGGTGTGATTATATTTATTTTTGCAGTACTAGTACTACGTTT (SEQ ID NO:69)
8931        TTTGGTGTGATTATATTTATTTTTGCAGTACTAGTACTACGTTT (SEQ ID NO:70)
7419        TTTGGTGTGATTATATTTATTTTTGCAGTACTAGTACTACGTTT (SEQ ID NO:71)
2464        TTTGGTGTGATTATATTTATTTTTGCAGTACTAGTACTACGTTT (SEQ ID NO:72)
1549        TTTGGTGTGATTATATTTATTTTTGCAGTACTAGTACTACGTTT (SEQ ID NO:73)
3481        TTTGGTGTGATTATATTTATTTTTGCAGTACTAGTACTACGTTT (SEQ ID NO:74)
3715        TTTGGTGTGATTATATTTATTTTTGCAGTACTAGTACTACGTTT (SEQ ID NO:75)
1586        TTTGGTGTGATTATATTTATTTTTGCAGTACTAGTACTACGTTT (SEQ ID NO:76)
2368        TTTGGTGTGATTATATTTATTTTTGCAGTACTAGTACTACGTTT (SEQ ID NO:77)
4303        TTTGGTGTGATTATATTTATTTTTGCAGTACTAGTACTACGTTT (SEQ ID NO:78)
7526        TTTGGTGTGATTATATTTATTTTTGCAGTACTAGTACTACGTTT (SEQ ID NO:79)
8568        TTTGGTGTGATTATATTTATTTTTGCAGTACTAGTACTACGTTT (SEQ ID NO:80)
5929        TTTGGTGTGATTATATTTATTTTTGCAGTACTAGTACTACGTTT (SEQ ID NO:81)
0291        TTTGGTGTGATTATATTTATTTTTGCAGTACTAGTACTACGTTT (SEQ ID NO:82)
5470        TTTGGTGTGATTATATTTATTTTTGCAGTACTAGTACTACGTTT (SEQ ID NO:83)
6050        TTTGGTGTGATTATATTTATTTTTGCTGTACTAGTACTACGTTT (SEQ ID NO:84)
3849        -TTGGTGAGATAATATTTATTTTTGCAGTACTAGTACTACGTTT (SEQ ID NO:85)
6388        TTTGGTGTGATTATATTTATTTTTGCAGC-CTAGTACTACGTTT (SEQ ID NO:86)
7384        TTTGGTGTGATTATATTTATTTTTGCAGTACTAGTACTACGTTT (SEQ ID NO:87)
8098        TTTGGTGAGATTATATTTATTTTTGCAGTACTAGTACTACGTTT (SEQ ID NO:88)
1138        TTTGGTGTGATTATATTTATTTTTGCAGTACTAGTACTACGTTT (SEQ ID NO:89)
4813        TTTGGTGTGATTATATTTATTTTTGCAGTACTAGTACTACGTTT (SEQ ID NO:90)
4746        TTTGGTGTGATTATATTTATTTTTGCAGTACTAGTACTACGTTT (SEQ ID NO:91)
8555        TTTGGTGTGATTATATTTATTTTTGCAGTACTAGTACTACGTTT (SEQ ID NO:92)
2973        TTTGGTGTGATTATATTTATTTTTGCAGTACTAGTACTACGTTT (SEQ ID NO:93)
4852        GTTGCTGTGATAATATTTATTTTTGCTGTACGTCGAACTACGTT (SEQ ID NO:94)
0966        TTTGGTGTGATTATATTTATTTTTGCAGTACTAGTACTACGTTT (SEQ ID NO:95)
4163        TTTGGTGTGATTATATTTATTTTTGCAGTACTAGTACTACGTTT (SEQ ID NO:96)
7783        TTTGGTGTGATTATATTTATTTTTGCAGTACTAGTACTACGTTT (SEQ ID NO:97)
```

Figure 12   Results of *pbp3* Sequencing in Methicillin-Susceptible *S. aureus*

```
              76          88                                    119
Laboratory
MSSA 25293   TTTGGTGTGATTGTATTTATTTTTGCAGTACTAGTACTACGTTT (SEQ ID NO:98)
MSSA 29213   TTTGGTGTGATTGTATTTATTTTTGCAGTACTAGTACTACGTTT (SEQ ID NO:99)
Clinical
MSSA 6072    TTTGGTGTGATTGTATTTATTTTTGCAGTACTAGTACTACGTTT (SEQ ID NO:100)
MSSA 8358    TTTGGTGTGATTGTATTTATTTTTGCAGTACTAGTACTACGTTT (SEQ ID NO:101)
MSSA 8284    TTTGGTGTGATTGCCGTATCTTTTGCAGTTCTAGTACTACGTTT (SEQ ID NO:102)
MSSA 8228    TTTGGTGTGATTGTATTTATTTTTGCAGTACTAGTACTACGTTT (SEQ ID NO:103)
MSSA 8305    --------GATTGTATTCTTTTAGTAGCTGAGATGACAAACACT (SEQ ID NO:104)
MSSA 2037    TTTGGTGTGATTGTAAAAATTTTGCAGTTGTAGTACTACGTTTA (SEQ ID NO:105)
```

Figure 13     Results of *pbp3* Sequencing in Rare *S. aureus* Cases

*SCC Mec IV, PVL -*

Clinical
7085     GTTGCTGTGATT▓ATTTATTTTTGCTGCTCTCGA-ACTACGTTT
(SEQ ID NO: 58)

*PVL +, non-SCC Mec IV*

Laboratory
MSSA 25293     TTTGGTGTGATT▓TATTTATTTTTGCAGTACTAGTACTACGTTT
(SEQ ID NO: 98)

*SCC Mec IV, PVL + (representative)*

Clinical
USA300     TTGGTGTGATT▓TATTTATTTTTGCAGTACTAGTACTACGTTT
(Bases 77-119 of SEQ ID NO: 39)

Laboratory
1646     TTTGGTGTGATT▓TATTTATTTTTGCAGTACTAGTACTACGTTT
(SEQ ID NO: 59)
5427     TTTGGTGTGATT▓TATTTATTTTTGCAGTACTAGTACTACGTTT
(SEQ ID NO: 60)
5624     TTTGGTGTGATT▓TATTTATTTTTGCAGTACTAGTACTACGTTT
(SEQ ID NO: 61)
4091     TTTGGTGTGATT▓TATTTATTTTTGCAGTACTAGTACTACGTTT
(SEQ ID NO: 62)

Figure 14  Alignment of HA-MRSA, CA-MRSA, and MSSA Amino Acid Sequences

V30I

HA-MRSA Strain (COL) – (Amino Acids 0-58 of SEQ ID NO: 106)
0                              30                                                    58
MLKRLKEKSNDEIVQNTINKRINFIFGVIVFIFAVLVLRLGYLQIAQGSHYKQIIKND CA-MRSA Strain (USA300) – (Amino Acids 0-58 of SEQ ID NO: 107)
MLKRLKEKSNDEIVQNTINKRINFIFGVIFIFAVLVLRLGYLQIAQGSHYKQIIKND MSSA Strain (MSSA476) – (Amino Acids 0-58 of SEQ ID NO: 108)
MLKRLKEKSNDEIVQNTINKRINFIFGVIVFIFAVLVLRLGYLQIAQGSHYKQIIKND

D683N

HA-MRSA Strain (COL) – (Amino Acids 659-691of SEQ ID NO: 106)
                                683         691
PWLTGGDLGRDVINYYFKQLGKDDKNKDKDK CA-MRSA Strain (USA300) – (Amino Acids 659-691of SEQ ID NO: 107)
PWLTGGDLGRDVINYYFKQLGKNDKNKDKDK MSSA Strain (MSSA476) – (Amino Acids 659-691of SEQ ID NO: 108)
PWLTGGDLGRDVINYYFKQLGKDDKNKDKDK

Figure 15  Alignment of HA-MRSA, CA-MRSA, and MSSA Nucleotide Sequences

G88A

HA-MRSA Strain (COL) – (Bases 61-118 of SEQ ID NO: 109)
61                                88                                              118
AGAATTAACTTTATATTTGGTGTGATTGTATTTATTTTTGCAGTACTAGTACTACGTT CA-MRSA Strain (USA300) – (Bases 61-118 of SEQ ID NO: 39)
AGAATTAACTTTATATTTGGTGTGATTATATTTATTTTTGCAGTACTAGTACTACGTT MSSA Strain (MSSA476) – (Bases 61-118 of SEQ ID NO: 110)
AGAATTAACTTTATATTTGGTGTGATTGTATTTATTTTTGCAGTACTAGTACTACGTT

G2047A

HA-MRSA Strain (COL) – (Bases 2041-2076 of SEQ ID NO: 109)
        2047                                     2076
GGTAAAGATGATAAAAATAAAGACAAAGACAAATAA CA-MRSA Strain (USA300) –(Bases 2041-2076 of SEQ ID NO: 39)
GGTAAAAATGATAAAAATAAAGACAAAGACAAATAA MSSA Strain (MSSA476) -  (Bases 2041-2076 of SEQ ID NO: 110)
GGTAAAGATGATAAAAATAAAGACAAAGACAAATAA Figure 16   Alignment of Position 88 in *S. aureus pbp3* Using Available GenBank Sequences

*NCBI GenBank Nucleotide Sequences*

Hospital-Associated MRSA

```
                  76            88                               119
COL(I)        TTTGGTGTGATTGTATTTATTTTTGCAGTACTAGTACTACGTTT
              (Bases 76-119 of SEQ ID NO: 109)
N315(II)      TTTGGTGTGATTGTATTTATTTTTGCAGTACTAGTACTACGTTT
              (SEQ ID NO: 111)
Mu50(II)      TTTGGTGTGATTGTATTTATTTTTGCAGTACTAGTACTACGTTT
              (SEQ ID NO: 112)
MRSA252(II)   TTTGGTGTGATTGTATTTATTTTTGCAGTACTAGTACTACGTTT
              (SEQ ID NO: 113)
JH1(II)       TTTGGTGTGATTGTATTTATTTTTGCAGTACTAGTACTACGTTT
              (SEQ ID NO: 114)
JH9(II)       TTTGGTGTGATTGTATTTATTTTTGCAGTACTAGTACTACGTTT
              (SEQ ID NO: 115)
Mu3           TTTGGTGTGATTGTATTTATTTTTGCAGTACTAGTACTACGTTT
              (SEQ ID NO: 116)
```

Community-Associated MRSA

```
USA300 37     TTTGGTGTGATTATATTTATTTTTGCAGTACTAGTACTACGTTT
              (Bases 76-119 of SEQ ID NO: 39)
USA300 15     TTTGGTGTGATTATATTTATTTTTGCAGTACTAGTACTACGTTT
              (Bases 76-119 of SEQ ID NO: 117)
MW2           TTTGGTGTGATTGTATTTATTTTTGCAGTACTAGTACTACGTTT
              (SEQ ID NO: 118)
```

Methicillin-Susceptible *S. aureus*

```
MSSA476       TTTGGTGTGATTGTATTTATTTTTGCAGTACTAGTACTACGTTT
              (SEQ ID NO: 110)
NCTC8325      TTTGGTGTGATTGTATTTATTTTTGCAGTACTAGTACTACGTTT
              (SEQ ID NO: 119)
RF122         TTTGGTGTGATTGTATTTATTTTTGCAGTACTAGTACTACGTTT
              (SEQ ID NO: 120)
Newman        TTTGGTGTGATTGTATTTATTTTTGCAGTACTAGTACTACGTTT
              (SEQ ID NO: 121)
```

Figure 17   Alignment of Position 2047 in *S. aureus pbp3* Using Available GenBank Sequences

Hospital-Associated MRSA

```
                2041      2047                                        2076
COL         GGTAAA█ATGATAAAAATAAAGACAAAGACAAATAA
            (Bases 2041-2076 of SEQ ID NO: 109)
N315        GGTAAA█ATGATAAAAATAAAGACAAAGACAAATAA
            (SEQ ID NO: 122)
Mu50        GGTAAA█ATGATAAAAATAAAGACAAAGACAAATAA
            (SEQ ID NO: 123)
MRSA252     GGTAAA█ACGATAAAAATAAAGACAAAGACAAATAA
            (SEQ ID NO: 124)
JH1         GGTAAA█ATGATAAAAATAAAGACAAAGACAAATAA
            (SEQ ID NO: 125)
JH9         GGTAAA█ATGATAAAAATAAAGACAAAGACAAATAA
            (SEQ ID NO: 126)
Mu3         GGTAAA█ATGATAAAAATAAAGACAAAGACAAATAA
            (SEQ ID NO: 127)
```

Community-Associated MRSA

```
USA300-37   GGTAAA█ATGATAAAAATAAAGACAAAGACAAATAA
            (Bases 2041-2076 of SEQ ID NO: 39)
USA300-15   GGTAAA█ATGATAAAAATAAAGACAAAGACAAATAA
            (Bases 2041-2076 of SEQ ID NO: 117)
MW2         GGTAAA█ATGATAAAAATAAAGACAAAGACAAATAA
            (SEQ ID NO: 128)
```

**Methicillin-Susceptible *S. aureus***

```
MSSA476     GGTAAA█ATGATAAAAATAAAGACAAAGACAAATAA
            (SEQ ID NO: 110)
NCTC8325    GGTAAA█ATGATAAAAATAAAGACAAAGACAAATAA
            (SEQ ID NO: 129)
RF122       GGTAAA█ATGATAAAAATAAAGACAAAGACAAATAA
            (SEQ ID NO: 130)
Newman      GGTAAA█ATGATAAAAATAAAGACAAAGACAAATAA
            (SEQ ID NO: 131)
```

Figure 18 Altered Length *pbp3* Primer Design

```
              Start  Length  Tm     GC%    Sequence
LEFT PRIMER   25     19      51.70  31.58  TCAAATGATGAAATCGTTC   SEQ ID #21
RIGHT PRIMER  301    18      52.15  38.89  CCGATTGTGTTGTTTTC     SEQ ID #22
```

PRODUCT SIZE: 277

[START]

>>>>>>>>>>>>>>>>>>>> pbp3F length

1 TTGTTAAAAGACTAAAAGAAAAATCAAATGATGAAATCGTTCAAAATACAATTAACAAG

G88A

61 AGAATTAACTTTATATTTGGTGTGATTATATTTATTTTTGCAGTACTAGTACTACGTTTA

121 GGTTATTTACAAATCGCACAAGGCTCACATTATAAACAAATTATAAAAAATGATGAAAAC

181 ATTACAGTGAATGAGTCTGTGCCAAGAGGTCGTATTTTAGACAGAAATGGGAAAGTTTTA pbp3R length<<<<<<<<<<<<<<<<<<<<

241 GTTGATAATGCTTCTAAAATGGCTATTACATATACTAGGGGTCGAAAAACAACACAATCG<

301 GAAATGTTGGATACGGCTGAAAAGTTATCAAAGCTAATCAAGATGGATACTAAGAAAATT

361 ACAGAACGTGATAAGAAAGATTTCTGGATTCAGTTGCATCCTAAAAAAGCAAAAGCAATG

421 ATGACAAAAGAACAAGCTATGTTAGCAGATGGAAGTATTAAACAAGATCAATATGATAAA (Bases 1-480 of SEQ ID NO: 39)

**Figure 19 Altered Placement Within *pbp3* Primer Design**

|              | Start | Length | Tm    | GC%   | Sequence              |           |
|--------------|-------|--------|-------|-------|-----------------------|-----------|
| LEFT PRIMER  | 19    | 22     | 56.33 | 27.27 | GAAAAATCAAATGATGAAATCG | SEQ ID #23 |
| RIGHT PRIMER | 261   | 21     | 49.63 | 28.57 | CATTTTAGAAGCATTATCAAC  | SEQ ID #24 |

PRODUCT SIZE: 243

|START|

```
                        >>>>>>>>>>>>>>>>>>>>>>> pbp3F place
  1 TTGTTAAAAGACTAAAAGAAAAATCAAATGATGAAATCGTTCAAAATACAATTAACAAG
                                   G88A
 61 AGAATTAACTTTATATTTGGTGTGATTATATTTATTTTTGCAGTACTAGTACTACGTTTA

121 GGTTATTTACAAATCGCACAAGGCTCACATTATAAACAAATTATAAAAAATGATGAAAAC

181 ATTACAGTGAATGAGTCTGTGCCAAGAGGTCGTATTTTAGACAGAAATGGGAAAGTTTTA
       <<<<<<<<<<<<<<<<<<<<<<<  pbp3R place
241 GTTGATAATGCTTCTAAAATGGCTATTACATATACTAGGGGTCGAAAAACAACACAATCG 301 GAAATGTTGGATACGGCTGAAAAGTTATCAAAGCTAATCAAGATGGATACTAAGAAAATT
```
(Bases 1-360 of SEQ ID NO: 39)

Figure 20    Allele Specific PCR Primer Design

```
>Staphylococcus epidermidis RP62A (SEQ ID NO: 132), complete genome Length=2616530
 Features in this part of subject sequence: penicillin-binding protein 3
 Identities = 1587/2037 (77%), Gaps = 8/2037 (0%)

(s. aur consists of Bases 1-660 of SEQ ID NO:39)
S.aur      1        TTGTTAAAAAGACTAAAAGAAAAATCAAATGATGAAATCGTTCAAAATACAATTAACAAG      60
                    ||| ||||||||| |||||||||||||||||||||||||  |   ||| || || || ||
S.epi 1157871       TTGCTAAAAAGATTAAAAGAAAAATCAAATGATGAAAAATGAGAAACACCATGAATAAA   1157812
                                       CaMRSA-For
Query      61       AGAATTAACTTTATATTTGGTGTGATTATATTTATTTTGCAGTACTAGTACTACGTTTA     120
                    ||||| || || |||||||| | || ||||||| ||||| || | ||| | ||
Sbjct   1157811     AGAATCAATTTCATATTTGGATTTATAGTATTTATCTTGCTATAGTCGTATTGAGATTA   1157752
Query      121      GGTTATTTACAAATCGCACAAGGCTCACATTATAAACAAATTATAAAAAATGATGAAAC     180
                    |||||||||||||| |||||||| || ||||| |||||| | |||||| ||||||||||
Sbjct   1157751     GGTTATTTACAAATAGCACAAGGATCTCATTACAAACAATTAATCAAAAACGATGAAAC   1157692

Query      181      ATTACAGTGAATGAGTCTGTGCCAAGAGGTCGTATTTTAGACAGAAATGGGAAAGTTTTA    240
                    || || || |||||  || || |||||||| ||||  |||| ||||||| ||||| ||
Sbjct   1157691     ATAACTGTTAATGAATCAGTACCAAGAGGCCGAATACTAGATAGAAATGGCAAAGTACTA   1157632
                                                           CaMRSA-Rev-1 (231bp)
Query      241      GTTGATAATGCTTCTAAAATGGCTATTACATATACTAGGGGTCGAAAAACAACACAATCG    300
                    |||||||||||||| ||  ||| ||||||||||||| ||||   || |||||| ||||| |
Sbjct   1157631     GTTGATAATGCTTCAAAGATGTCTATTACATACACTAGAAACCGTAAAACATCACAAAAG   1157572
                                     CaMRSA-Rev-2 (260bp)
Query      301      GAAATGTTGGATACGGCTGAAAAGTTATCAAAGCTAATCAAGATGGATACTAAGAAAATT    360
                    ||||||||  ||||  ||| | || | || |    |||| || ||||||||  | |||||
Sbjct   1157571     GAAATGTTAAATACTGCTAAGAAACTGACAGATTAATTAAAATGGATACAGATAAAATT   1157512

Query      361      ACAGAACGTGATAAGAAAGATTTCTGGATTCAGTTGCATCCTAAAAAAGCAAAGCAATG    420
                    || ||  |  ||||| || ||||| |||||| ||  ||||    |   || |||  |
Sbjct   1157511     ACTGAGAGAGATAAAAAGGATTTTTGGATTCAAATGTATCCGTCATCTGCTAAAAAGTTA   1157452
                                                 CaMRSA-Rev-3 (385bp)
Query      421      ATGACAAAAGAACAAGCTATGTTAGCAGATGGAAGTATTAAACAAGATCAATATGATAAA    480
                    ||||  ||| |||||| ||||||  ||||||||  ||||| |||| ||||| || ||||
Sbjct   1157451     ATGAGAAAAGAACAATTAATGTTAGAGGATGGCAGTATTTCACAAGACCAATTTGATACC   1157392
                                      CaMRSA-Rev-4 (438bp)
Query      481      CAACTGTTATCGAAAATCGGAAAATCACAATTAGATGAATTGTCTTCTAAAGATTTACAA    540
                    |||||    | |||||  |||||    ||||   ||| |||  |  ||| |||||||| ||
Sbjct   1157391     CAACTTAGAGATAAAATAGGAAAAAAACAATTAAAACAGTTAACTAAAAAGATTTGCAA   1157332

Query      541      GTTTTAGCTATTTTTCGAGAGATGAATGCAGGAACAGTTTTAGATCCACAAATGATAAAA    600
                    ||||||||| || |||  ||||| ||| |||| ||  ||||||||| ||| || || ||
Sbjct   1157331     GTTTTAGCAATTTATCGGGAAATGAACGCTGGGTCAACTCTAGATCCTCAAACAATTAAA   1157272

Query      601      AATGAAGATGTCAGTGAAAAAGAGTATGCAGCAGTTTCTCAGCAACTTTCCAAATTACCA    660
                    |||||||| || || ||  || ||||||||||| || || || || ||||| |||||||
Sbjct   1157271     AATGAAGACGTAAGCGAGAAAGAATATGCAGCCGTATCACAACAGCTTTCTAAATTACCT   1157212
```

Figure 21    Allele-Specific PCR to Detect G88A SNP in CA-MRSA

*CA-MRSA primers*

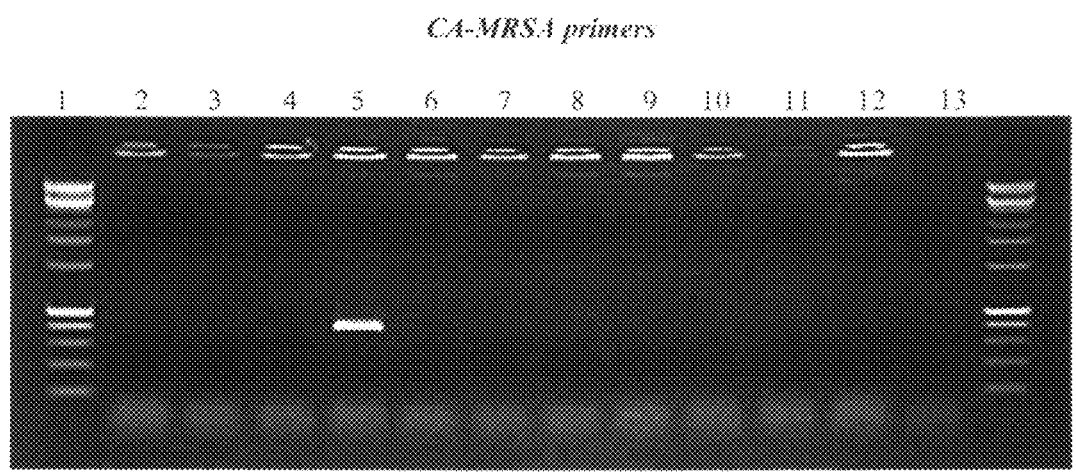

Key:
1. Ladder (100/200/300/400/500/1000bp)    1% agarose gel
2. HA-MRSA sccMec type I
3. HA-MRSA sccMec type II
4. HA-MRSA sccMec type III
5. CA-MRSA sccMec type IV PVL+
6. *Streptococcus agalactiae* A909
7. *Streptococcus agalactiae* NEM316
8. *Streptococcus agalactiae* O90R
9. Methicillin-Susceptible *S. aureus* ATCC 29213
10. *Streptococcus pyogenes*
11. *E. coli*
12. *Staphylococcus epidermidis*
13. Blank (1x TE buffer)

Figure 22  Allele-Specific PCR to Detect G88 Allele in HA-MRSA and MSSA

*HA-MRSA+MSSA primers*

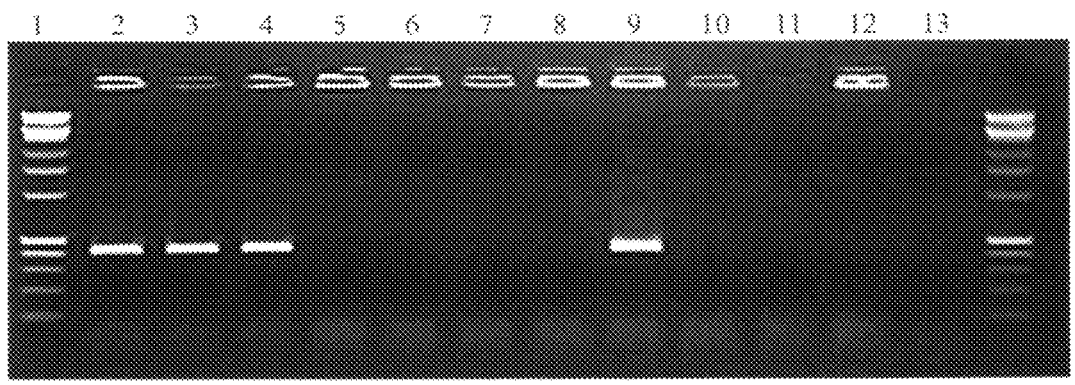

Key:
1. Ladder (100/200/300/400/500/1000bp)    1% agarose gel
2. HA-MRSA sccMec type I
3. HA-MRSA sccMec type II
4. HA-MRSA sccMec type III
5. CA-MRSA sccMec type IV PVL+
6. *Streptococcus agalactiae* A909
7. *Streptococcus agalactiae* NEM316
8. *Streptococcus agalactiae* O90R
9. Methicillin-Susceptible *S. aureus* ATCC 29213
10. *Streptococcus pyogenes*
11. *E. coli*
12. *Staphylococcus epidermidis*
13. Blank (1 x TE buffer)

SINGLE NUCLEOTIDE POLYMORPHISMS AND COMMUNITY-ASSOCIATED METHICILLIN-RESISTANT *STAPHYLOCOCCUS AUREUS*

CROSS-REFERENCE TO RELATED APPLICATION

This application claims the benefit under 35 U.S.C. §119 (e) to U.S. Provisional Application No. 61/395,130 filed May 7, 2010, the content of which is incorporated by reference herein in its entirety.

FIELD OF THE INVENTION

The present invention generally relates to the field of diagnosis of infection with a gram-positive bacterium in a mammal. The present invention specifically provides previously unrecognized single nucleotide polymorphisms (SNPs) present in the *Staphylococcus aureus* genome identified as being involved in bacteriology associated with a human disease. The disclosed naturally-occurring polymorphisms are valuable for association analysis. Specifically, the identified SNPs present in penicillin binding protein 3 (pbp3) are useful for such applications as screening for the presence of methicillin-resistant *Staphylococcus aureus* (MRSA), particularly community-associated MRSA (CA-MRSA). The SNPs provided herein are useful for diagnostic detection in human CA-MRSA infection. Methods and reagents for detecting the presence of these polymorphisms are provided.

BACKGROUND OF THE INVENTION

Since the first report of a clinical strain in England in 1961, methicillin-resistant *Staphylococcus aureus* (MRSA) has become one of the principal pathogenic bacteria of nosocomial infection. It poses a major healthcare concern due to the high morbidity and mortality in patients associated with hospital and community acquired infections. MRSA bacterium is a variant of *Staphylococcus aureus* that has acquired drug resistance to β-lactam antibiotics such as methicillin, oxacillin, and ampicillin by the integration of a transposon known as Staphylococcal Cassette Chromosome (SCC). Antibiotic resistance is reported to be associated with the acquisition of penicillin-binding protein 2a (PBP2a) by *Staphylococcus aureus*. PBP2a purportedly has a lower affinity to β-lactam antibiotics. In 2009, Contreras-Martel et al. described single nucleotide polymorphisms (SNPs) in a *Streptococcus pneumoniae* penicillin binding protein (pbp) gene ultimately leading to decreased susceptibility to beta-lactam antibiotics. This is different from what is normally seen in *Staphylococcus aureus*, in which PBP2a is an alternate penicillin binding protein acquired form the environment that exhibits lower beta-lactam binding affinity.

There are four (4) predominant SCC types of MRSA; namely, type I, type II, type III and type IV MRSA. Types I-III are hospital-associated MRSA (HA-MRSA) and type IV is community-associated MRSA (CA-MRSA). CA-MRSA is associated with the Panton-Valentine leukocidin (PVL) toxin and represents a highly virulent type of MRSA. Risk of *Staphylococcus aureus* infection is high for patients who have opened wounds or weakened immune systems staying in hospitals and nursing homes, as well as for other healthcare facilities. Once an individual is infected with MRSA, the choice of effective antibiotics is limited. These include alternate antibiotics (e.g., vancomycin and teicoplanin and linezolid). Therefore, accurate MRSA identification and SCC typing of the microorganism is crucial and there is a continuing need for an accurate and speedy identification of MRSA. Early detection of various types of MRSA constitutes an important determinant for the treatment of MRSA-infected patients.

Current methodology in detecting and typing MRSA predominantly involves use of molecular PCR technology. In 1986, Matsuhashi et al. cloned the mecA gene that encodes an alternative penicillin binding protein, pbp2a. The mecA gene is known to exist on SCC of MRSA and coagulase-negative *Staphylococci* (MRC-NS), but not on methicillin-susceptible *Staphylococcus aureus* (MSSA). The mecA gene is therefore considered a gene adventitiously acquired in the genomes of *Staphylococcus aureus*. Detection of the mecA gene in the genomic DNA of *Staphylococcus aureus* generally is achieved by PCR (polymerase chain reaction) or hybridization, which makes it possible to identify it as either MRSA or MRC-NS. However, identification of MRSA using this mecA detection method suffers from the following problems. First, direct detection of the mecA gene from a sample, even if successful, cannot be taken as a proof of the existence of MRSA. Second, this method requires culturing of the bacterial strain from a patient's sample and confirmation of *Staphylococcus aureus* by a conventional strain identification method. These conventional strain identification methods require a minimum of 48-72 hours to provide a positive MRSA identification. Doctors often are reluctant to provide an empiric therapy until an infectious strain is identified.

Single nucleotide polymorphism (SNP) is a common form of genetic polymorphism. SNPs may influence gene functions and modify a microorganism's ability to manifest a disease process. Although it is generally understood that a disease often has a genetic component in its etiology and may be unraveled in genetic association studies, to date and to the best of the present inventors' knowledge, there are no reported genetic markers (e.g., SNPs) that are associated with methicillin-resistant *Staphylococcus aureus* (MRSA), let alone one of the most virulent MRSA (i.e., community-associated MRSA).

Accordingly, there is a need for a genetic marker to predict the presence of CA-MRSA. The need for such a reliable SNP biomarker for CA-MRSA is believed to have utility in the bacteriology application in the detection of MRSA. The present inventors cured all the prior art deficiency and discovered specific SNPs that are useful in predicting the presence of CA-MRSA.

BRIEF SUMMARY OF THE INVENTION

The present invention is based on the discovery of particular SNPs in a penicillin-binding protein gene (specifically, penicillin binding protein 3 gene) that represent biomarker candidates for CA-MRSA. In accordance with the present invention, the presence of two (2) SNPs in MRSA represents a good marker for the presence of CA-MRSA. There is disclosed herein methods of detecting these two SNPs.

In one aspect, the present invention provides a two (2) novel SNPs that predict the presence of CA-MRSA and methods of using these SNPs in assessing the presence (or colonization) of CA-MRSA.

In one aspect, the present invention provides the identification of these two (2) novel SNPs that are useful to predict the presence of CA-MRSA in a biological sample from a subject suspected of infection or colonization of CA-MRSA.

In one aspect, the present invention provides a method of detecting the presence of community associated methicillin-resistant *Staphylococcus aureus* (CA-MRSA) in a human, comprising the steps of a) obtaining a biological sample from a human suspected of a CA-MRSA infection; b) isolating genomic material from said biological sample; and c) detecting the presence of a SNP selected from the group consisting of G88A and G2047A present in a penicillin binding protein 3 gene, wherein the presence of said SNP is indicative of the presence of CA-MRSA in said biological sample and infection with CA-MRSA in said human. Preferably, the SNP is G88A, and the SNP causes an amino acid change of V30I. Preferably, the SNP is G2047A, the SNP causes an amino acid change of D683N.

In one aspect, the present invention provides a method of detecting the presence of community associated methicillin-resistant *Staphylococcus aureus* (CA-MRSA) in a human using a biological sample such as whole blood, plasma, urine and exudate from an infected site.

In one aspect, the present method involves an isolating step that is performed using guanindinium hydrochloride or Qiagen. Preferably, the detecting step is performed by polymerase chain reaction (PCR). Preferably, the detecting step is performed by real-time PCR, allele-specific PCR or pyrosequencing.

In one aspect, the present invention provides a kit for detecting the presence of community-associated methicillin-resistant *Staphylococcus aureus* (CA-MRSA) in a human, comprising: (a) a primer pair comprising a forward primer and a reverse primer for amplifying a region containing a SNP selected from the group consisting of G88A and G2047A of the penicillin binding protein 3 gene to produce an amplicon; (b) a sequencing primer for initiating a sequencing reaction for said amplicon; and (c) an instruction of using said primer pair and said sequencing primer in a PCR followed by sequencing reaction to determine the presence of said SNP, wherein the presence of said SNP is indicative of the presence of CA-MRSA. Preferably, said primer pair is producing an amplicon containing said G88A SNP. Preferably, said forward primer is SEQ ID No. 5, said reverse primer is SEQ ID No. 6, and said sequencing primer is SEQ ID No. 5.

In one aspect, the present invention provides a kit for detecting the presence of community-associated methicillin-resistant *Staphylococcus aureus* (CA-MRSA) in a human, comprising: (a) an allele-specific primer pair comprising a forward primer and a reverse primer for amplifying a region containing a SNP selected from the group consisting of G88A and G2047A of the penicillin binding protein 3 gene to produce an amplicon; and (b) an instruction of using said allele-specific primer pair in a PCR to determine the presence of said SNP, wherein the presence of said SNP is indicative of the presence of CA-MRSA. Preferably, said primer pair comprising a forward primer of SEQ ID No. 26 and a reverse primer of SEQ ID No. 36.

BRIEF DESCRIPTION OF THE DRAWINGS

FIG. 1 depicts the designed primer set (forward and reverse primers) used to amplify the N-terminus of the pbp1 gene of *Staphylococcus aureus* for sequencing. Primers were designed with similar $T_M$ values between 45-60° C., a length of 15-35 bases, and a <1 kb amplicon for ease of sequencing.

FIG. 2 depicts the designed primer set (forward and reverse primers) used to amplify the N-terminus of the pbp2 gene of *Staphylococcus aureus* for sequencing. Primers were designed with similar $T_M$ values between 45-60° C., a length of 17-24 bases, and a <1 kb amplicon for ease of sequencing.

FIG. 3 depicts the designed primer set (forward and reverse primers) used to amplify the N-terminus of the pbp3 gene of *Staphylococcus aureus* for sequencing. Primers were designed with similar $T_M$ values between 45-60° C., a length of 17-24 bases, and a <1 kb amplicon for ease of sequencing.

FIG. 4 depicts the designed primer set (forward and reverse primers) used to amplify the N-terminus of the pbp4 gene of *Staphylococcus aureus* for sequencing. Primers were designed with similar $T_M$ values between 45-60° C., a length of 17-24 bases, and a <1 kb amplicon for ease of sequencing.

FIG. 5 depicts the alignment of the N-terminus of the pbp1 gene from nucleotide 71-570 in CA-MRSA, HA-MRSA, and MSSA laboratory strains. The alignment was done by the Megalign program from Lasergene. Differences in sequence from the susceptible MSSA "baseline" are boxed.

FIG. 6 depicts the alignment of the N-terminus of the pbp2 gene from nucleotide 117-562 in CA-MRSA, HA-MRSA, and MSSA laboratory strains. The alignment was done by the Megalign program from Lasergene. Differences in sequence from the susceptible MSSA "baseline" are boxed.

FIG. 7 depicts the alignment of the N-terminus of the pbp3 gene from nucleotide 66-296 in CA-MRSA, HA-MRSA, and MSSA laboratory strains. The alignment was done by the Megalign program from Lasergene. Differences in sequence from the susceptible MSSA "baseline" are boxed.

FIG. 8 depicts the alignment of the N-terminus of the pbp4 gene from nucleotide 91-590 in CA-MRSA, HA-MRSA, and MSSA laboratory strains. The alignment was done by the Megalign program from Lasergene. Differences in sequence from the susceptible MSSA "baseline" are boxed.

FIG. 9 depicts multiplex PCR used to distinguish HA-MRSA (SCC Mec I, II, and III), CA-MRSA (SCC Mec IV), and MSSA. mecA is a MRSA-specific gene, nuc is a *Staphylococcus aureus* specific gene, ccrAB is SCC Mec IV specific, and SCC Mec bands are MRSA type-specific.

FIG. 10 depicts a portion of sequences (bp 76-119) derived from the pbp3 gene of HA-MRSA strains. The sequences shown exhibit high homology to each other upon alignment, and are highly conserved within HA-MRSA isolates. sccMec (I), sccMec(II), sccMec(III), and 43300, are HA-MRSA representative strains from the ATCC. 5565 and 7085 are clinical HA-MRSA isolates. Nucleotide 88 in the gene is highlighted for future reference as a SNP site, and a guanine is present at that location.

FIG. 11 depicts a portion of sequences (bp 76-119) derived from the pbp3 gene of CA-MRSA strains. The sequences shown exhibit high homology to each other upon alignment, and are highly conserved within CA-MRSA isolates. USA300 is a CA-MRSA representative strain from the ATCC. All remaining strains were isolated from clinical biological samples. The SNP site at nucleotide 88 in the gene is highlighted and an adenine is present at that location. This differs from HA-MRSA (FIG. 10), which has a guanine at that site.

FIG. 12 depicts a portion of sequences (bp 76-119) derived from the pbp3 gene of MSSA strains. The sequences shown exhibit high homology to each other upon alignment, and are highly conserved within MSSA isolates. MSSA25293 and MSSA29213 are MSSA representative strains from the ATCC. All remaining strains were isolated from clinical biological samples. The SNP site at nucleotide 88 in the gene is highlighted and a guanine is present at that location. This is similar to HA-MRSA (FIG. 10), and differs from CA-MRSA (FIG. 11).

FIG. 13 depicts a portion of sequences (bp 76-119) derived from the pbp3 gene of *Staphylococcus aureus* strains. The figure shows that the G88A seen in CA-MRSA is only observed when SCC Mec type IV and PVL are both present. Representative strains (USA 300, 1646, 5427, 5624 and 4091) of CA-MRSA all had G88A, while a SCC Mec IV and PVL-negative strain (7085) possessed a G88 and a MSSA PVL-positive strain (25293) also had a G88.

FIG. 14 depicts an alignment of pbp3 amino acid sequences from representative HA-MRSA, CA-MRSA, and MSSA strains (COL, USA300, and MSSA476, respectively) that are available publicly through the National Center for Biotechnology Information. The alignment revealed 2 amino acid changes, V30I and D683N, due to SNPs.

FIG. 15 depicts an alignment of pbp3 nucleotide sequences from representative HA-MRSA, CA-MRSA, and MSSA strains (COL, USA300, and MSSA476, respectively) that are available publicly. The alignment revealed the two SNPs responsible for the two amino acid changes seen in FIG. 14. The SNPs observed were G88A and G2047A.

FIG. 16 depicts a nucleotide alignment of all publicly available *Staphylococcus aureus* pbp3 sequences, separated into HA-MRSA, CA-MRSA, and MSSA categories. All but one isolate fit the pattern seen in clinical samples (FIGS. 10-12), in which HA-MRSA and MSSA have a guanine at nucleotide 88, and CA-MRSA has a G88A single nucleotide polymorphism. Only one CA-MRSA isolate, MW2, has a guanine at position 88.

FIG. 17 depicts a nucleotide alignment of all publicly available *Staphylococcus aureus* pbp3 sequences, separated into HA-MRSA, CA-MRSA, and MSSA categories. All but one isolate fit the pattern proposed in FIG. 15, in which HA-MRSA and MSSA have a guanine at nucleotide 2047, and CA-MRSA has a G2047A single nucleotide polymorphism. Only one CA-MRSA isolate, MW2, has a guanine at nucleotide 2047.

FIG. 18 depicts the new pbp3 amplification primer set (forward and reverse primers) with different oligonucleotide lengths to show that pbp3 can be amplified with a number of different primers in order to sequence the SNP described. The new primers were designed to flank the G88A SNP.

FIG. 19 depicts the new pbp3 amplification primer set (forward and reverse primers) with different locations along the pbp3 gene to show that pbp3 can be amplified with a number of different primers in order to sequence the SNP described. The new primers were designed to flank the G88A SNP.

FIG. 20 depicts the generation of primers for allele-specific PCR detection of G88 and A88 alleles in the *S. aureus* pbp3 gene. *Staphylococcus epidermidis* pbp3 was aligned to *S. aureus* pbp3 so that primers could be designed to *Staphylococcus aureus*-specific regions. Four reverse primers were designed to species-specific regions of the gene. Forward primers were created with either the "A" or "G" representing the final nucleotide of the oligonucleotide, with varying penultimate bases to determine which created the greater dynamic instability in order to only amplify in the presence of the desired allele.

FIG. 21 depicts the results of an allele-specific PCR to detect the G88A SNP in CA-MRSA. Only the CA-MRSA DNA was able to amplify with the allele-specific primers. HA-MRSA, MSSA, *E. coli*, GBS, GAS, *Staphylococcus epidermidis*, and a 1XTE buffer negative control all failed to amplify.

FIG. 22 depicts the results of an allele-specific PCR to detect the G88 allele in HA-MRSA and MSSA. Only the HA-MRSA and MSSA DNA was able to amplify with these allele-specific primers. CA-MRSA, *E. coli*, GBS, GAS, *Staphylococcus epidermidis*, and a 1XTE buffer negative control all failed to amplify.

DETAILED DESCRIPTION OF THE INVENTION

Definitions:

Various terms used throughout this specification shall have the definitions set forth herein.

As used herein, the term "MRSA" refers to *Staphylococcus aureus* that is resistant to methicillin (i.e., *Staphylococcus aureus* that does not respond to treatment with β-lactam antibiotics, e.g., methicillin). MRSA contains the SCCmec transposon. MRSA can be subtyped into type I, type II, type III, type IV or type IV. "Type I MRSA" refers to MRSA that contains SCCmec type I and is positive for nuc gene and mecA gene. "Type II MRSA" refers to MRSA that contains SCCmec type II and is positive for nuc gene and mecA gene. "Type III MRSA" refers to MRSA that contains SCCmec type III, and is positive for nuc gene and mecA gene. "Type IV MRSA" refers to MRSA that contains SCCmec type III and is positive for ccrAB gene, nuc gene and mecA gene.

The term "HA-MRSA" refers to hospital-associated MRSA and contains SCCmec type I, II and III.

The term "CA-MRSA" refers to community-associated MRSA. CA-MRSA infections occur in the community and are associated with infections that originate outside the healthcare system (i.e., non-nosocomial infections).

The term "SCCmec DNA" refers to *Staphylococcus* Cassette Chromosome that contains the mecA, mecR, mecI and ccrAB genes.

The term "mecA" refers to the methicillin resistant gene that encodes the low affinity penicillin binding protein 2 (PBP2a) and it renders the β-lactam resistance to the *Staphylococcus aureus*.

The term "ccrAB" refers to the gene that encodes transposase/integrase and allows SCC to be a Mobile Genetic Element.

The term "nuc" refers to the *Staphylococcus aureus* specific gene.

As used herein, "a" or "an" may mean one or more.

The term "multiplex polymerase chain reaction" or "multiplex PCR" is a PCR reaction that consists of multiple primer sets within a single PCR mixture to produce amplicons of varying sizes that are specific to different DNA sequences. By targeting multiple genes at once, additional information may be gained from a single test run that otherwise would require several times the reagents and more time to perform.

The term "OneSwab®" refers to a unique, non-invasive, highly stable specimen collection and transport platform proprietary to Medical Diagnostic Laboratories, LLC. OneSwab® platform consists of polyester fiber swab, liquid transport medium and polyethylene transport vial.

The term "genomic material" refers to DNA, RNA or mRNA molecules isolated from a biological sample.

The term "polymorphism" refers to the occurrence of two or more alternative genomic sequences or alleles between or among different genomes or individuals.

The term "single nucleotide polymorphism" ("SNP") refers to a site of one nucleotide that varies between alleles.

The term "oligonucleotide" is used interchangeably with "primer" or "polynucleotide."

The term "primer" refers to an oligonucleotide used to direct an activity to a region of nucleic acid. With PCR, a primer or pair of primers defines the area of the genome to be amplified. A primer is usually about 15 to about 35 nucleotides in length and hybridizes to a region complementary to the target sequence.

The term "probe" refers to an oligonucleotide that hybridizes to a target nucleic acid in a PCR reaction. Target sequence refers to a region of nucleic acid that is to be analyzed and comprises the polymorphic site of interest.

The term "biological sample" is used in a broad sense. Exemplary "biological sample" includes, but are not limited to, fluid sample (e.g., blood, plasma, urine, exudate from an infected area) or tissue samples such as cervix tissue (e.g., cervicovaginal swab), rectal swab and the like. Biological sample used herein derives from a mammal, such as a human.

The term "penicillin binding protein" or "pbp" refers to a group of bacterial proteins that are characterized by their affinity for and binding of β-lactam antibiotics (e.g., penicillin).

The present inventors discovered two (2) novel single nucleotide polymorphisms (SNPs) in *Staphylococcus aureus* as putative molecular biomarkers useful in predicting the presence of community-associated methicillin-resistant *Staphylococcus aureus* (CA-MRSA). To the best of the present inventors' knowledge, there has been no association reported regarding any SNP association with CA-MRSA. Specifically, the present invention provides detection of two (2) SNP on the penicillin binding protein gene 3 and association with CA-MRSA. This discovery provides the first report that provides a novel diagnostic test for detection of CA-MRSA.

The present invention provides compositions and methods for detecting a single nucleotide polymorphism (SNP) associated with the presence of CA-MRSA.

In one embodiment, the present invention provides methods for detecting a single nucleotide polymorphism (SNP) associated with the presence of CA-MRSA in a mammal. Preferably, the mammal is a human.

The present methods comprise detecting a nucleic acid sequence comprising position 88 of a nucleic acid encoding penicillin binding protein 3 (i.e., G88A), wherein the presence of a G to A substitution at the position 88 of the nucleic acid encoding pbp3 gene indicates that the human subject carries the presence of CA-MRSA.

The present methods also comprise detecting a nucleic acid sequence comprising position 2047 of the nucleic acid encoding penicillin binding protein 3 (i.e., G2047A), wherein the presence of a G to A substitution at the position of the nucleic acid encoding pbp3 gene indicates that the human subject carries the presence of CA-MRSA. Based on the G to A substitution in these positions, the G88A SNP pbp3 causes an amino acid change of V30I on the PBP3 protein. The G2047A SNP pbp3 causes an amino acid change of D683N on the PBP3 protein.

In one embodiment, the nucleic acid is detected by (a) specifically amplifying a nucleic acid sequence comprising position 88 of a polynucleotide encoding pbp3 gene, thereby amplifying nucleic acids comprising the SNP associated with CA-MRSA; and (b) detecting the amplified nucleic acids, thereby detecting the SNP associated with CA-MRSA.

In one embodiment, the nucleic acid is detected by (a) specifically amplifying a nucleic acid sequence comprising position 2047 of a polynucleotide encoding pbp3 gene, thereby amplifying nucleic acids comprising the SNP associated with CA-MRSA; and (b) detecting the amplified nucleic acids, thereby detecting the SNP associated with CA-MRSA.

Notably, the nucleic acid sequence of the pbp3 gene may vary slightly among different strains. However, the present inventors discovered that at the positions 88 and 2047, the nucleotides remain constant (i.e., G88 and G2047 in HA-MRSA and MSSA and A88 and A2047 in CA-MRSA). The polymorphisms of G88A and/or G2047A in the CA-MRSA classification do not vary among different strains.

In one embodiment, the nucleic acid of the pbp3 gene comprises the sequence set forth in SEQ ID NO: 39 (i.e., Accession No. NC_010079.1; Gene ID 5777252). In another embodiment, the nucleic acid of the pbp3 gene comprises the sequence set forth in Accession No. NC_007793.1; Gene ID 3915175). In yet another embodiment, the nucleic acid of the pbp3 gene comprises the sequence set forth in Accession No. NC_003923.1; Gene ID 1003616).

In some embodiments, the nucleic acid sequence is specifically amplified using primers comprising the sequences set forth in SEQ ID NOs: 5 and 6. In some embodiments, the SNP is detected by sequencing the amplified nucleic acids.

In another embodiment, the present invention provides a kit for detecting a SNP associated with CA-MRSA comprising: (a) an isolated polynucleotide comprising position 88 of a polynucleotide encoding PBP3 protein; (b) primers that specifically amplify the nucleic acid; and (c) an instruction for performing a PCR reaction to detect said SNP (i.e., G88A). The presence of said G88A as indicative of the presence of CA-MRSA.

Preferably, the isolated polynucleotide has a nucleic acid sequence comprising SEQ ID NO. 39. Preferably, the primers comprise the nucleotide sequences set forth in SEQ ID NOs. 5, 6, 26 and 36. Preferably, the primers comprise the nucleotide sequences set forth in SEQ ID NOs. 26 and 36.

In another embodiment, the present invention provides a kit for detecting a SNP associated with CA-MRSA comprising: (a) an isolated polynucleotide comprising position 2047 of a polynucleotide encoding PBP3 protein; (b) primers that specifically amplify the nucleic acid; and (c) an instruction for performing a PCR reaction to detect said SNP (i.e., G2047A). The presence of said G2047A as indicative of the presence of CA-MRSA. Preferably, the kit further comprises information or protocols for performing the amplification procedure that detects the presence of G88A and/or G2047A.

Kits can include, for example, amplification reagents comprising primers sufficient to amplify at least one pbp3 SNP (e.g., G88A and/or G2047A) and at least one probe for amplifying and detecting the polynucleotide sequence. In one embodiment, the present kits further comprise a DNA polymerase and appropriate buffers, salts and other reagents to facilitate amplification reactions.

Our finding is both unexpected and surprising. While there are reports that an alternative protein (i.e., PBP2a) (encoded by mecA) that is situated in a genomic island designated as SCCmec) and has a reduced affinity to β-lactam antibiotics, there has been, however, no report linking penicillin binding protein 3. A recent study also hints to another protein (i.e., PBP4 protein) in CA-MRSA strains MW2 and USA300 that these authors stated that it may play a role in β-lactam resistance (See, Memmi, G. et al., *Antimicrobial Agents and Chemotherapy*, Nov. 2008, Vol. 52, No. 11, pp. 3955-3966). The loss of PBP4 is proposed to severely affect the transcription of PBP2.

In one embodiment, the present invention provides detection of G88A SNP on pbp3, the presence of such SNP as indicative of an infection of CA-MRSA (i.e., presence of CA-MRSA in a patient).

In another embodiment, the present invention provides detection of G2047A SNP on pbp3, the presence of such SNP as indicative of an infection of CA-MRSA (i.e., presence of CA-MRSA in a patient).

In yet another embodiment, the present invention provides detection of both G88A and G2047A SNPs on pbp3, the presence of such SNPs as indicative of an infection of CA-MRSA (i.e., presence of CA-MRSA in a patient). Because the association of G88A and G2047A with CA-MRSA is high, the presence of either G88A or G2047A is a sufficient indicator of an infection of CA-MRSA.

SCC Mec Typing Assay

In one embodiment, the present invention provides a method of typing *Staphylococcus aureus* (i.e., classifying the *Staphylococcus aureus* bacteria into either (i) MSSA or (ii) MRSA). This method has been fully described in our pending application Ser. No. 12/930,663 (entitled "Method of Determining Types I, II, III, IV or V or Methicillin-Resistant *Staphylococcus aureus* (MRSA) in a Biological Sample"), the content of which is incorporated herein by reference in its entirety.

In this SCC Mec typing assay, we used a multiplex PCR assay. Multiplex PCR allows an investigator to assay two or more different gene targets in a single reaction through the use of multiple probes or primers, each specific for its own target and each comprising a fluorescent moiety that emits at a unique wavelength. Multiplexing is possible with TaqMan® probes, Molecular Beacons, and Scorpions, as recognized by one skilled in the art. Due to its non-specific binding nature, SYBR® Green may not be amenable to multiplexing.

In accordance with the multiplex PCR assay for SCC Mec typing, we used a first primer pair that is specific for SCCmec types I, II and IV, thus permitting the generation of two (2) amplicons with a similar size of about 668 bp (i.e., revealing SCCmec type II or IV), and one (1) amplicon with a size of 566 bp (i.e., revealing SCCmec type I). In the assay, we also used a second primer pair that is specific for SCCmec type III, permitting the generation of one amplicon with a size of 622 bp (i.e., revealing SCCmec type III). We used a third primer pair that is specific type IV, permitting the generation of one amplicon with a size of 334 bp (i.e., revealing the ccrAB gene specific to SCCmec type IV). The different molecular sizes of the amplicons can be conveniently determined and analyzed in a gel, thus allowing the easy identification for types I, II, III or IV MRSA. Notably, the forward primers are selected in the 5'UTR region and they can be the same for the first, second and third primer pairs. A unique property of the forward primer (because of its location within the 5'UTR) conveniently provides specificity of *Staphylococcus* (i.e., *Staphylococcus*-specificity).

Detection of SNP (i.e., G88A SNP and/or G2047A SNP)

The present invention is directed to the discovery of two (2) novel SNPs present on penicillin-binding protein 3 gene (i.e., pbp3)—they are G88A and G2047A. Both of these SNPs are shown to be associated with the presence of CA-MRSA. Methods of detection of SNP are known in the art. Exemplary methods are provided herein to illustrate the detection of either G88A and/or G2047A.

According to one aspect of the present invention, detection of the present novel SNPs (i.e., G88A or G2047A) may be performed by a real-time PCR. Real-time PCR may be performed using exonuclease primers (TaqMan® probes) using a biological sample obtained from a human suspected of a MRSA infection.

In one embodiment, the primers utilize the 5' exonuclease activity of thermostable polymerases such as Taq to cleave dual-labeled probes present in the amplification reaction (See, e.g., Wittwer, C. et al., *Biotechniques* 22:130-138, 1997). While complementary to the PCR product, the primer probes used in this assay are distinct from the PCR primer and are dually-labeled with both a molecule capable of fluorescence and a molecule capable of quenching fluorescence. When the probes are intact, intramolecular quenching of the fluorescent signal within the DNA probe leads to little signal. When the fluorescent molecule is liberated by the exonuclease activity of Taq during amplification, the quenching is greatly reduced leading to increased fluorescent signal. Non-limiting example fluorescent probes include 6-carboxy-floruescein moiety and the like. Exemplary quenchers include Black Hole Quencher 1 moiety and the like.

In another embodiment, real-time PCR methods may include the use of molecular beacon technology. The molecular beacon technology utilizes hairpin-shaped molecules with an internally-quenched fluorophore whose fluorescence is restored by binding to a DNA target of interest (See, e.g., Kramer, R. et al. *Nat. Biotechnol.* 14:303-308, 1996).

In another embodiment, real-time PCR methods may also include the use of one or more hybridization probes, which may also be determined by those skilled in the art, in view of this disclosure. Exemplary probes such as the HEX channel and/or FAM channel probes, as understood by one skilled in the art.

According to another aspect of the present invention, allele-specific PCR may be performed to detect the presently discovered SNPs (i.e., G88A and/or G2047A) in a biological sample. The allele-specific PCR method operates on the basis of the specific amplification of a target allele by the PCR with primers designed such that their 3' ends are placed at the mutation site (i.e., the 3'-most nucleotide of the primer corresponds to the mutated nucleotide in the target/template nucleic acid). When this base is complementary to that of the corresponding nucleotide of the specific allele, the target is amplified; when it is not complementary PCR will proceed with a significant delay. The longer the delay, the more efficiently the system can discriminate between alleles.

In one embodiment, the present invention provides oligonucleotides that are useful for allele-specific PCR. Such oligonucleotides comprise a specificity enhancing group that improves discrimination between alleles.

The ability to discriminate between alleles by allele-specific PCR may be improved by using DNA polymerases modified to be substantially unable to extend an oligonucleotide when the 3'-most nucleotide of the oligonucleotide is not base paired with the target nucleic acid sequence. The preparation of such modified DNA polymerases is disclosed in WO 99/10366 and WO 98/35060, the contents of which are incorporated herein by reference. These publications disclose the cloning and mutagenesis of thermostable polymerases, in particular, the thermostable DNA polymerase isolated from *Thermatoga* spp.

In one embodiment, an allele-specific primer may be designed based on only one mismatch (based on the polymorphic site) of one of the alleles. The preparation of such allele-specific primers is well-known in the art and within the capacity of the molecular PCR field.

In another embodiment, an allele-specific primer is designed with a penultimate nucleotide mismatch. Often this second approach may enhance the specificity of the reaction. For example, in the scenario of G88A, an allele-specific primer was prepared such that the primer had a penultimate nucleotide sequence of AA, CA or GA (See, Table 13). Without the penultimate nucleotide mismatch, the allele-specific primer was TA (See, Table 13). It is apparent from this study that using a penultimate nucleotide mismatch may be preferable because of its enhanced specificity (See, Table 13).

An exemplary allele-specific PCR primers useful in detection of G88A SNP (associated with CA-MRSA) includes a forward primer (i.e., SEQ ID NO. 26), and a reverse primer (i.e., SEQ ID NO. 36). For control allele-specific PCR primers useful in the detection of MSSA, and HA-MRSA, an exemplary allele-specific PCR primers includes a forward primer (i.e., SEQ ID NO. 30), and a reverse primer (i.e., SEQ ID NO. 36).

According to another aspect of the present invention, sequencing may be performed to detect SNPs in a biological sample. A variety of automated sequencing procedures can be utilized ((1995) *Biotechniques* 19:448), including sequencing by mass spectrometry (see, e.g., PCT International Publication No. WO94/16101; Cohen et al., *Adv. Chromatogr.* 36:127-162 (1996); and Griffin et al., *Appl. Biochem. Biotechnol.* 38:147-159 (1993)). The nucleic acid sequences of the present invention enable one of ordinary skill in the art to readily design sequencing primers for such automated sequencing procedures. Commercial instrumentation, such as the Applied Biosystems 377, 3100, 3700, 3730, and 3730×1 DNA Analyzers (Foster City, Calif.), is commonly used in the art for automated sequencing.

Given that the pbp3 gene nucleotide sequence is publicly available (e.g., NCBI Accession No. NC_002953.3; Gene ID NO. 2861917), one skilled in the art may conveniently design a primer set that would amplify the region containing the G88A SNP present on the pbp3 gene. A resulting PCR product (i.e., amplicon) of size approximately 300-700 bp is considered to be suitable for sequencing purposes. In this application, an exemplary forward primer of SEQ ID NO. 5 and a reverse primer of SEQ ID NO. 6 are provided herein. This primer set is shown to sufficient to amplify the G88A gene region on pbp3 gene (See FIG. 3).

To perform sequencing, one skilled in the art would employ a sequencing primer in conjunction with a Sequencing Instrument (e.g., ABI 3130 Genetic Analyzer). An exemplary sequencing primer (i.e., SEQ ID NO. 5) is provided herein.

According to another aspect of the present invention, pyrosequencing may be used to detect the novel SNPs (i.e., G88A and/or G2047A) in pbp3 gene a biological sample. Pyrosequencing involves a cascade of four enzymatic reactions that permit the indirect luciferase-based detection of the pyrophosphate released when DNA polymerase incorporates a dNTP into a template-directed growing oligonucleotide. Each dNTP is added individually and sequentially to the same reaction mixture, and subjected to the four enzymatic reactions. Light is emitted only when a dNTP is incorporated, thus signaling which dNTP in incorporated. Unincorporated dNTPs are degraded by apyrase prior to the addition of the next dNTP. The method can detect heterozygous individuals in addition to heterozygotes. Pyrosequencing uses single stranded template, typically generated by PCR amplification of the target sequence. One of the two amplification primers is biotinylated thereby enabling streptavidin capture of the amplified duplex target. Streptavidin-coated beads are useful for this step. The captured duplex is denatured by alkaline treatment, thereby releasing the non-biotinylated strand. The detection primer used for SNP identification using pyrosequencing is designed to hybridize to a sequence 3' to the SNP.

In one embodiment, the 3' sequence is adjacent, or more preferably, immediately adjacent to the SNP position. Thus, the SNP identity is ascertained when the first nucleotide is incorporated.

Pyrosequencing, as described above, comprises a series of steps for the accurate and qualitative analysis of DNA sequences. Pyrosequencing comprises hybridizing a sequencing primer to a single stranded, PCR amplified, DNA template, and incubating the primers and DNA template with the standard PCR enzymes (e.g. DNA polymerase) with ATP sulfurylase, luciferase and apyrase, and the substrates, adenosine 5' phosphosulfate (APS) and luciferin. The first of four deoxyribonucleotide triphosphates (dNTPs) is added to the reaction as a second step. DNA polymerase catalyzes the incorporation of the deoxyribonucleotide triphosphate to the complementary base in the target DNA template strand. Each incorporation event is accompanied by release of pyrophosphate (PPi) in a quantity equimolar to the amount of incorporated nucleotide. In the third step, ATP sulfurylase quantitatively converts PPi to ATP in the presence of APS. This ATP drives the luciferase mediated conversion of luciferin to oxyluciferin and generates visible light proportional to the amount of ATP. The light produced in the luciferase-catalyzed reaction is detected by a charge coupled device (CCD) camera and seen as a peak in a Pyrogram™. The height of each peak (light signal) is proportional to the number of nucleotides incorporated. As a fourth step, apyrase, a nucleotide degrading enzyme, continuously degrades ATP and unincorporated dNTPs. This reaction switches off the light and regenerates the reaction solution. The next dNTP is then added one at a time and the process is repeated for each dNTP (i.e. dCTP, dGTP, dTTP) in the fifth step. Deoxyadenosine alfa-thio triphosphate (dATPaS) is used as a substitute for deoxyadenosine triphosphate (dATP) since it is efficiently used by the DNA polymerase, but not recognized by the luciferase. As the process continues, the complementary DNA strand is built up and the nucleotide sequence is determined from the signal peaks in the Pyrogram. Pyrosequencing analytical software assigns both genotype and quantifies the signal strength of each allele. Genotype and signal strength are outputted to standard spreadsheet format. Methods for accomplishing pyrosequencing reactions are well known in the art and are described in, for example, U.S. Pat. Nos. 6,258,568 and 6,258,568. Kits, apparatuses and reagents for pyrosequencing are commercially available from, for example, Biotage Ab, (Uppsala, Sweden).

EXPERIMENTAL STUDIES

Example 1

Sequencing of Penicillin Binding Proteins (pbp 1-4) in *Staphylococcus aureus* a) Sequencing of PBP 1-4

In 2009, Contreras-Martel et al. described single nucleotide polymorphisms (SNPs) located in the N-terminus of a *Streptococcus pneumoniae* penicillin binding protein (pbp) gene ultimately leading to decreased susceptibility to beta-lactam antibiotics. Therefore, we focused on sequencing portions of the N-termini of the four (4) penicillin binding proteins (pbps) (i.e., pbp1, pbp2, pbp3 and pbp4) in *Staphylococcus aureus*. We designed the primer sets (See, FIGS. 1-4) to amplify approximately 500 base pairs of the N-termini of these four (4) pbps.

We chose several representative laboratory strains of MSSA, CA-MRSA, and HA-MRSA to amplify DNA for sequencing. To do so, we extracted the genomic DNA from these laboratory strains of *Staphylococcus aureus* by lysing these laboratory strains with an anionic detergent followed by precipitation with 2-propanol using the modified Qiagen Gentra Puregene cell kit method outlined in the "Experimental Methods and Protocols" section (See below). The PCR conditions for amplifying the pbps 1-4 are shown in Table 1.

The resulting PCR products were subject to sequence analysis using the ABI3130 Genetic Analyzer with the sequencing protocol detailed in Table 2. We subsequently used the Megalign program from Lasergene to align the sequences of the three laboratory strains (i.e., MSSA, CA-MRSA, and HA-MRSA) for each of the pbp 1-4.

b) Sequence Alignment and SNP Analysis

Figure 6:
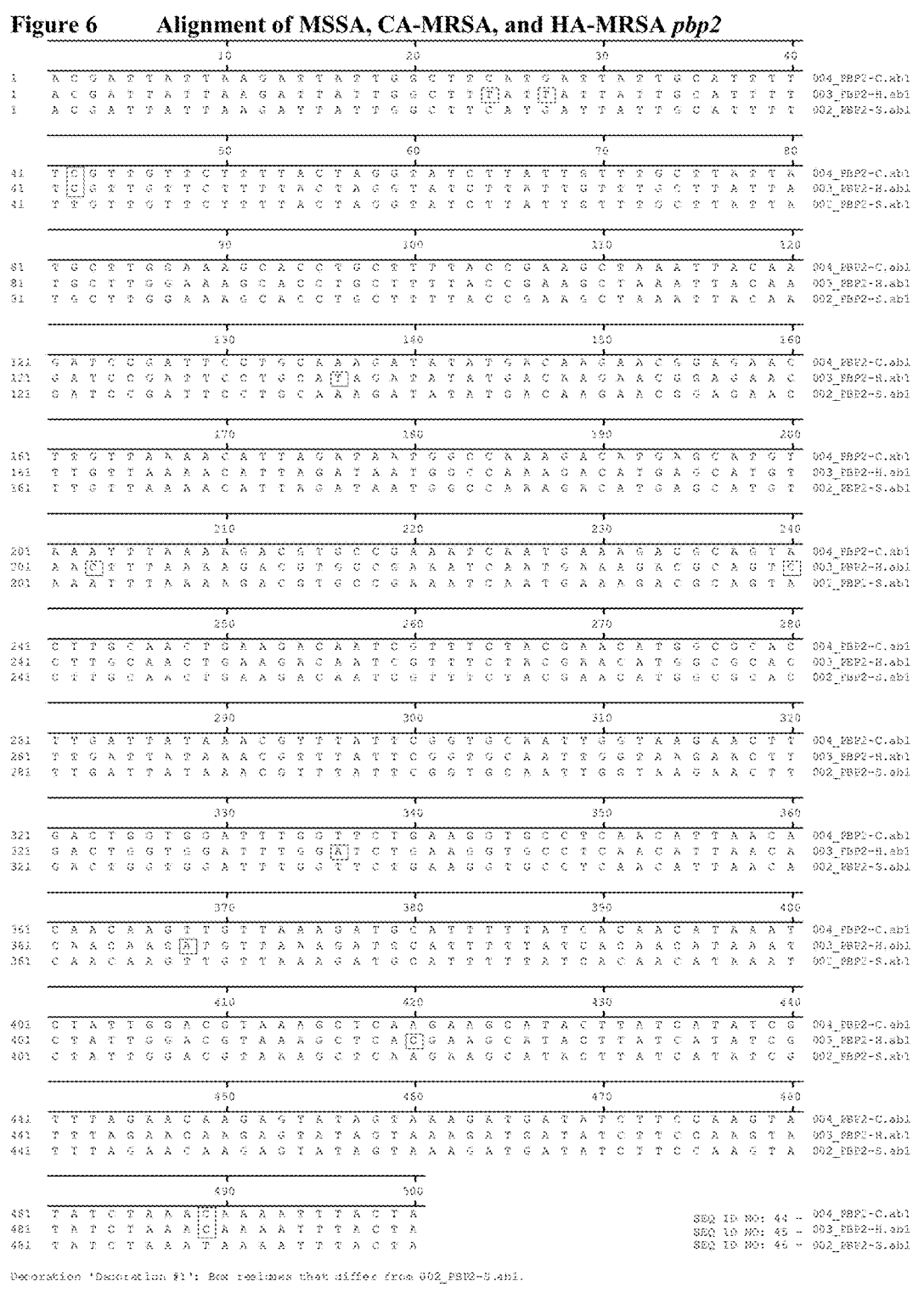
Figure 7:
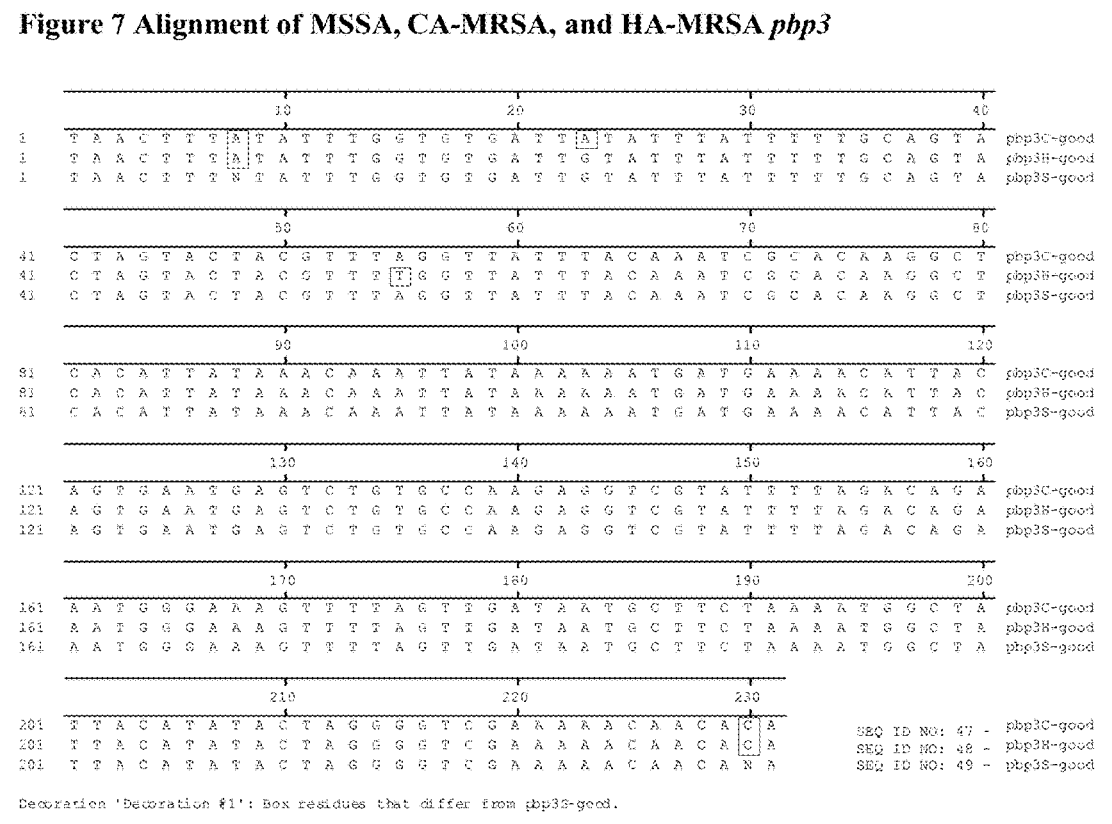
Figure 8:
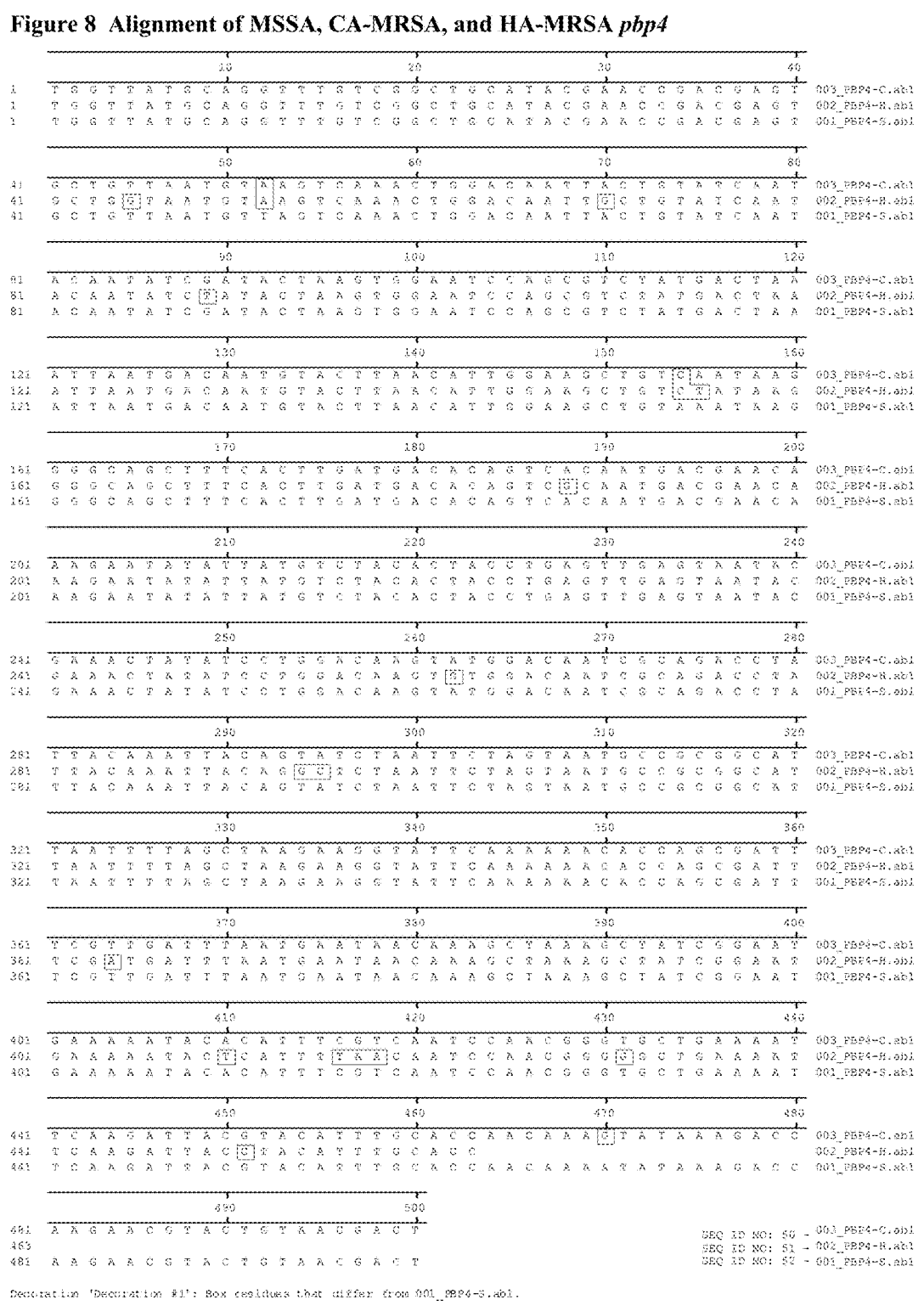

FIG. 5 shows the nucleotide sequence alignment of the pbp 1 among the MSSA, CA-MSRA and HA-MRSA. FIG. 6 shows the nucleotide sequence alignment of the pbp 2 among the MSSA, CA-MSRA and HA-MRSA. FIG. 7 shows the nucleotide sequence alignment of the pbp 3 among the MSSA, CA-MSRA and HA-MRSA. FIG. 8 shows the nucleotide sequence alignment of the pbp 4 among the MSSA, CA-MSRA and HA-MRSA. Nucleotide polymorphisms exhibit among the MSSA, CA-MSRA and HA-MRSA are boxed in black. (See, FIGS. 5-8 for pbp 1-4, respectively). The resulting single nucleotide polymorphisms (SNPs) are summarized in Table 3.

Because we can conveniently use mecA to detect and differentiate MRSA (i.e., HA-MRSA and CA-MRSA) from MSSA, we focused our attention to SNPs that are unique to HA-MRSA or CA-MRSA. We discovered a SNP (i.e., G88A) in the pbp3 gene of CA-MRSA isolates that is unique to CA-MRSA and not present in HA-MRSA or MSSA. This discovery opens a path to evaluate this particular SNP (i.e., G88A) as a potential molecular biomarker for diagnosis of CA-MRSA.

Example 2

Single Nucleotide Polymorphisms (SNPs) in *Staphylococcus aureus* pbp3 Gene and Association with Methicillin-Resistant *Staphylococcus aureus*

We sought to examine the validity of the G88A SNP of the pbp 3 gene as a molecular biomarker for detecting community-associated methicillin-resistant *Staphylococcus aureus* (CA-MRSA). To accomplish this, we obtained and phenotypically classified a large number of clinically isolated strains.

A) Clinical Samples—Determination of Infections with MRSA, CA-MRSA, HA-MRSA or MSSA i) Patient Study In the initial experiments, we obtained biological samples from forty-seven (47) patients suspected of infections caused by different types of *Staphylococcus aureus*; namely: (i) MRSA, (ii) community-associated MRSA (CA-MRSA), (iii) hospital-associated MRSA (HA-MRSA) or (iv) methicillin-susceptible *Staphylococcus aureus* (MSSA).

The gender and age information of these patients are summarized in Table 4. The provided patient information is in accordance with HIPAA regulations regarding patient confidentiality. A random isolate number was provided for each particular clinical isolate. The anatomical sites whereby *Staphylococcus aureus* was collected are provided. As noted in Table 4, the biological samples were collected from various age groups. N/A indicates situations where data were unavailable.

Swabs from the forty-seven (47) patients were obtained from different sites (i.e., vagina, thigh, chin, buttock, etc.). We then isolated single colonies of *Staphylococcus aureus* by streaking the biological samples onto Mannitol Salt agar plates. When cultured onto Mannitol Salt agar, *Staphylococcus aureus* specifically turns the red agar into yellow, which provides ease of identification.

Single colonies of *Staphylococcus aureus* were picked and grown overnight in tryptic soy broth. Cells were then pelleted, had peptidoglycan digested, and were subsequently lysed. RNAse (1.5 µL) was added to remove RNA and excess protein was precipitated. Genomic DNA was precipitated using isopropanol, and then hydrated in buffer. Genomic DNA was isolated from the biological samples using standard protocols as detailed in "Experimental Protocols and Methods". Extracted DNA was used for PCR reactions described herein in this application. Purity of the genomic DNA was confirmed by spectrophotometry ($A_{260}/A_{280}$).

ii) SCC Mec Typing Assay

We also used *Staphylococcus aureus* genomic DNA in an SCC Mec typing assay (See, Tables 5, 6 and FIG. 9) to determine whether the colony was HA-MRSA, CA-MRSA, MSSA, or some other organism.

In essence, we have successfully developed a multiplex PCR assay for SCC Mec typing. The multiplex PCR assay consists of several sets of primers in order to differentiate the different types of *Staphylococcus aureus*. Specifically, mecA primers amplified the MRSA-specific determinant gene, separating MRSA from MSSA. A *Staphylococcus aureus* specific gene, nuc, was used to detect MSSA, and also to distinguish whether an isolate tested was MRSA or a different methicillin-resistant bacterium. SCC Mec typing primers differentiated types I and III from II and IV (all have different size amplicons except II and IV). A ccrAB primer specifically detected the type IV ccrAB, differentiating types II and IV.

If a particular colony tested was SCC Mec type IV, a RT-PCR was performed to see if that strain possessed the Panton-Valentine Leukocidin (PVL) gene (Table 7). By convention, CA-MRSA is defined as SCC type IV and PVL positive. SCC types I-III were considered HA-MRSA. The detailed procedure for the developed assay is provided in details in a related patent application (entitled "Method of Determining Types I, II, III, IV or V of Methicillin-resistant *Staphylococcus aureus* (MRSA) in a Biological Sample" Ser. No. 12/930,663, filed on Jan. 13, 2010, the disclosure of which is incorporated by reference in its entirety).

Table 8 displays the phenotypic analysis of the forty-seven (47) clinical *Staphylococcus aureus* isolates used. Forty-one (41) isolates were determined to be MRSA and six (6) isolates were determined to be MSSA by the PCR described in Table 6. Of the forty-one (41) MRSA isolates, thirty-nine (39) were determined to be CA-MRSA and two (2) were determined to be HA-MRSA by the PCR described in Table 6.

B) PCR Amplification and Sequencing of pbp3 from Clinical *Staphylococcus aureus* Isolates Next, we confirmed our findings (G88A SNP in CA-MRSA) that was observed in laboratory strains (See, Example 1) using the available clinical *Staphylococcus* aureus isolates. To do so, PCR amplification of pbp3 from the forty-seven (47) clinical *Staphylococcus aureus* isolates was carried out using primer sets from FIG. 3 and methods described in Table 1. Table 1 provides a protocol for the PCR amplification of a part of the pbp3 gene of *Staphylococcus aureus* from genomic DNA. High fidelity Taq Polymerase was used to ensure that any polymorphisms observed were not attributable to a low fidelity polymerase.

Resulting amplicons were PCR purified using the Stratagene PCR Purification kit as described by the manufacturer in order to have the purest DNA to sequence. DNA sequencing was performed using the ABI 3130 Genetic Analyzer as described by the manufacturer using the methods described in Table 2.

Nucleotide sequences obtained were entered into the NCBI BLAST program described previously and aligned to the available reference sequences to ensure that the sequencing was successful. If the sequencing was successful, the nucleotide at position 88 within the pbp3 gene was examined to determine if the G88A SNP was present. The results, summarized in FIGS. 10-12, are as follows: two (2) sequenced clinical HA-MRSA strains and four (4) sequenced laboratory HA-MRSA strains had a "G" at nucleotide 88 (See, FIG. 10), 39 sequenced clinical CA-MRSA strains and one (1) sequenced laboratory CA-MRSA strain all possessed the G88A SNP (See, FIG. 11), and six (6) sequenced clinical MSSA strains and two (2) sequenced laboratory MSSA strains had a "G" at position 88 in pbp3 (See, FIG. 12).

Of note is that G88A was not observed in the single SCC IV strain that was PVL negative as well as in a PVL positive MSSA strain (See, FIG. 13), which supports the claim that G88A is a molecular biomarker specific for CA-MRSA. This shows that the SNP (i.e., G88A) is not dependent on PVL or SCC Mec IV alone, but only when both genes are present. Because of this, the SNP (i.e., G88A) described eliminates false positives that occur by using PVL or SCC Mec typing alone.

Example 3

Nucleotide Sequence Alignment of Publicly Available *Staphylococcus aureus* pbp3 Sequences from NCBI A) Representative Laboratory Strains To further confirm our findings in the clinical samples, we chose to examine representative *Staphylococcus aureus* laboratory strain types; namely, Hospital-Associated MRSA (HA-MRSA), Community-Associated MRSA (CA-MRSA), and methicillin susceptible *S. aureus* (MSSA) laboratory strain types. Publicly available amino acid and nucleotide sequences for representative strains (COL=HA-MRSA, Accession: NC_002951.2; USA300=CA-MRSA, Accessions: NC_007793.1 and NC_010079.1; MSSA476=MSSA, Accession: NC_002953.3) were aligned using the National Center for Biotechnology Information (NCBI) BLAST program.

In this sequence analysis, we aligned amino acid sequences of the penicillin binding protein 3 (pbp3). Through the amino acid alignment, two (2) amino acid changes of interest, V30I and D683N, were identified (See, FIG. 14). Both amino acid changes were found only in CA-MRSA (USA300 strain) and not in the other two (2) laboratory strain types.

We next aligned nucleotide sequences of the pbp3 gene and the nucleotide alignment was able to elucidate the exact nucleotide changes responsible for the two (2) amino acid changes; that is, G88A led to V30I and G2047A caused D683N (See, FIG. 15). Together, these data confirm that the discovered nucleotide sequence changes (i.e., SNP) may serve as good biomarkers for CA-MRSA.

B) Additional Representative Laboratory Strains

Fourteen (14) diverse *Staphylococcus aureus* strains have been sequenced and their pbp3 sequences had been publicly available on the NCBI website. The nucleotides sequences of all of these fourteen (14) strains were aligned and compared to each other. The fourteen (14) strains used in our study were COL, Accession: NC_002951.2; N315, Accession: NC_002745.2; Mu50, Accession: NC_002758.2; MRSA252, Accession: NC_002952.2; JH1, Accession: NC_009632.1; JH9, Accession: NC_009487.1; Mu3, Accession: NC_009782.1; USA300 37, Accession: NC_007793.1; USA300 15, Accession: NC_010079.1; MW2, Accession: NC_003923.1; MSSA476, Accession: NC_002953.3; NCTC8325, Accession: NC_007795.1; RF122, Accession: NC_007622.1; and Newman, Accession: NC_009641.1.

After grouping the strains by phenotype, it appeared that the G88A and G2047A SNPs only occur in CA-MRSA strains (See, FIGS. 16 and 17, respectively). Specifically, G88A and G2047A SNPs are present in the USA300 genotype which predominates as the leading cause of CA-MRSA infections. All of the HA-MRSA (7) and MSSA (4) strains possessed guanine (G) at the positions 88 and 2047 in the pbp3 gene (instead of adenine (A)). Two independent USA300 CA-MRSA strains had adenine, while a rare CA-MRSA strain known as MW2 had guanine at position 88 and 2047 within the gene. Since MW2 (USA 400) is a rare strain, and USA300 is a very common MRSA strain (See, Table 9), the SNPs described serve as good molecular markers to detect a high percentage of CA-MRSA. The sequences of the public strains further confirm the utility of our experimentally determined G88A SNP in the detection of CA-MRSA isolates.

Example 4

Statistical Analyses

Using the data compiled from NCBI GenBank sequences and from in-house sequencing, statistical analyses were performed on the available set of sequences (Table 10).

Out of the possible 43 CA-MRSA isolates, 42 possessed the G88A SNP, which translated to 97.7% sensitivity of the SNP to predict CA-MRSA. Out of 25 total MSSA and HA-MRSA strains, none had G88A (i.e., all had G88), which translated to 100% specificity. Positive predictive value, which is the confidence that a strain deemed CA-MRSA is in fact CA-MRSA, was calculated to be 100%, since there were no false positives. Negative predictive value, which is the confidence that a strain that is called non-CA-MRSA is actually HA-MRSA or MSSA, was calculated to be 96.2% since there was a single false negative.

Example 5

Varying Oligonucleotide Sizes and Placement

In order to show that size of oligonucleotides used in the amplification PCR is irrelevant in the detection of the SNPs described, primer sets described in FIG. 18 were designed in various lengths. Amplification was not hindered by these changes, therefore variation in size of oligonucleotides is irrelevant, as long as they flank the SNPs described in order to be properly sequenced.

In order to demonstrate that placement of oligonucleotides used in the amplification PCR is irrelevant in the detection of the SNPs described, as long as the SNPs described fall between the primer sets, primer sets seen in FIG. 19 were designed at varying distances from the SNP, making sure to keep the SNP within the amplicon. Amplification was not hindered by this change, therefore we concluded that variation in location of oligonucleotides is irrelevant, as long as they flank the SNPs described in order to be properly sequenced.

Example 6

Association Between G88A and G2047A

As shown in FIGS. 16 and 17, the two (2) SNPs described in the present invention appear together in absolute linkage disequilibrium and correlate well with each other in all GenBank sequences examined. Detection of either one of the SNPs described works just as well as the other. Sequencing in Example 2 of this patent was limited to the G88A SNP in order to limit superfluous data since the correlation had already been made.

Example 7

Development of an Allele-Specific PCR for Detection of G88A SNP in *Staphylococcus aureus* pbp3 Gene In this experiment, we developed an allele-specific PCR as a useful assay to detect G88A and/or G2047A SNPs in a simple PCR reaction. Primers were designed to G88 or A88 alleles. The G or A served as the final nucleotide of the forward primer. In order to gain extra sensitivity, the penultimate base was altered to be a mismatch, creating dynamic instability of the primers. Therefore, with one mismatch, the next base would absolutely need to match in order to be extended by DNA polymerase.

Design of the primers is shown in FIG. 20, in which *Staphylococcus aureus* and *Staphylococcus epidermidis* were aligned to find regions of high *Staphylococcus aureus* specificity in order to design species-specific reverse primers. The designed primer sequences are listed in Table 11. The different primer combinations and their success in PCR are described in Table 13. The PCR reaction is described in Table 12.

FIG. 21 shows the amplification of only CA-MRSA using the A88 primer set, with no non-specific bands from other organisms, while FIG. 22 shows all HA-MRSA and MSSA strains amplified with the G88 primer set with no non-specific amplification from other organisms.

Example 8

PCR Amplification and Sequencing Assay to Detect G88A SNP or G2047A SNP in Community-Associated *Staphylococcus aureus*

As described in Example 1, an alternative way to detect the G88A or G2047 SNP from a sample is to amplify a segment or the entire gene via polymerase chain reaction (PCR) using a high fidelity DNA polymerase (See, Table 1). The resulting PCR product was run in a cycle sequencing reaction (See, Table 2) and the sequence was read using specialized equipment (i.e., ABI 3130 Genetic Analyzer). PCR amplification and sequencing allowed the direct visualization of the nucleotide present at each position within the gene amplified and allowed the determination of the presence of G88A and/or G2047A SNPs.

EXPERIMENTAL METHODS AND PROTOCOLS

I. Cell Lysis:
1. Centrifuge 4 ml overnight culture of bacteria (e.g., GBS, *C. difficile*, and *Staphylococcus aureus*) into 1.5 ml centrifuge tube at 14,000×g for 2 minutes.
2. Remove as much supernatant as possible to obtain a tight pellet.
3. Add 300 µl cell suspension solution to cell pellet and gently pipette up and down until the cells are suspended.
4. Add 6 µl Lytic enzyme solution (5 µl Lysozyme+1 µl Mutanolysin) and invert the tube 25 times to mix.
5. Incubate at 37° C. for 30 minutes to digest cell walls. Invert samples occasionally during incubation.
6. Centrifuge at 14,000×g for 1 minute to pellet the cells. Remove supernatant.
7. Add 300 µl cell Lysis solution to the cell pellet and gently pipette up and down to lyse the cells.
8. Heat the samples at 80° C. for 5 minutes to complete the lysis.

II. RNase Treatment:
1. Add 1.5 µl RNase A solution to the cell lysate.
2. Mix the samples by inverting the tube 25 times and incubate at 37° C. for 30 minutes.

III. Protein Precipitation:
1. Cool samples to room temperature by placing on ice for 1 minute.
2. Add 100 µl Protein Precipitation Solution to the cell lysate.
3. Vortex vigorously at high speed for 20 seconds to mix the protein precipitation solution uniformly with cell lysate.
4. Place samples on ice for 15 minutes.
5. Centrifuge at 14,000×g for 5 minutes. The precipitated protein should form a tight white pellet. If the protein pellet is not tight repeat step 3 followed by incubation on ice for 5 minutes, then repeat step 5.

IV. DNA Precipitation:
1. Pour the supernatant containing the DNA (leaving behind the precipitated protein pellet) into a clean 1.5 ml centrifuge tube containing 300 ul 100% Isopropanol (2-propanol).
2. Mix the sample by inverting gently 50 times.
3. Centrifuge at 14,000×g for 2 minutes.
4. Pour off the supernatant and drain tube briefly on clean absorbent paper. Add 300 µl 70% Ethanol (210 µl 100% ethanol+90 µl ddH2O) and invert tube several times to wash the DNA pellet.
5. Centrifuge at 14,000×g for 1 minute. Carefully pour off the Ethanol. Pellet may be loose so pour slowly and watch pellet.
6. Invert and drain tube on clean absorbent paper and allow to dry 15-20 minutes.

V. DNA Hydration:
1. Add 50 µl DNA Hydration solution and rehydrate DNA by incubating sample either for 1 hour at 65° C. or overnight at room temperature. If possible, tap tube periodically to aid in dispersing the DNA.
2. Store DNA at −20° C. For long term store at −80° C.

Although the invention has been described in example embodiments, additional modifications and variations would be apparent to those skilled in the art. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

TABLE 1

PCR Amplification of pbp1-4

Master Mix

| | |
|---|---|
| USB 10x PCR Buffer (+2.5 mM MgCl$_2$) | 2.5 µl |
| ddH$_2$O | 15.4 µl |
| SEQ ID 1/3/5/7 (10 µM) | 1.5 µl |
| SEQ ID 2/4/6/8 (10 µM) | 1.5 µl |
| dNTPs (2.5 mM) | 2.0 µl |
| Fidelitaq | 0.1 µl |
| DNA | 2.0 µl |
| Total | 25 µl |

Thermal Profile

| Step | Temp | Time |
|---|---|---|
| 1 | 94° C. | 2 min |
| 2 | 94° C. | 30 sec |
| 3 | 55° C. | 1 min |
| 4 | 72° C. | 1 min |
| 5 | 72° C. | 10 min |
| 6 | 4° C. | hold |

*repeat steps 2-4 for 30 cycles
PCR products purified for sequencing using Stratagene PCR Purification Kit.

TABLE 2 pbp1-4 Sequencing PCR

Master Mix

| | |
|---|---|
| Terminator Ready Reaction Mix v1.1 | 8 µl |
| SEQ ID 1/3/5/7 (1 µM) | 3 µl |
| Purified pbp PCR product | 4 µl |
| ddH$_2$O | 5 µl |
| Total | 20 µl |

Thermal Profile

| Step | Temp | Time |
|---|---|---|
| 1 | 96° C. | 1 min |
| 2 | 96° C. | 10 sec |
| 3 | 50° C. | 5 sec |
| 4 | 60° C. | 4 min |
| 5 | 4° C. | hold |

*repeat steps 2-4 for 25 cycles
Sequences of PCR products analyzed using ABI 3130 genetic analyzer (Applied Biosystems, Foster City, CA)

TABLE 3

Summary of Potential Penicillin Binding Protein SNPs

| | HA-MRSA | CA-MRSA |
|---|---|---|
| pbp1 | G159A, G352A, C399T, A507C | G159A, G352A, C399T, A507C |
| pbp2 | C114T, G117T, T132C, A226T, A293C, A330C, T426A, T458A, A510C | T132C |
| pbp3 | X73A, A120T, X295C | X73A, G88A, X295C |
| pbp4 | T158G, T165A, A183G, G202T, A267C, A268T, A301G, A375G, T407G, A408C, T476A, A522T, C528T, G529T, T530A, T543G | T165A, A267C | pbp1 Alignment from nucleotide 71 to 570
pbp2 Alignment from nucleotide 114 to 562
pbp3 Alignment from nucleotide 66 to 296
pbp4 Alignment from nucleotide 91 to 590

TABLE 4

Patient Data for Biological Samples

| Isolate # | Swab Site | Age | Gender |
|---|---|---|---|
| 1549 | Vulva | 48 | F |
| 8038 | N/A | N/A | N/A |
| 8741 | Vulva | 62 | F |
| 8931 | Vaginal | 56 | F |
| 3481 | Vulva | 53 | F |
| 5565 | Vulva | 19 | F |
| 8050 | N/A | 64 | F |
| 1728 | Vag/Cervical | N/A | F |
| 5624 | Vulva | N/A | F |
| 5427 | Vulva | 29 | F |
| 1646 | Vulva | 42 | F |
| 5974 | Vulva | 31 | F |
| 7419 | Labia | 34 | F |
| 3715 | Vag/End-vulva | 46 | F |
| 2464 | Vag/Labia | 27 | F |
| 6634 | Vaginal | 63 | F |
| 291 | Vaginal | 83 | F |
| 4303 | Vulva Lesion | 60 | F |
| 2368 | Vulva | 73 | F |
| 1586 | Vulva | 53 | F |
| 7526 | Vaginal | 76 | F |
| 2973 | Perineum | 41 | F |
| 4813 | Buttock | 49 | F |
| 4163 | Abcess Rt Buttock | 52 | F |
| 4091 | Thigh | 29 | F |
| 6729 | Buttock | N/A | F |
| 966 | Abdomen | 35 | M |
| 1138 | Buttock | 67 | F |
| 6050 | L Thigh | 42 | F |
| 6388 | L Buttock B | 46 | F |
| 8098 | chin skin | 1 | F |
| 5470 | Groin | 60 | F |
| 3849 | N/A | 22 | F |
| 7384 | N/A | 25 | F |
| 8568 | N/A | 19 | F |
| 5929 | N/A | 24 | F |
| 4852 | N/A | 36 | F |
| 4746 | Vaginal | 60 | F |
| 8555 | N/A | 36 | F |
| 7783 | N/A | 9 | F |
| 7085 | N/A | 49 | F |
| 8358 | N/A | N/A | N/A |
| 8284 | N/A | N/A | N/A |
| 8228 | N/A | N/A | N/A |
| 8305 | N/A | N/A | N/A |
| 2037 | N/A | N/A | N/A |
| 6072 | N/A | N/A | N/A |

TABLE 5

Primers/Probes for SCC Mec Typing sccMec typing of Methicillin-Resistant *Staphylococcus aureus*

| Primers/Probes | Oligonucleotide Sequences 5' to 3' | SEQ ID NOs. |
|---|---|---|
| nuc F1 | GTGCTGGCATATGTATGG | SEQ ID NO. 9 |
| nuc R1 | CGCTTTAATTAATGTCGCAGG | SEQ ID NO. 10 |
| mecA2 F | GTACTGCTATCCACCCTCAAACAG | SEQ ID NO. 11 |
| mecA2 R | GAACCTGGTGAAGTTGTAATCTGG | SEQ ID NO. 12 |
| sccIV ccrAB F2 | GTTGAAAGATGCAAAAGAAGGCA | SEQ ID NO. 13 |
| sccIV ccrAB R1 | GTTAATCATTAGCTCGTGTTTACTATC | SEQ ID NO. 14 |
| mec3b | CGTATGATATTGCAAGGTATAATCC | SEQ ID NO. 15 |
| mec124b | GACTGCGGAGGCTAACTATGTC | SEQ ID NO. 16 |
| Sa5pUTR3 | CTTGTGGATAACTGGAAAGTT | SEQ ID NO. 17 |
| PVL F2 | AGTCAAATCATCAGTTGTTACATCA | SEQ ID NO. 18 |
| PVLR2 | ATCGGAATCTGATGTTGCAG | SEQ ID NO. 19 |
| PVL probe 2 (FAM) | ATGCAGCTCAACATATCACACCTGTA | SEQ ID NO. 20 |

TABLE 6

MRSA sccMEC type Multiplex PCR in differentiating HA-MRSA, CA-MRSA, and MSSA

Master Mix

| | |
|---|---|
| Quanta Perfecta SuperMix for iQ | 12.5 μl |
| ddH$_2$O | 5.4 μl |
| SEQ ID 9 (30 μM) | 0.1 μl |
| SEQ ID 10 (30 μM) | 0.1 μl |
| SEQ ID 11 (30 μM) | 0.1 μl |
| SEQ ID 12 (30 μM) | 0.1 μl |
| SEQ ID 13 (30 μM) | 0.2 μl |
| SEQ ID 14 (30 μM) | 0.2 μl |
| SEQ ID 15 (30 μM) | 0.6 μl |
| SEQ ID 16 (30 μM) | 0.1 μl |
| SEQ ID 17 (30 μM) | 0.6 μl |
| DNA | 10.0 μl |
| Total | 30.0 μl |

Thermal Profile

| Step | Temp | Time | |
|---|---|---|---|
| 1 | 94° C. | 3 min | |
| 2 | 94° C. | 30 sec | |
| 3** | 70° C. | 1 min | |
| 4 | 72° C. | 1 min | -Run using Stratagene Mx3000p |
| 5 | 72° C. | 10 min | |
| 6 | 4° C. | hold | |

*repeat steps 2-4 tor 40 cycles
**Step 3 is to make this a touch-down PCR. Every cycle, step 3 drops 1° C. until the temperature is 58° C., at which point, step 3 holds at 58° C.

TABLE 7

Panton-Valentine Leukocidin RT-PCR in determining whether a MRSA isolate is CA-MRSA Master Mix

| | |
|---|---|
| Quanta Perfecta SuperMix for iQ | 7.5 μl |
| ddH$_2$O | 3.9 μl |
| SEQ ID 18 (30 μM) | 0.4 μl |
| SEQ ID 19 (30 μM) | 0.4 μl |
| SEQ ID 20 (10 μM) | 0.3 μl |
| DNA | 2.5 μl |
| Total | 15.0 μl |

Thermal Profile

| Step | Temp | Time |
|---|---|---|
| 1 | 50° C. | 2 min |
| 2 | 94° C. | 3 min |
| 3 | 94° C. | 15 sec |
| 4 | 60° C. | 30 sec |

*repeat steps 2-4 for 38 cycles
Read using Stratagene Mx3000p, reading fluorescence on FAM channel.
Amplification in the form of a C$_t$ score showed presence of PVL toxin.
Isolates determined to be sccMec type IV and have PVL present were considered Community-Associated MRSA.

TABLE 8

Summary of Biological Samples from Patients

| *Staphylococcus aureus* Types | # of Isolates |
|---|---|
| MRSA | 41 |
| HA-MRSA | 2 |
| CA-MRSA | 39 |
| MSSA | 6 |

TABLE 9

CDC Study showing the frequency of different HA-MRSA and CA-MRSA strains

| PFGE type | No. (%) |
|---|---|
| USA100 | 1,063 (53.6) |
| USA200 | 15 (0.8) |
| USA300 | 627 (31.6) |
| USA400 | 6 (0.3) |
| USA500 | 74 (3.7) |
| USA600 | 14 (0.7) |
| USA700 | 8 (0.4) |
| USA800 | 38 (1.9) |
| USA1000 | 16 (0.8) |
| USA1100 | 8 (0.4) |
| Iberian | 36 (1.8) |
| Novel type | 11 (0.6) |
| EMRSA15 | 4 (0.2) |
| Group D | 2 (0.1) |
| Nontypeable | 1 (0.1) |
| Not done | 61 (3.1) |
| Total | 1,984 |

USA300 is shown to be the most common CA-MRSA. The table also shows that MW2 (also named USA400) is a very rare CA-MRSA strain. Since FIGS. 11 and 16 showed that USA300 has the G88A SNP, the SNP can serve as a good marker for CA-MRSA. J Clin Microbiol. 2009 May; 47(5): 1344-51. Representative CA-MRSA PFGE types are boxed.

TABLE 10

Derivation of Statistics a) Breakdown of Sequencing vs. in-house PCR and GenBank
  43 CA-MRSA (39 clinical samples, 1 laboratory in-house, 3 GenBank)
    42 had G88A SNP (true pos.), 1 was G88 (false neg.)
  13 HA-MRSA (2 clinical, 4 laboratory in-house, 7 GenBank)
    13 G88 (true neg.), no G88A (false pos.)
  12 MSSA (6 clinical, 2 laboratory in-house, 4 GenBank)
    12 G88 (true neg.), no G88A (false pos.)

b) $\text{Sensitivity \%} = \frac{\text{\# of True Positives}}{\text{\# True Positives} + \text{\# False Negatives}} * 100$

42/[42 + 1] * 100
42/43 * 100 = 97.7% c) $\text{Specificity \%} = \frac{\text{\# of True Negatives}}{\text{\# True Negatives} + \text{\# False Positives}} * 100$

25/25 + 0 * 100
25/25 * 100 = 100% d) $\frac{\text{Positive Predictive}}{\text{Value \%}} = \frac{\text{\# of True Positives}}{\text{\# True Positives} + \text{\# False Positives}} * 100$

42/42 + 0 * 100
42/42 * 100 = 100% e) $\frac{\text{Negative Predictive}}{\text{Value \%}} = \frac{\text{\# of True Negatives}}{\text{\# True Negatives} + \text{\# False Negatives}} * 100$

25/25 + 1 * 100
25/26 * 100 = 96.2%

Statistical derivation of sensitivity, specificity, positive predictive value, and negative predictive value for G88A SNP's ability to predict CA-MRSA. Statistical methods used are from Altman DG, Bland J. M. (1994). "Diagnostic tests. 1: Sensitivity and specificity" *BMJ* 308 (6943): 1552.

TABLE 11

Allele-Specific PCR Primers
Allele-Specific PCR to Detect CA-MRSA SNP

| | | |
|---|---|---|
| CA-MRSA-For-TA | CTTTATATTTGGTGTGATTA | (SEQ ID NO. 25) |
| CA-MRSA-For-AA | CTTTATATTTGGTGTGATAA | (SEQ ID NO. 26) |
| CA-MRSA-For-GA | CTTTATATTTGGTGTGATGA | (SEQ ID NO. 27) |
| CA-MRSA-For-CA | CTTTATATTTGGTGTGATCA | (SEQ ID NO. 28) |
| CA-MRSA-For-TG | CTTTATATTTGGTGTGATTG | (SEQ ID NO. 29) |
| CA-MRSA-For-AG | CTTTATATTTGGTGTGATAG | (SEQ ID NO. 30) |
| CA-MRSA-For-GG | CTTTATATTTGGTGTGATGG | (SEQ ID NO. 31) |
| CA-MRSA-For-CG | CTTTATATTTGGTGTGATCG | (SEQ ID NO. 32) |
| CA-MRSA-Rev-1 | GATTGTGTTGTTTTTCGACC | (SEQ ID NO. 33) |
| CA-MRSA-Rev-2 | ATAACTTTTCAGCCGTATCC | (SEQ ID NO. 34) |
| CA-MRSA-Rev-3 | TCCATCTGCTAACATAGC | (SEQ ID NO. 35) |
| CA-MRSA-Rev-4 | GATTTTCCGATTTTCGATAAC | (SEQ ID NO. 36) |

TABLE 12

Allele-Specific PCR to Detect G88A SNP

Master Mix

| | |
|---|---|
| Quanta Perfecta SuperMix for iQ | 12.5 μl |
| ddH$_2$O | 9.0 μl |
| SEQ ID 26 (50 μM)* | 0.5 μl |
| SEQ ID 36 (50 μM) | 0.5 μl |
| DNA (4 ng/μl) | 2.5 μl |
| Total | 25 μl |

CA-MRSA specific.
*For HA-MRSA & MSSA control use SEQ ID 30

Thermal Profile

| Step | Temp | Time |
|---|---|---|
| 1 | 95° C. | 3 min |
| 2 | 95° C. | 30 sec |
| 3 | 54° C. | 30 sec |
| 4 | 72° C. | 30 sec |
| 5 | 72° C. | 5 min |
| 6 | 4° C. | hold |

*repeat steps 2-4 for 35 cycles

TABLE 13

Determination of Optimal Primer Pairs for Allele-Specific PCR

| Forward Primer (SEQ ID #) | CA-MRSA | Non-CA S. aureus | Reverse Primer (SEQ ID #) | Notes |
|---|---|---|---|---|
| TA (25) | + | − | R1 (33) | *Variable |
|  | + | + | R2 (34) |  |
|  | + | + | R3 (35) |  |
|  | + | + | R4 (36) |  |
| AA (26) | + | − | R1 (33) |  |
|  | + | − | R2 (34) |  |
|  | + | − | R3 (35) |  |
|  | + | − | R4 (36) | *brightest amplification |
| CA (28) | + | − | R1 (33) |  |
|  | + | − | R2 (34) |  |
|  | + | − | R3 (35) |  |
|  | + | − | R4 (36) |  |
| GA (27) | + | − | R1 (33) |  |
|  | + | − | R2 (34) |  |
|  | + | − | R3 (35) |  |
|  | + | − | R4 (36) |  |
| TG (29) | + | + | R1 (33) |  |
|  | + | + | R2 (34) |  |
|  | + | + | R3 (35) |  |
|  | + | + | R4 (36) |  |
| AG (30) | − | + | R1 (33) |  |
|  | − | + | R2 (34) |  |
|  | − | + | R3 (35) |  |
|  | − | + | R4 (36) | *brightest amplification |
| CG (32) | +/− | + | R1 (33) |  |
|  | +/− | + | R2 (34) | *may need further optimization |
|  | +/− | + | R3 (35) |  |
|  | +/− | + | R4 (36) |  |
| GG (31) | − | + | R1 (33) |  |
|  | − | + | R2 (34) |  |
|  | − | + | R3 (35) |  |
|  | − | + | R4 (36) |  |

"+" = amplification; "−" = no amplification; "+/−" = variable

What is claimed is:

1. A method of determining the presence of community-associated methicillin-resistant *Staphylococcus aureus* (CA-MRSA) in a human, comprising the steps of:
   (a) obtaining a biological sample from a human suspected of having a CA-MRSA infection, wherein said biological sample is fluid or tissue;
   (b) isolating genomic material from said biological sample;
   (c) performing a polymerase chain reaction (PCR) targeted against the penicillin binding protein 3 gene (SEQ ID NO: 39) present in said isolated genomic material to generate an amplicon containing the SNP G88A by using a forward primer consisting of SEQ ID NO: 1 and a reverse primer consisting of SEQ ID NO: 2;
   (d) performing a sequencing reaction on said generated amplicon by using a sequencing primer consisting of SEQ ID NO:1;
   (e) detecting the presence of adenine (A) at nucleotide position 88 (SNP G88A) in said penicillin binding protein 3 gene in said amplicon; and
   (f) determining the presence of CA-MRSA in said human by said presence of said adenine at said nucleotide position 88 (SNP G88A) in said amplicon.

2. The method of claim 1, wherein said biological sample is whole blood, plasma, urine, or exudate from an infected site.

3. The method of claim 1, wherein said isolating step is performed using guanidinium hydrochloride.

4. A method of determining the presence of community-associated methicillin-resistant *Staphylococcus aureus* (CA-MRSA) in a human, comprising the steps of:
   (a) obtaining a biological sample from a human suspected of having a CA-MRSA infection, wherein said biological sample is fluid or tissue;
   (b) isolating genomic material from said biological sample;
   (c) performing a polymerase chain reaction (PCR) targeted against the penicillin binding protein 3 gene (SEQ ID NO: 39) present in said isolated genomic material to generate an amplicon containing the SNP G88A by using a forward primer consisting of SEQ ID NO: 3 and a reverse primer consisting of SEQ ID NO: 4;
   (d) performing a sequencing reaction on said generated amplicon by using a sequencing primer consisting of SEQ ID NO:3;
   (e) detecting the presence of adenine (A) at nucleotide position 88 (SNP G88A) in said penicillin binding protein 3 gene in said amplicon; and
   (f) determining the presence of CA-MRSA in said human by said presence of said adenine at said nucleotide position 88 (SNP G88A) in said amplicon.

5. A method of determining the presence of community-associated methicillin-resistant *Staphylococcus aureus* (CA-MRSA) in a human, comprising the steps of:
   (a) obtaining a biological sample from a human suspected of having a CA-MRSA infection, wherein said biological sample is fluid or tissue;
   (b) isolating genomic material from said biological sample;
   (c) performing a polymerase chain reaction (PCR) targeted against the penicillin binding protein 3 gene (SEQ ID NO: 39) present in said isolated genomic material to generate an amplicon containing the SNP G88A by using a forward primer consisting of SEQ ID NO: 5 and a reverse primer consisting of SEQ ID NO: 6;
   (d) performing a sequencing reaction on said generated amplicon by using a sequencing primer consisting of SEQ ID NO: 5;
   (e) detecting the presence of adenine (A) at nucleotide position 88 (SNP G88A) in said penicillin binding protein 3 gene in said amplicon; and
   (f) determining the presence of CA-MRSA in said human by said presence of said adenine at said nucleotide position 88 (SNP G88A) in said amplicon.

6. A method of determining the presence of community-associated methicillin-resistant *Staphylococcus aureus* (CA-MRSA) in a human, comprising the steps of:
   (a) obtaining a biological sample from a human suspected of having a CA-MRSA infection, wherein said biological sample is fluid or tissue;
   (b) isolating genomic material from said biological sample;
   (c) performing a polymerase chain reaction (PCR) targeted against the penicillin binding protein 3 gene (SEQ ID NO: 39) present in said isolated genomic material to generate an amplicon containing the SNP G88A by using a forward primer consisting of SEQ ID NO: 7 and a reverse primer consisting of SEQ ID NO: 8;
   (d) performing a sequencing reaction on said generated amplicon by using a sequencing primer consisting of SEQ ID NO: 7;
   (e) detecting the presence of adenine (A) at nucleotide position 88 (SNP G88A) in said penicillin binding protein 3 gene in said generated amplicon; and
   (f) determining the presence of CA-MRSA in said human by said presence of said adenine at said nucleotide position 88 (SNP G88A) in said generated amplicon.

7. A method of determining the presence of community-associated methicillin-resistant *Staphylococcus aureus* (CA-MRSA) in a human, comprising the steps of:
   (a) obtaining a biological sample from a human suspected of having CA-MRSA infection, wherein said biological sample is fluid or tissue;
   (b) isolating genomic material from said biological sample;
   (c) performing an allele-specific PCR targeted against penicillin binding protein 3 gene (SEQ ID NO: 39) on said isolated genomic material to obtain an amplicon containing the SNP G88A by using a forward primer selected from the group consisting of SEQ ID NO: 25, SEQ ID NO: 26, SEQ ID NO: 27, and SEQ ID NO: 28 and a reverse primer selected from the group consisting of SEQ ID NO: 33, SEQ ID NO: 34, SEQ ID NO: 35 and SEQ ID NO: 36; and
   (d) determining the presence of CA-MRSA in said human as indicated by generation of said amplicon.

8. The method of claim 7, wherein said forward primer consists of SEQ ID NO: 26 and said reverse primer consists of SEQ ID NO: 36.

9. The method of claim 4, wherein said biological sample is whole blood, plasma, urine, or exudate from an infected site.

10. The method of claim 5, wherein said biological sample is whole blood, plasma, urine, or exudate from an infected site.

11. The method of claim 6, wherein said biological sample is whole blood, plasma, urine, or exudate from an infected site.

12. The method of claim 7, wherein said biological sample is whole blood, plasma, urine, or exudate from an infected site.

13. The method of claim 4, wherein said isolating step is performed using guanidinium hydrochloride.

14. The method of claim 5, wherein said isolating step is performed using guanidinium hydrochloride.

15. The method of claim 6, wherein said isolating step is performed using guanidinium hydrochloride.

16. The method of claim 7, wherein said isolating step is performed using guanidinium hydrochloride.

* * * * *

SEQUENCE LISTING

<160> NUMBER OF SEQ ID NOS: 132

<210> SEQ ID NO 1
<211> LENGTH: 20
<212> TYPE: DNA
<213> ORGANISM: Staphylococcus aureus

<400> SEQUENCE: 1 agggggcagtc ctacttgttg                                                    20

<210> SEQ ID NO 2
<211> LENGTH: 23
<212> TYPE: DNA
<213> ORGANISM: Staphylococcus aureus

<400> SEQUENCE: 2
gcacctttaa gttcaccagt atc                                                 23

<210> SEQ ID NO 3
<211> LENGTH: 20
<212> TYPE: DNA
<213> ORGANISM: Staphylococcus aureus

<400> SEQUENCE: 3
ggtgggaaat ccaactcaaa                                                     20

<210> SEQ ID NO 4
<211> LENGTH: 20
<212> TYPE: DNA
<213> ORGANISM: Staphylococcus aureus

<400> SEQUENCE: 4
acctgttacg ccatcagaat                                                     20

<210> SEQ ID NO 5
<211> LENGTH: 23
<212> TYPE: DNA
<213> ORGANISM: Staphylococcus aureus

<400> SEQUENCE: 5
tcaaatgatg aaatcgttca aaa                                                 23

<210> SEQ ID NO 6
<211> LENGTH: 20
<212> TYPE: DNA
<213> ORGANISM: Staphylococcus aureus

<400> SEQUENCE: 6
tccgattgtg ttgtttttcg                                                     20

<210> SEQ ID NO 7
<211> LENGTH: 20
<212> TYPE: DNA
<213> ORGANISM: Staphylococcus aureus

<400> SEQUENCE: 7
ttatgacacc atatgcacaa                                                     20

<210> SEQ ID NO 8
<211> LENGTH: 20
<212> TYPE: DNA
<213> ORGANISM: Staphylococcus aureus

<400> SEQUENCE: 8

```
tctaaaatgg cgtagtctct                                              20

<210> SEQ ID NO 9
<211> LENGTH: 18
<212> TYPE: DNA
<213> ORGANISM: Staphylococcus aureus

<400> SEQUENCE: 9
gtgctggcat atgtatgg                                                18

<210> SEQ ID NO 10
<211> LENGTH: 21
<212> TYPE: DNA
<213> ORGANISM: Staphylococcus aureus

<400> SEQUENCE: 10
cgctttaatt aatgtcgcag g                                            21

<210> SEQ ID NO 11
<211> LENGTH: 24
<212> TYPE: DNA
<213> ORGANISM: Staphylococcus aureus

<400> SEQUENCE: 11
gtactgctat ccaccctcaa acag                                         24

<210> SEQ ID NO 12
<211> LENGTH: 24
<212> TYPE: DNA
<213> ORGANISM: Staphylococcus aureus

<400> SEQUENCE: 12
gaacctggtg aagttgtaat ctgg                                         24

<210> SEQ ID NO 13
<211> LENGTH: 23
<212> TYPE: DNA
<213> ORGANISM: Staphylococcus aureus

<400> SEQUENCE: 13
gttgaaagat gcaaaagaag gca                                          23

<210> SEQ ID NO 14
<211> LENGTH: 27
<212> TYPE: DNA
<213> ORGANISM: Staphylococcus aureus

<400> SEQUENCE: 14
gttaatcatt agctcgtgtt tactatc                                      27

<210> SEQ ID NO 15
<211> LENGTH: 25
<212> TYPE: DNA
<213> ORGANISM: Staphylococcus aureus

<400> SEQUENCE: 15
cgtatgatat tgcaaggtat aatcc                                        25

<210> SEQ ID NO 16
<211> LENGTH: 22
<212> TYPE: DNA
<213> ORGANISM: Staphylococcus aureus
```

<400> SEQUENCE: 16
gactgcggag gctaactatg tc                                           22

<210> SEQ ID NO 17
<211> LENGTH: 21
<212> TYPE: DNA
<213> ORGANISM: Staphylococcus aureus

<400> SEQUENCE: 17
cttgtggata actggaaagt t                                            21

<210> SEQ ID NO 18
<211> LENGTH: 25
<212> TYPE: DNA
<213> ORGANISM: Staphylococcus aureus

<400> SEQUENCE: 18
agtcaaatca tcagttgtta catca                                        25

<210> SEQ ID NO 19
<211> LENGTH: 20
<212> TYPE: DNA
<213> ORGANISM: Staphylococcus aureus

<400> SEQUENCE: 19
atcggaatct gatgttgcag                                              20

<210> SEQ ID NO 20
<211> LENGTH: 26
<212> TYPE: DNA
<213> ORGANISM: Staphylococcus aureus

<400> SEQUENCE: 20
atgcagctca acatatcaca cctgta                                       26

<210> SEQ ID NO 21
<211> LENGTH: 19
<212> TYPE: DNA
<213> ORGANISM: Staphylococcus aureus

<400> SEQUENCE: 21
tcaaatgatg aaatcgttc                                               19

<210> SEQ ID NO 22
<211> LENGTH: 18
<212> TYPE: DNA
<213> ORGANISM: Staphylococcus aureus

<400> SEQUENCE: 22
ccgattgtgt tgtttttc                                                18

<210> SEQ ID NO 23
<211> LENGTH: 22
<212> TYPE: DNA
<213> ORGANISM: Staphylococcus aureus

<400> SEQUENCE: 23
gaaaaatcaa atgatgaaat cg                                           22

<210> SEQ ID NO 24
<211> LENGTH: 21
<212> TYPE: DNA
<213> ORGANISM: Staphylococcus aureus

<400> SEQUENCE: 24
cattttagaa gcattatcaa c                                       21

<210> SEQ ID NO 25
<211> LENGTH: 20
<212> TYPE: DNA
<213> ORGANISM: Staphylococcus aureus

<400> SEQUENCE: 25
ctttatattt ggtgtgatta                                         20

<210> SEQ ID NO 26
<211> LENGTH: 20
<212> TYPE: DNA
<213> ORGANISM: Staphylococcus aureus

<400> SEQUENCE: 26
ctttatattt ggtgtgataa                                         20

<210> SEQ ID NO 27
<211> LENGTH: 20
<212> TYPE: DNA
<213> ORGANISM: Staphylococcus aureus

<400> SEQUENCE: 27
ctttatattt ggtgtgatga                                         20

<210> SEQ ID NO 28
<211> LENGTH: 20
<212> TYPE: DNA
<213> ORGANISM: Staphylococcus aureus

<400> SEQUENCE: 28
ctttatattt ggtgtgatca                                         20

<210> SEQ ID NO 29
<211> LENGTH: 20
<212> TYPE: DNA
<213> ORGANISM: Staphylococcus aureus

<400> SEQUENCE: 29
ctttatattt ggtgtgattg                                         20

<210> SEQ ID NO 30
<211> LENGTH: 20
<212> TYPE: DNA
<213> ORGANISM: Staphylococcus aureus

<400> SEQUENCE: 30
ctttatattt ggtgtgatag                                         20

<210> SEQ ID NO 31
<211> LENGTH: 20
<212> TYPE: DNA
<213> ORGANISM: Staphylococcus aureus

<400> SEQUENCE: 31
ctttatattt ggtgtgatgg                                         20

<210> SEQ ID NO 32
<211> LENGTH: 20
<212> TYPE: DNA

```
<213> ORGANISM: Staphylococcus aureus

<400> SEQUENCE: 32
ctttatattt ggtgtgatcg                                                    20

<210> SEQ ID NO 33
<211> LENGTH: 20
<212> TYPE: DNA
<213> ORGANISM: Staphylococcus aureus

<400> SEQUENCE: 33
gattgtgttg tttttcgacc                                                    20

<210> SEQ ID NO 34
<211> LENGTH: 20
<212> TYPE: DNA
<213> ORGANISM: Staphylococcus aureus

<400> SEQUENCE: 34
ataacttttc agccgtatcc                                                    20

<210> SEQ ID NO 35
<211> LENGTH: 18
<212> TYPE: DNA
<213> ORGANISM: Staphylococcus aureus

<400> SEQUENCE: 35
tccatctgct aacatagc                                                      18

<210> SEQ ID NO 36
<211> LENGTH: 21
<212> TYPE: DNA
<213> ORGANISM: Staphylococcus aureus

<400> SEQUENCE: 36
gattttccga ttttcgataa c                                                  21

<210> SEQ ID NO 37
<211> LENGTH: 2235
<212> TYPE: DNA
<213> ORGANISM: Staphylococcus aureus

<400> SEQUENCE: 37
atggcgaagc aaaaaattaa aattaaaaaa aataaaatag ggcagtcct acttgttggt         60 ttattcggac tgctcttttt tatattggtt ttaagaattt catatatcat gattactgga       120
cattctaatg gtcaagattt agtcatgaag gcaaatgaga agtatttagt taagaatgca       180
caacaaccag aacgaggaaa gatatatgat cgtaatggta agtgctagc agaagatgta        240 gaaagatata aacttgttgc agtaatagat aaaaaggcga gtgccaattc taaaaaacct       300
aggcatgtag ttgataaaaa agagactgca agaaaattat ctacagtcat tgatatgaag       360
ccagaggaaa ttgaaaagag acttagtcaa agaaagcct tccaaattga atttggacgc       420
aaaggaacaa atttaacgta tcaggacaaa ttgaaaatag agaaaatgaa tttgcctggt       480
atttctttat tgcctgaaac agaacgattt tatccaaatg gcaattttgc atcacactta       540
attggtagag ctcagaaaaa tccggatact ggtgaactta aggtgcgct tggagttgaa       600 aagattttg atagttattt aagtggatct aaaggatctt tgagatatat tcatgatatt       660
tggggatata ttgcaccaaa tactaaaaaa gagaagcagc ctaaacgtgg tgatgatgtc       720
catttaacaa tcgattcaaa tattcaagta tttgttgaag aggctttaga tggcatggtt       780
```

```
gaaagatacc agccgaaaga tttatttgcg gttgtcatgg atgccaaaac tggagaaatt    840
ttagcataca gtcagcgacc aacatttaat cctgaaactg gtaaagattt tggtaaaaag    900
tgggcaaatg atctatatca aaacacatat gagcctggat caacatttaa atcatatggg    960
ttagcagctg ctattcaaga aggtgctttt gatcctgata gaaatataa atctggacat    1020 agagatatta tgggttcacg tatttcagac tggaatagag tcggttgggg tgaaatccca    1080
atgtcactcg gatttactta ttcatctaat acattgatga tgcatttaca agatttagtt    1140
ggtgcagaca aaatgaaatc ttggtatgaa cgatttggat ttggaaaatc aactaaaggt    1200
atgtttgatg gagaagcacc tggtcaaatt ggatggagta atgagttaca acaaaaaacg    1260
tcatcatttg gtcaatcgac aactgtaaca cctgttcaaa tgttacaggc gcaatcagcg    1320
ttctttaatg atggtaatat gttaaaacca tggtttgtga atagcgttga aaatcctgtt    1380
agtaaaagac aattttataa aggtcaaaaa caaatcgcag gcaaaccaat aacaaaagat    1440
actgctgaaa aagttgaaaa gcaattggat ttagttgtga atagtaagaa gagtcacgct    1500
gcaaactatc gtattgatgg ttatgaggtc gaaggtaaga ctggtacagc acaagtcgct    1560
gcacctaatg gtggtggata cgttaaaggt ccaaacccat atttcgtaag ttttatgggt    1620
gacgcaccga agaaaaatcc taaagttatt gtatacgctg gtatgagctt ggcacaaaaa    1680
aatgaccaag aagcttatga attaggtgtt agtaaagcgt ttaaaccaat aatgaaaat    1740 actttgaaat atttaaatgt aggtaaatca aaagatgaca catctaatgc agagtatagt    1800
aaagtgccag atgttgaagg tcaagacaaa caaaaagcta ttgataatgt gagtgcaaaa    1860
tcattagaac cagttactat cggttctggc acacaaataa aagcgcaatc tataaaagca    1920
gggaataaag tcttacctca tagtaaagta ctgttattaa cagatggaga cttaactatg    1980
cctgacatgt caggatggac gaaagaagat gtcattgctt ttgaaaacct aacaaatatt    2040
aaagtgaatt taaaggtag cggttttgtg tcccaccaat caattagtaa gggacaaaaa    2100
cttactgaaa aagataaaat agacgtagaa ttttcatcag agaatgtaga cagcaattcg    2160
acgaataatt ctgattcaaa ttcagatgat aagaagaaat ctgacagtaa aactgacaaa    2220
gataagtcgg actaa    2235
```

<210> SEQ ID NO 38
<211> LENGTH: 2151
<212> TYPE: DNA
<213> ORGANISM: Staphylococcus aureus

<400> SEQUENCE: 38

```
atgacggaaa acaaaggatc ttctcagcct aagaaaaatg gtaataatgg tgggaaatcc     60
aactcaaaaa agaatagaaa tgtgaagaga acgattatta agattattgg cttcatgatt    120
attgcatttt tgttgttct tttactaggt atcttattgt ttgcttatta tgcttggaaa    180
gcacctgctt ttaccgaagc taaattacaa gatccgattc ctgcaaagat atatgacaag    240
aacggagaac ttgttaaaac attagataat ggccaaagac atgagcatgt aaatttaaaa    300
gacgtgccga atcaatgaa agacgcagta cttgcaattg aagacaatcg tttctacgaa    360
catggcgcac ttgattataa acgttttatc ggtgcaattg gtaagaactt gactggtgga    420
tttggttctg aaggtgcctc aacattaaca caacaagttg ttaaagatgc attttatca    480 caacataaat ctattggacg taaagctcaa gaagcatact tatcatatcg tttagaacaa    540
gagtatagta aagatgatat cttccaagta tatctaaata aaatttacta ttctgatggc    600
```

-continued

```
gtaacaggta ttaaagctgc tgctaagtat tactttaata agatttaaa agatttaaac      660 ttagcggaag aagcttattt agccggttta cctcaggttc caaacaacta taatatttat      720
gatcatccaa aagctgctga agatcgtaaa aacactgttt tatacttaat gcattatcat      780
aaacgcatta cagataaaca gtgggaagat gctaagaaaa tcgatttaaa agcgaactta      840
gtaaatcgta ctgctgaaga acgtcaaaac attgatacaa atcaagattc tgagtataat      900
tcatacgtta actttgtaaa atctgaatta atgaataata aagcattcaa agatgaaaat      960
ttaggtaatg tattacaaag tggtattaaa atttatacaa acatggataa agatgttcaa     1020
aaaacattac aaaatgatgt tgataatggt agcttctaca agaataaaga ccaacaagtt     1080
ggtgcaacga ttcttgatag taaaactggt ggtttagttg ctatatctgg cggacgtgat     1140
ttcaaagacg tcgttaacag aaaccaagca acagatccac accctactgg ttcatcttta     1200
aaacctttct tagcgtatgg aacctgccatt gaaaatatga atgggcaac aaaccatgcg     1260 attcaagatg aatcttcata tcaagttgat ggatctacat ttagaaacta tgatacgaag     1320
agtcacggta ctgtatctat ttatgatgct ttacgacaaa gtttcaatat cccagcttta     1380
aaagcttggc aatcagttaa gcaaaatgct ggtaatgatg cacctaagaa attcgctgcc     1440
aaacttggct taaactacga aggcgatatt ggtccatctg aagtacttgg tggttctgct     1500
tcagaattct caccaacaca attagcatca gcatttgctg caatcgctaa cggtggtact     1560
tataacaacg cgcattcaat tcaaaaagta gttactcgtg atggtgaaac aatcgaatac     1620
gatcatacta gccataaagc gatgagtgat tacactgcat acatgttagc tgagatgcta     1680
aaaggtacat ttaaaccata tggttctgca tatggccatg gtgtatctgg agtaaatatg     1740
ggtgctaaga caggtactgg tacttacggt gctgaaactt attcacaata taatttacct     1800
gataatgcag cgaaagacgt gtggattaac ggctttacac ctcaatacac tatgtcagtg     1860
tggatgggct tcagtaaagt taaacaatat ggtgaaaact catttgtggg acatagccaa     1920
caagaatatc cacagttctt atatgaaaat gtgatgtcaa aaatttcatc tagagatggc     1980
gaagacttta aacgtcctag ctcagtaagt ggtagtatcc catcaatcaa tgtttctggt     2040
agtcaagata caacactac aaatcgtagt acacacggtg gtagtgacac atcagcaaac     2100
agcagtggta ctgcacaatc aaataacaat actagatctc aacaatcttg a             2151
```

<210> SEQ ID NO 39
<211> LENGTH: 2076
<212> TYPE: DNA
<213> ORGANISM: Staphylococcus aureus

<400> SEQUENCE: 39

```
ttgttaaaaa gactaaaaga aaaatcaaat gatgaaatcg ttcaaaatac aattaacaag       60
agaattaact ttatatttgg tgtgattata tttattttg cagtactagt actacgttta      120
ggttatttac aaatcgcaca aggctcacat tataaacaaa ttataaaaaa tgatgaaaac      180
attacagtga atgagtctgt gccaagaggt cgtattttag acagaaatgg gaaagtttta      240
gttgataatg cttctaaaat ggctattaca tatactaggg gtcgaaaaac aacacaatcg      300
gaaatgttgg atacggctga aaagttatca aagctaatca agatggatac taagaaaatt      360
acagaacgtg ataagaaaga tttctggatt cagttgcatc ctaaaaaagc aaaagcaatg      420
atgacaaaag aacaagctat gttagcagat ggaagtatta acaagatcaa atatgataaa      480
caactgttat cgaaaatcgg aaaatcacaa ttagatgaat tgtcttctaa agatttacaa      540
gttttagcta ttttcgaga gatgaatgca ggaacagttt tagatccaca aatgataaaa      600
```

```
aatgaagatg tcagtgaaaa agagtatgca gcagtttctc agcaactttc caaattacca     660
ggtgttaaca cgtctatgga ttgggataga aaatatccat atggcgatac tttaagaggt     720
atattcggag atgtatcgac acctgctgaa ggtattccaa agaattgac agaacattac      780 ttatccaaag gatattcacg caatgatcgt gttggaaaat cttacctaga atatcaatat     840
gaagatgtat tgcgtggtaa gaagaaagaa atgaaataca caacggacaa atctggtaaa     900
gttacatctt cagaagtgtt aaatcctggc gctcgcggtc aagatttgaa attaacgatc     960
gatatagatc ttcaaaaaga agtagaagca ttattagata acaaattaa gaagcttcgc     1020 agtcaaggtg ccaaagatat ggataatgca atgatggttg tacaaaatcc taaaaatgga    1080
gacattcttg cgcttgccgg aaagcagatt aataagagtg gtaaaatgac tgattatgac    1140
attggtacgt ttacttctca atttgcggtt ggatcttctg taaaaggtgg aacattatta    1200
gccggttatc agaataaagc tatcaaagtt ggagaaacaa tggtcgatga accattacat    1260
ttccaaggtg gtttgacaaa acgatcatac ttcaataaaa acgggcatgt aactattaat    1320
gataagcaag ctttgatgca ttcatcaaac gtatatatgt ttaaaacagc attaaaatta    1380 gcggagacc cttattattc tggtatggct ttaccttcag acataagttc acctgcccaa     1440
aagctaagaa gaggattaaa tcaagtaggc ttaggtgtga aaacagggat agatttacca    1500
aatgaaacaa gaggtcaaat cgaaccatta acaaataatc caggtaatta tctagattta    1560
tcaattggtc aatatgatac ctatacacca ttacaattat cacaatatgt ttcaactata    1620
gcgaatgatg ttatagaat acagccacac attggattaa cgattcatga atcaactaat     1680
aaagatgagg ttggtccact caagaagaaa attaatggca ctgtcttgaa caaggttaat    1740
aatactgaaa aggaaatcaa acaaattcaa gaaggattca aaatggcatt taatgataaa    1800
gatggtactg gatatgttag ttttaaagat acagtagtac ctactgctgg taaaacgggt    1860
accgcagaag tgttccaaaa cggagagcca agagttaact ctacttatat aggatacgcg    1920
ccaattgatg atccaaaatt agcgttttca attgtatata caaatcagcc tgtaccacca    1980
ccatggttaa caggtggaga cttaggtaga gatgtaatta actactactt taagcagtta    2040
ggtaaaaatg ataaaaataa agacaaagac aaataa                              2076

<210> SEQ ID NO 40
<211> LENGTH: 1296
<212> TYPE: DNA
<213> ORGANISM: Staphylococcus aureus

<400> SEQUENCE: 40
atgaaaaatt taatatctat tatcatcatt ttatgtttaa cattaagtat tatgcacacca     60 tatgcacaag ctgctaacag tgacgtaacc cctgtacaag cagcaaatca atatggttat    120
gcaggtttgt cggctgcata cgaaccgacg agtgctgtta atgttagtca aactggacaa    180
ttactgtatc aatacaatat cgatactaag tggaatccag cgtctatgac taaattaatg    240
acaatgtact taacattgga agctgtaaat aaggggcagc tttcacttga tgacacagtc    300
acaatgacga acaaagaata tattatgtct acactacctg agttgagtaa tacgaaacta    360
tatcctggac aagtatggac aatcgcagac ctattacaaa ttacagtatc taattctagt    420
aatgccgcgg cattaatttt agctaaagaa gtatcaaaaa acaccagcga tttcgttgat    480
ttaatgaata caaagctaa agctatcgga atgaaaaata cacatttcgt caatccaacg    540
ggtgctgaaa attcagatt acgtacattt gcaccaacaa aatataaaga ccaagaacgt    600
```

-continued

```
actgtaacga ctgctagaga ctacgccatt ttagatttac acgtgattaa agagacacct    660
aaaatattag actttacaaa gcagttagca ccaacaacgc atgcagttac gtattacaca    720
ttcaactttt cattggaagg tgcaaaaatg agtttgcctg gtacagatgg tttaaaaact    780
ggatcaagtg atacagcaaa ttacaaccat acgattacta ctaaacgagg taaatttaga    840
attaatcaag ttatcatggg tgcaggagac tataaaaacc ttggtggcga aagcaacgt     900 aatatgatgg ggaatgcatt aatggaacgt tcatttgatc agtataaata tgtaaaaata    960
ttgcctaaag gtgagcaaag gataaatggt aagaaatatt atgttgaaaa tgatctttac    1020
gatgttttac caagtgattt tagtaaaaaa gattataaac ttgtagtcga agatggtaaa    1080
gtacacgcgg actatccaag agaatttatt aataaagatt atggacctcc aactgtagaa    1140
gttcatcagc caattatcca aaaggcaaat actgttgcta aaagtatgtg gaagaacat    1200 ccattattca ctatcattgg tggtgcatgc ctagtcgctg gattagcact aattgttcat    1260
atgataatca atcgtttatt tagaaaaaga aaataa                              1296
```

<210> SEQ ID NO 41
<211> LENGTH: 500
<212> TYPE: DNA
<213> ORGANISM: Staphylococcus aureus

<400> SEQUENCE: 41

```
tgctcttttt tatattggtt ttaagaattt catatatcat gattactgga cattctaatg     60
gtcaagattt agtcatgaag gcaaatgaaa agtatttagt taagaatgca caacaaccag    120
aacgaggaaa gatatatgat cgtaatggta agtgctagc agaagatgta gaaagatata     180
aacttgttgc agtaatagat aaaaaggcga gtgccaattc taaaaaacct aggcatgtag    240
ttgataaaaa agagactgca aagaaattat ctacagtcat taatatgaag ccagaggaaa    300
ttgaaaagag acttagtcaa aagaaagctt tccaaattga atttggacgc aaaggaacaa    360
atttaacgta tcaggacaaa ttgaaaatag agaaaatgaa tttgcctggt atttcttttat    420 tgcctgaaac agaacgcttt tatccaaatg gcaattttgc atcacactta attggtagag    480
ctcagaaaaa tccggatact                                                500
```

<210> SEQ ID NO 42
<211> LENGTH: 499
<212> TYPE: DNA
<213> ORGANISM: Staphylococcus aureus

<400> SEQUENCE: 42

```
tgctcttttt tatattggtt ttaagaattt catatatcat gattactgga cattctaatg     60
gtcaagattt agtcatgaag gcaaatgaaa agtatttagt taagaatgca caacaaccag    120
aacgaggaaa gatatatgat cgtaatggta agtgctagc agaagatgta gaaagatata     180
aacttgttgc agtaatagat aaaaaggcga gtgccaattc taaaaaacct aggcatgtag    240
ttgataaaaa agagactgca aagaaattat ctacagtcat taatatgaag ccagaggaaa    300
ttgaaaagag acttagtcaa aagaaagctt tccaaattga atttggacgc aaaggaacaa    360
atttaacgta tcaggacaaa ttgaaaatag agaaaatgaa tttgcctggt atttcttttat    420 tgcctgaaac agaacgcttt tatccaaatg gcaattttgc atcacactta attggtagag    480
ctcagaaaaa tccggatac                                                 499
```

<210> SEQ ID NO 43
<211> LENGTH: 500

<212> TYPE: DNA
<213> ORGANISM: Staphylococcus aureus

<400> SEQUENCE: 43

```
tgctcttttt tatattggtt ttaagaattt catatatcat gattactgga cattctaatg    60
gtcaagattt agtcatgaag gcaaatgaga agtatttagt taagaatgca caacaaccag   120
aacgaggaaa gatatatgat cgtaatggta aagtgctagc agaagatgta gaaagatata   180
aacttgttgc agtaatagat aaaaaggcga gtgccaattc taaaaaacct aggcatgtag   240
ttgataaaaa agagactgca aagaaattat ctacagtcat tgatatgaag ccagaggaaa   300
ttgaaaagag acttagtcaa aagaaagcct tccaaattga atttggacgc aaaggaacaa   360
atttaacgta tcaggacaaa ttgaaaatag agaaaatgaa tttgcctggt atttctttat   420
tgcctgaaac agaacgattt tatccaaatg gcaattttgc atcacactta attggtagag   480
ctcagaaaaa tccggatact                                               500
```

<210> SEQ ID NO 44
<211> LENGTH: 500
<212> TYPE: DNA
<213> ORGANISM: Staphylococcus aureus

<400> SEQUENCE: 44

```
acgattatta agattattgg cttcatgatt attgcatttt tcgttgttct tttactaggt    60
atcttattgt ttgcttatta tgcttggaaa gcacctgctt ttaccgaagc taaattacaa   120
gatccgattc ctgcaaagat atatgacaag aacggagaac ttgttaaaac attagataat   180
ggccaaagac atgagcatgt aaatttaaaa gacgtgccga atcaatgaa agacgcagta    240
cttgcaactg aagacaatcg tttctacgaa catggcgcac ttgattataa acgtttattc   300
ggtgcaattg gtaagaactt gactggtgga tttggttctg aaggtgcctc aacattaaca   360
caacaagttg ttaaagatgc attttttatca caacataaat ctattggacg taaagctcaa   420
gaagcatact tatcatatcg tttagaacaa gagtatagta aagatgatat cttccaagta   480
tatctaaaca aaatttacta                                               500
```

<210> SEQ ID NO 45
<211> LENGTH: 500
<212> TYPE: DNA
<213> ORGANISM: Staphylococcus aureus

<400> SEQUENCE: 45

```
acgattatta agattattgg ctttattatt attgcatttt tcgttgttct tttactaggt    60
atcttattgt ttgcttatta tgcttggaaa gcacctgctt ttaccgaagc taaattacaa   120
gatccgattc ctgcatagat atatgacaag aacggagaac ttgttaaaac attagataat   180
ggccaaagac atgagcatgt aactttaaaa gacgtgccga atcaatgaa agacgcagtc    240
cttgcaactg aagacaatcg tttctacgaa catggcgcac ttgattataa acgtttattc   300
ggtgcaattg gtaagaactt gactggtgga tttggatctg aaggtgcctc aacattaaca   360
caacaagatg ttaaagatgc attttttatca caacataaat ctattggacg taaagctcac   420
gaagcatact tatcatatcg tttagaacaa gagtatagta aagatgatat cttccaagta   480
tatctaaaca aaatttacta                                               500
```

<210> SEQ ID NO 46
<211> LENGTH: 500
<212> TYPE: DNA

<213> ORGANISM: Staphylococcus aureus

<400> SEQUENCE: 46

| acgattatta | agattattgg | cttcatgatt | attgcatttt | ttgttgttct | tttactaggt | 60 |
| atcttattgt | ttgcttatta | tgcttggaaa | gcacctgctt | ttaccgaagc | taaattacaa | 120 |
| gatccgattc | ctgcaaagat | atatgacaag | aacggagaac | ttgttaaaac | attagataat | 180 |
| ggccaaagac | atgagcatgt | aaatttaaaa | gacgtgccga | aatcaatgaa | agacgcagta | 240 |
| cttgcaactg | aagacaatcg | tttctacgaa | catggcgcac | ttgattataa | acgtttattc | 300 |
| ggtgcaattg | gtaagaactt | gactggtgga | tttggttctg | aaggtgcctc | aacattaaca | 360 |
| caacaagttg | ttaaagatgc | atttttatca | caacataaat | ctattggacg | taaagctcaa | 420 |
| gaagcatact | tatcatatcg | tttagaacaa | gagtatagta | aagatgatat | cttccaagta | 480 |
| tatctaaata | aaatttacta | | | | | 500 |

<210> SEQ ID NO 47
<211> LENGTH: 231
<212> TYPE: DNA
<213> ORGANISM: Staphylococcus aureus

<400> SEQUENCE: 47

| taactttata | tttggtgtga | ttatatttat | ttttgcagta | ctagtactac | gtttaggtta | 60 |
| tttacaaatc | gcacaaggct | cacattataa | acaaattata | aaaatgatg | aaaacattac | 120 |
| agtgaatgag | tctgtgccaa | gaggtcgtat | tttagacaga | aatgggaaag | ttttagttga | 180 |
| taatgcttct | aaaatggcta | ttacatatac | tagggggtcga | aaaacaacac | a | 231 |

<210> SEQ ID NO 48
<211> LENGTH: 231
<212> TYPE: DNA
<213> ORGANISM: Staphylococcus aureus

<400> SEQUENCE: 48

| taactttata | tttggtgtga | ttgtatttat | ttttgcagta | ctagtactac | gttttggtta | 60 |
| tttacaaatc | gcacaaggct | cacattataa | acaaattata | aaaatgatg | aaaacattac | 120 |
| agtgaatgag | tctgtgccaa | gaggtcgtat | tttagacaga | aatgggaaag | ttttagttga | 180 |
| taatgcttct | aaaatggcta | ttacatatac | tagggggtcga | aaaacaacac | a | 231 |

<210> SEQ ID NO 49
<211> LENGTH: 229
<212> TYPE: DNA
<213> ORGANISM: Staphylococcus aureus

<400> SEQUENCE: 49

| taactttat | ttggtgtgat | tgtatttatt | tttgcagtac | tagtactacg | tttaggttat | 60 |
| ttacaaatcg | cacaaggctc | acattataaa | caaattataa | aaatgatga | aaacattaca | 120 |
| gtgaatgagt | ctgtgccaag | aggtcgtatt | ttagacagaa | atgggaaagt | tttagttgat | 180 |
| aatgcttcta | aaatggctat | tacatatact | aggggtcgaa | aacaacaa | | 229 |

<210> SEQ ID NO 50
<211> LENGTH: 500
<212> TYPE: DNA
<213> ORGANISM: Staphylococcus aureus

<400> SEQUENCE: 50

| tggttatgca | ggtttgtcgg | ctgcatacga | accgacgagt | gctgttaatg | taagtcaaac | 60 |

```
tggacaatta ctgtatcaat acaatatcga tactaagtgg aatccagcgt ctatgactaa    120
attaatgaca atgtacttaa cattggaagc tgtcaataag gggcagcttt cacttgatga    180
cacagtcaca atgacgaaca aagaatatat tatgtctaca ctacctgagt tgagtaatac    240
gaaactatat cctggacaag tatggacaat cgcagaccta ttacaaatta cagtatctaa    300
ttctagtaat gccgcggcat taattttagc taagaaggta ttcaaaaaac accagcgatt    360
tcgttgattt aatgaataac aaagctaaag ctatcggaat gaaaaataca catttcgtca    420
atccaacggg tgctgaaaat tcaagattac gtacatttgc accaacaaag tataaagacc    480
aagaacgtac tgtaacgact                                                500
```

<210> SEQ ID NO 51
<211> LENGTH: 500
<212> TYPE: DNA
<213> ORGANISM: Staphylococcus aureus

<400> SEQUENCE: 51

```
tggttatgca ggtttgtcgg ctgcatacga accgacgagt gctgttaatg ttagtcaaac     60
tggacaatta ctgtatcaat acaatatcga tactaagtgg aatccagcgt ctatgactaa    120
attaatgaca atgtacttaa cattggaagc tgtaaataag gggcagcttt cacttgatga    180
cacagtcaca atgacgaaca aagaatatat tatgtctaca ctacctgagt tgagtaatac    240
gaaactatat cctggacaag tatggacaat cgcagaccta ttacaaatta cagtatctaa    300
ttctagtaat gccgcggcat taattttagc taagaaggta ttcaaaaaac accagcgatt    360
tcgttgattt aatgaataac aaagctaaag ctatcggaat gaaaaataca catttcgtca    420
atccaacggg tgctgaaaat tcaagattac gtacatttgc accaacaaaa tataaagacc    480
aagaacgtac tgtaacgact                                                500
```

<210> SEQ ID NO 52
<211> LENGTH: 500
<212> TYPE: DNA
<213> ORGANISM: Staphylococcus aureus

<400> SEQUENCE: 52

```
tggttatgca ggtttgtcgg ctgcatacga accgacgagt gctgttaatg ttagtcaaac     60
tggacaatta ctgtatcaat acaatatcga tactaagtgg aatccagcgt ctatgactaa    120
attaatgaca atgtacttaa cattggaagc tgtaaataag gggcagcttt cacttgatga    180
cacagtcaca atgacgaaca aagaatatat tatgtctaca ctacctgagt tgagtaatac    240
gaaactatat cctggacaag tatggacaat cgcagaccta ttacaaatta cagtatctaa    300
ttctagtaat gccgcggcat taattttagc taagaaggta ttcaaaaaac accagcgatt    360
tcgttgattt aatgaataac aaagctaaag ctatcggaat gaaaaataca catttcgtca    420
atccaacggg tgctgaaaat tcaagattac gtacatttgc accaacaaaa tataaagacc    480
aagaacgtac tgtaacgact                                                500
```

<210> SEQ ID NO 53
<211> LENGTH: 44
<212> TYPE: DNA
<213> ORGANISM: Staphylococcus aureus

<400> SEQUENCE: 53

```
tttggtgtga ttgtatttat ttttgcagta ctagtactac gttt                      44
```

```
<210> SEQ ID NO 54
<211> LENGTH: 44
<212> TYPE: DNA
<213> ORGANISM: Staphylococcus aureus

<400> SEQUENCE: 54
tttggtgtga ttgtatttat ttttgcagta ctagtactac gttt            44

<210> SEQ ID NO 55
<211> LENGTH: 44
<212> TYPE: DNA
<213> ORGANISM: Staphylococcus aureus

<400> SEQUENCE: 55
tttggtgtga ttgtatttat ttttgcagta ctagtactac gttt            44

<210> SEQ ID NO 56
<211> LENGTH: 44
<212> TYPE: DNA
<213> ORGANISM: Staphylococcus aureus

<400> SEQUENCE: 56
tttggtgtga ttgtatttat ttttgcagta ctagtactac gttt            44

<210> SEQ ID NO 57
<211> LENGTH: 44
<212> TYPE: DNA
<213> ORGANISM: Staphylococcus aureus

<400> SEQUENCE: 57
tttggtgtga ttgtatttat ttttgcagta ctagtactac gttt            44

<210> SEQ ID NO 58
<211> LENGTH: 43
<212> TYPE: DNA
<213> ORGANISM: Staphylococcus aureus

<400> SEQUENCE: 58
gttgctgtga ttgatttatt tttgctgctc tcgaactacg ttt             43

<210> SEQ ID NO 59
<211> LENGTH: 44
<212> TYPE: DNA
<213> ORGANISM: Staphylococcus aureus

<400> SEQUENCE: 59
tttggtgtga ttatatttat ttttgcagta ctagtactac gttt            44

<210> SEQ ID NO 60
<211> LENGTH: 44
<212> TYPE: DNA
<213> ORGANISM: Staphylococcus aureus

<400> SEQUENCE: 60
tttggtgtga ttatatttat ttttgcagta ctagtactac gttt            44

<210> SEQ ID NO 61
<211> LENGTH: 44
<212> TYPE: DNA
<213> ORGANISM: Staphylococcus aureus

<400> SEQUENCE: 61
tttggtgtga ttatatttat ttttgcagta ctagtactac gttt            44
```

<210> SEQ ID NO 62
<211> LENGTH: 44
<212> TYPE: DNA
<213> ORGANISM: Staphylococcus aureus

<400> SEQUENCE: 62
tttggtgtga ttatatttat ttttgcagta ctagtactac gttt                    44

<210> SEQ ID NO 63
<211> LENGTH: 44
<212> TYPE: DNA
<213> ORGANISM: Staphylococcus aureus

<400> SEQUENCE: 63
tttggtgtga ttatatttat ttttgcagta ctagtactac gttt                    44

<210> SEQ ID NO 64
<211> LENGTH: 44
<212> TYPE: DNA
<213> ORGANISM: Staphylococcus aureus

<400> SEQUENCE: 64
tttggtgtga ttatatttat ttttgcagta ctagtactac gttt                    44

<210> SEQ ID NO 65
<211> LENGTH: 44
<212> TYPE: DNA
<213> ORGANISM: Staphylococcus aureus

<400> SEQUENCE: 65
tttggtgtga ttatatttat ttttgcagta ctagtactac gttt                    44

<210> SEQ ID NO 66
<211> LENGTH: 44
<212> TYPE: DNA
<213> ORGANISM: Staphylococcus aureus

<400> SEQUENCE: 66
tttggtgtga ttatatttat ttttgcagta ctagtactac gttt                    44

<210> SEQ ID NO 67
<211> LENGTH: 44
<212> TYPE: DNA
<213> ORGANISM: Staphylococcus aureus

<400> SEQUENCE: 67
tttggtgtga ttatattaat ttttgcagta ctagtactac gttt                    44

<210> SEQ ID NO 68
<211> LENGTH: 44
<212> TYPE: DNA
<213> ORGANISM: Staphylococcus aureus

<400> SEQUENCE: 68
tttggtgtga ttatatttat ttttgcagta ctagtactac gttt                    44

<210> SEQ ID NO 69
<211> LENGTH: 44
<212> TYPE: DNA
<213> ORGANISM: Staphylococcus aureus

<400> SEQUENCE: 69
tttggtgtga ttatatttat ttttgcagta ctagtactac gttt                    44

<210> SEQ ID NO 70
<211> LENGTH: 44
<212> TYPE: DNA
<213> ORGANISM: Staphylococcus aureus

<400> SEQUENCE: 70
tttggtgtga ttatatttat ttttgcagta ctagtactac gttt                    44

<210> SEQ ID NO 71
<211> LENGTH: 44
<212> TYPE: DNA
<213> ORGANISM: Staphylococcus aureus

<400> SEQUENCE: 71
tttggtgtga ttatatttat ttttgcagta ctagtactac gttt                    44

<210> SEQ ID NO 72
<211> LENGTH: 44
<212> TYPE: DNA
<213> ORGANISM: Staphylococcus aureus

<400> SEQUENCE: 72
tttggtgtga ttatatttat ttttgcagta ctagtactac gttt                    44

<210> SEQ ID NO 73
<211> LENGTH: 44
<212> TYPE: DNA
<213> ORGANISM: Staphylococcus aureus

<400> SEQUENCE: 73
tttggtgtga ttatatttat ttttgcagta ctagtactac gttt                    44

<210> SEQ ID NO 74
<211> LENGTH: 44
<212> TYPE: DNA
<213> ORGANISM: Staphylococcus aureus

<400> SEQUENCE: 74
tttggtgtga ttatatttat ttttgcagta ctagtactac gttt                    44

<210> SEQ ID NO 75
<211> LENGTH: 44
<212> TYPE: DNA
<213> ORGANISM: Staphylococcus aureus

<400> SEQUENCE: 75
tttggtgtga ttatatttat ttttgcagta ctagtactac gttt                    44

<210> SEQ ID NO 76
<211> LENGTH: 44
<212> TYPE: DNA
<213> ORGANISM: Staphylococcus aureus

<400> SEQUENCE: 76
tttggtgtga ttatatttat ttttgcagta ctagtactac gttt                    44

<210> SEQ ID NO 77
<211> LENGTH: 44
<212> TYPE: DNA
<213> ORGANISM: Staphylococcus aureus

<400> SEQUENCE: 77
tttggtgtga ttatatttat ttttgcagta ctagtactac gttt          44

<210> SEQ ID NO 78
<211> LENGTH: 44
<212> TYPE: DNA
<213> ORGANISM: Staphylococcus aureus

<400> SEQUENCE: 78
tttggtgtga ttatatttat ttttgcagta ctagtactac gttt          44

<210> SEQ ID NO 79
<211> LENGTH: 44
<212> TYPE: DNA
<213> ORGANISM: Staphylococcus aureus

<400> SEQUENCE: 79
tttggtgtga ttatatttat ttttgcagta ctagtactac gttt          44

<210> SEQ ID NO 80
<211> LENGTH: 44
<212> TYPE: DNA
<213> ORGANISM: Staphylococcus aureus

<400> SEQUENCE: 80
tttggtgtga ttatatttat ttttgcagta ctagtactac gttt          44

<210> SEQ ID NO 81
<211> LENGTH: 44
<212> TYPE: DNA
<213> ORGANISM: Staphylococcus aureus

<400> SEQUENCE: 81
tttggtgtga ttatatttat ttttgcagta ctagtactac gttt          44

<210> SEQ ID NO 82
<211> LENGTH: 44
<212> TYPE: DNA
<213> ORGANISM: Staphylococcus aureus

<400> SEQUENCE: 82
tttggtgtga ttatatttat ttttgcagta ctagtactac gttt          44

<210> SEQ ID NO 83
<211> LENGTH: 44
<212> TYPE: DNA
<213> ORGANISM: Staphylococcus aureus

<400> SEQUENCE: 83
tttggtgtga ttatatttat ttttgcagta ctagtactac gttt          44

<210> SEQ ID NO 84
<211> LENGTH: 44
<212> TYPE: DNA
<213> ORGANISM: Staphylococcus aureus

<400> SEQUENCE: 84
tttggtgtga ttatatttat ttttgctgta ctagtactac gttt          44

<210> SEQ ID NO 85
<211> LENGTH: 42
<212> TYPE: DNA
<213> ORGANISM: Staphylococcus aureus

<400> SEQUENCE: 85
tggtgagata atatttattt ttgcagtact agtactacgt tt    42

<210> SEQ ID NO 86
<211> LENGTH: 42
<212> TYPE: DNA
<213> ORGANISM: Staphylococcus aureus

<400> SEQUENCE: 86
tttggtgtga ttatatttat ttttgcagct agtactacgt tt    42

<210> SEQ ID NO 87
<211> LENGTH: 44
<212> TYPE: DNA
<213> ORGANISM: Staphylococcus aureus

<400> SEQUENCE: 87
tttggtgtga ttatatttat ttttgcagta ctagtactac gttt    44

<210> SEQ ID NO 88
<211> LENGTH: 44
<212> TYPE: DNA
<213> ORGANISM: Staphylococcus aureus

<400> SEQUENCE: 88
tttggtgaga ttatatttat ttttgcagta ctagtactac gttt    44

<210> SEQ ID NO 89
<211> LENGTH: 44
<212> TYPE: DNA
<213> ORGANISM: Staphylococcus aureus

<400> SEQUENCE: 89
tttggtgtga ttatatttat ttttgcagta ctagtactac gttt    44

<210> SEQ ID NO 90
<211> LENGTH: 44
<212> TYPE: DNA
<213> ORGANISM: Staphylococcus aureus

<400> SEQUENCE: 90
tttggtgtga ttatatttat ttttgcagta ctagtactac gttt    44

<210> SEQ ID NO 91
<211> LENGTH: 44
<212> TYPE: DNA
<213> ORGANISM: Staphylococcus aureus

<400> SEQUENCE: 91
tttggtgtga ttatatttat ttttgcagta ctagtactac gttt    44

<210> SEQ ID NO 92
<211> LENGTH: 44
<212> TYPE: DNA
<213> ORGANISM: Staphylococcus aureus

<400> SEQUENCE: 92
tttggtgtga ttatatttat ttttgcagta ctagtactac gttt    44

<210> SEQ ID NO 93
<211> LENGTH: 44
<212> TYPE: DNA
<213> ORGANISM: Staphylococcus aureus

<400> SEQUENCE: 93
tttggtgtga ttatatttat ttttgcagta ctagtactac gttt    44

<210> SEQ ID NO 94
<211> LENGTH: 44
<212> TYPE: DNA
<213> ORGANISM: Staphylococcus aureus

<400> SEQUENCE: 94
gttgctgtga taatatttat ttttgctgta cgtcgaacta cgtt    44

<210> SEQ ID NO 95
<211> LENGTH: 44
<212> TYPE: DNA
<213> ORGANISM: Staphylococcus aureus

<400> SEQUENCE: 95
tttggtgtga ttatatttat ttttgcagta ctagtactac gttt    44

<210> SEQ ID NO 96
<211> LENGTH: 44
<212> TYPE: DNA
<213> ORGANISM: Staphylococcus aureus

<400> SEQUENCE: 96
tttggtgtga ttatatttat ttttgcagta ctagtactac gttt    44

<210> SEQ ID NO 97
<211> LENGTH: 44
<212> TYPE: DNA
<213> ORGANISM: Staphylococcus aureus

<400> SEQUENCE: 97
tttggtgtga ttatatttat ttttgcagta ctagtactac gttt    44

<210> SEQ ID NO 98
<211> LENGTH: 44
<212> TYPE: DNA
<213> ORGANISM: Staphylococcus aureus

<400> SEQUENCE: 98
tttggtgtga ttgtatttat ttttgcagta ctagtactac gttt    44

<210> SEQ ID NO 99
<211> LENGTH: 44
<212> TYPE: DNA
<213> ORGANISM: Staphylococcus aureus

<400> SEQUENCE: 99
tttggtgtga ttgtatttat ttttgcagta ctagtactac gttt    44

<210> SEQ ID NO 100
<211> LENGTH: 44
<212> TYPE: DNA
<213> ORGANISM: Staphylococcus aureus

<400> SEQUENCE: 100
tttggtgtga ttgtatttat ttttgcagta ctagtactac gttt    44

<210> SEQ ID NO 101
<211> LENGTH: 44
<212> TYPE: DNA

<210> SEQ ID NO 101
<211> LENGTH: 44
<212> TYPE: DNA
<213> ORGANISM: Staphylococcus aureus

<400> SEQUENCE: 101
tttggtgtga ttgtatttat ttttgcagta ctagtactac gttt       44

<210> SEQ ID NO 102
<211> LENGTH: 44
<212> TYPE: DNA
<213> ORGANISM: Staphylococcus aureus

<400> SEQUENCE: 102
tttggtgtga ttgccgtatc ttttgcagtt ctagtactac gttt       44

<210> SEQ ID NO 103
<211> LENGTH: 44
<212> TYPE: DNA
<213> ORGANISM: Staphylococcus aureus

<400> SEQUENCE: 103
tttggtgtga ttgtatttat ttttgcagta ctagtactac gttt       44

<210> SEQ ID NO 104
<211> LENGTH: 36
<212> TYPE: DNA
<213> ORGANISM: Staphylococcus aureus

<400> SEQUENCE: 104
gattgtattc ttttagtagc tgagatgaca aacact       36

<210> SEQ ID NO 105
<211> LENGTH: 44
<212> TYPE: DNA
<213> ORGANISM: Staphylococcus aureus

<400> SEQUENCE: 105
tttggtgtga ttgtaaaaat tttgcagttg tagtactacg ttta       44

<210> SEQ ID NO 106
<211> LENGTH: 691
<212> TYPE: PRT
<213> ORGANISM: Staphylococcus aureus

<400> SEQUENCE: 106

Met Leu Lys Arg Leu Lys Glu Lys Ser Asn Asp Glu Ile Val Gln Asn
1               5                   10                  15

Thr Ile Asn Lys Arg Ile Asn Phe Ile Phe Gly Val Ile Val Phe Ile
            20                  25                  30

Phe Ala Val Leu Val Leu Arg Leu Gly Tyr Leu Gln Ile Ala Gln Gly
        35                  40                  45

Ser His Tyr Lys Gln Ile Ile Lys Asn Asp Glu Asn Ile Thr Val Asn
    50                  55                  60

Glu Ser Val Pro Arg Gly Arg Ile Leu Asp Arg Asn Gly Lys Val Leu
65                  70                  75                  80

Val Asp Asn Ala Ser Lys Met Ala Ile Thr Tyr Thr Arg Gly Arg Lys
                85                  90                  95

Thr Thr Gln Ser Glu Met Leu Asp Thr Ala Glu Lys Leu Ser Lys Leu
            100                 105                 110

Ile Lys Met Asp Thr Lys Lys Ile Thr Glu Arg Asp Lys Lys Asp Phe
        115                 120                 125

Trp Ile Gln Leu His Pro Lys Lys Ala Lys Ala Met Met Thr Lys Glu

```
            130                 135                 140
Gln Ala Met Leu Ala Asp Gly Ser Ile Lys Gln Asp Gln Tyr Asp Lys
145                 150                 155                 160

Gln Leu Leu Ser Lys Ile Gly Lys Ser Gln Leu Asp Glu Leu Ser Ser
                165                 170                 175

Lys Asp Leu Gln Val Leu Ala Ile Phe Arg Glu Met Asn Ala Gly Thr
            180                 185                 190

Val Leu Asp Pro Gln Met Ile Lys Asn Glu Asp Val Ser Glu Lys Glu
        195                 200                 205

Tyr Ala Ala Val Ser Gln Gln Leu Ser Lys Leu Pro Gly Val Asn Thr
210                 215                 220

Ser Met Asp Trp Asp Arg Lys Tyr Pro Tyr Gly Asp Thr Leu Arg Gly
225                 230                 235                 240

Ile Phe Gly Asp Val Ser Thr Pro Ala Glu Gly Ile Pro Lys Glu Leu
                245                 250                 255

Thr Glu His Tyr Leu Ser Lys Gly Tyr Ser Arg Asn Asp Arg Val Gly
            260                 265                 270

Lys Ser Tyr Leu Glu Tyr Gln Tyr Glu Asp Val Leu Arg Gly Lys Lys
        275                 280                 285

Lys Glu Met Lys Tyr Thr Thr Asp Lys Ser Gly Lys Val Thr Ser Ser
290                 295                 300

Glu Val Leu Asn Pro Gly Ala Arg Gly Gln Asp Leu Lys Leu Thr Ile
305                 310                 315                 320

Asp Ile Asp Leu Gln Lys Glu Val Glu Ala Leu Leu Asp Lys Gln Ile
                325                 330                 335

Lys Lys Leu Arg Ser Gln Gly Ala Lys Asp Met Asp Asn Ala Met Met
            340                 345                 350

Val Val Gln Asn Pro Lys Asn Gly Asp Ile Leu Ala Leu Ala Gly Lys
        355                 360                 365

Gln Ile Asn Lys Ser Gly Lys Met Thr Asp Tyr Asp Ile Gly Thr Phe
370                 375                 380

Thr Ser Gln Phe Ala Val Gly Ser Ser Val Lys Gly Gly Thr Leu Leu
385                 390                 395                 400

Ala Gly Tyr Gln Asn Lys Ala Ile Lys Val Gly Glu Thr Met Val Asp
                405                 410                 415

Glu Pro Leu His Phe Gln Gly Gly Leu Thr Lys Arg Ser Tyr Phe Asn
            420                 425                 430

Lys Asn Gly His Val Thr Ile Asn Asp Lys Gln Ala Leu Met His Ser
        435                 440                 445

Ser Asn Val Tyr Met Phe Lys Thr Ala Leu Lys Leu Ala Gly Asp Pro
450                 455                 460

Tyr Tyr Ser Gly Met Ala Leu Pro Ser Asp Ile Ser Ser Pro Ala Gln
465                 470                 475                 480

Lys Leu Arg Arg Gly Leu Asn Gln Val Gly Leu Gly Val Lys Thr Gly
                485                 490                 495

Ile Asp Leu Pro Asn Glu Thr Arg Gly Gln Ile Glu Pro Leu Thr Asn
            500                 505                 510

Asn Pro Gly Asn Tyr Leu Asp Leu Ser Ile Gly Gln Tyr Asp Thr Tyr
        515                 520                 525

Thr Pro Leu Gln Leu Ser Gln Tyr Val Ser Thr Ile Ala Asn Asp Gly
530                 535                 540

Tyr Arg Ile Gln Pro His Ile Gly Leu Thr Ile His Glu Ser Thr Asn
545                 550                 555                 560
```

```
Lys Asp Glu Val Gly Pro Leu Lys Lys Ile Asn Gly Thr Val Leu
            565                 570                 575

Asn Lys Val Asn Asn Thr Glu Lys Glu Ile Lys Gln Ile Gln Glu Gly
        580                 585                 590

Phe Lys Met Ala Phe Asn Asp Lys Asp Gly Thr Gly Tyr Val Ser Phe
            595                 600                 605

Lys Asp Thr Val Val Pro Thr Ala Gly Lys Thr Gly Thr Ala Glu Val
            610                 615                 620

Phe Gln Asn Gly Glu Pro Arg Val Asn Ser Thr Tyr Ile Gly Tyr Ala
625                 630                 635                 640

Pro Ile Asp Asp Pro Lys Leu Ala Phe Ser Ile Val Tyr Thr Asn Gln
            645                 650                 655

Pro Val Pro Pro Pro Trp Leu Thr Gly Gly Asp Leu Gly Arg Asp Val
            660                 665                 670

Ile Asn Tyr Tyr Phe Lys Gln Leu Gly Lys Asp Asp Lys Asn Lys Asp
            675                 680                 685

Lys Asp Lys
    690

<210> SEQ ID NO 107
<211> LENGTH: 691
<212> TYPE: PRT
<213> ORGANISM: Staphylococcus aureus

<400> SEQUENCE: 107

Met Leu Lys Arg Leu Lys Glu Lys Ser Asn Asp Glu Ile Val Gln Asn
1               5                   10                  15

Thr Ile Asn Lys Arg Ile Asn Phe Ile Phe Gly Val Ile Ile Phe Ile
            20                  25                  30

Phe Ala Val Leu Val Leu Arg Leu Gly Tyr Leu Gln Ile Ala Gln Gly
        35                  40                  45

Ser His Tyr Lys Gln Ile Ile Lys Asn Asp Glu Asn Ile Thr Val Asn
    50                  55                  60

Glu Ser Val Pro Arg Gly Arg Ile Leu Asp Arg Asn Gly Lys Val Leu
65                  70                  75                  80

Val Asp Asn Ala Ser Lys Met Ala Ile Thr Tyr Thr Arg Gly Arg Lys
                85                  90                  95

Thr Thr Gln Ser Glu Met Leu Asp Thr Ala Glu Lys Leu Ser Lys Leu
            100                 105                 110

Ile Lys Met Asp Thr Lys Lys Ile Thr Glu Arg Asp Lys Lys Asp Phe
        115                 120                 125

Trp Ile Gln Leu His Pro Lys Lys Ala Lys Ala Met Met Thr Lys Glu
    130                 135                 140

Gln Ala Met Leu Ala Asp Gly Ser Ile Lys Gln Asp Gln Tyr Asp Lys
145                 150                 155                 160

Gln Leu Leu Ser Lys Ile Gly Lys Ser Gln Leu Asp Glu Leu Ser Ser
                165                 170                 175

Lys Asp Leu Gln Val Leu Ala Ile Phe Arg Glu Met Asn Ala Gly Thr
            180                 185                 190

Val Leu Asp Pro Gln Met Ile Lys Asn Glu Asp Val Ser Glu Lys Glu
        195                 200                 205

Tyr Ala Ala Val Ser Gln Gln Leu Ser Lys Leu Pro Gly Val Asn Thr
    210                 215                 220

Ser Met Asp Trp Asp Arg Lys Tyr Pro Tyr Gly Asp Thr Leu Arg Gly
```

```
             225                 230                 235                 240

Ile Phe Gly Asp Val Ser Thr Pro Ala Glu Gly Ile Pro Lys Glu Leu
                        245                 250                 255

Thr Glu His Tyr Leu Ser Lys Gly Tyr Ser Arg Asn Asp Arg Val Gly
                        260                 265                 270

Lys Ser Tyr Leu Glu Tyr Gln Tyr Glu Asp Val Leu Arg Gly Lys Lys
                        275                 280                 285

Lys Glu Met Lys Tyr Thr Thr Asp Lys Ser Gly Lys Val Thr Ser Ser
                        290                 295                 300

Glu Val Leu Asn Pro Gly Ala Arg Gly Gln Asp Leu Lys Leu Thr Ile
        305                 310                 315                 320

Asp Ile Asp Leu Gln Lys Glu Val Glu Ala Leu Leu Asp Lys Gln Ile
                        325                 330                 335

Lys Lys Leu Arg Ser Gln Gly Ala Lys Asp Met Asp Asn Ala Met Met
                        340                 345                 350

Val Val Gln Asn Pro Lys Asn Gly Asp Ile Leu Ala Leu Ala Gly Lys
                        355                 360                 365

Gln Ile Asn Lys Ser Gly Lys Met Thr Asp Tyr Asp Ile Gly Thr Phe
                        370                 375                 380

Thr Ser Gln Phe Ala Val Gly Ser Ser Val Lys Gly Gly Thr Leu Leu
        385                 390                 395                 400

Ala Gly Tyr Gln Asn Lys Ala Ile Lys Val Gly Glu Thr Met Val Asp
                        405                 410                 415

Glu Pro Leu His Phe Gln Gly Gly Leu Thr Lys Arg Ser Tyr Phe Asn
                        420                 425                 430

Lys Asn Gly His Val Thr Ile Asn Asp Lys Gln Ala Leu Met His Ser
                        435                 440                 445

Ser Asn Val Tyr Met Phe Lys Thr Ala Leu Lys Leu Ala Gly Asp Pro
                        450                 455                 460

Tyr Tyr Ser Gly Met Ala Leu Pro Ser Asp Ile Ser Ser Pro Ala Gln
        465                 470                 475                 480

Lys Leu Arg Arg Gly Leu Asn Gln Val Gly Leu Gly Val Lys Thr Gly
                        485                 490                 495

Ile Asp Leu Pro Asn Glu Thr Arg Gly Gln Ile Glu Pro Leu Thr Asn
                        500                 505                 510

Asn Pro Gly Asn Tyr Leu Asp Leu Ser Ile Gly Gln Tyr Asp Thr Tyr
                        515                 520                 525

Thr Pro Leu Gln Leu Ser Gln Tyr Val Ser Thr Ile Ala Asn Asp Gly
                        530                 535                 540

Tyr Arg Ile Gln Pro His Ile Gly Leu Thr Ile His Glu Ser Thr Asn
        545                 550                 555                 560

Lys Asp Glu Val Gly Pro Leu Lys Lys Lys Ile Asn Gly Thr Val Leu
                        565                 570                 575

Asn Lys Val Asn Asn Thr Glu Lys Glu Ile Lys Gln Ile Gln Glu Gly
                        580                 585                 590

Phe Lys Met Ala Phe Asn Asp Lys Asp Gly Thr Gly Tyr Val Ser Phe
                        595                 600                 605

Lys Asp Thr Val Val Pro Thr Ala Gly Lys Thr Gly Thr Ala Glu Val
                        610                 615                 620

Phe Gln Asn Gly Glu Pro Arg Val Asn Ser Thr Tyr Ile Gly Tyr Ala
        625                 630                 635                 640

Pro Ile Asp Asp Pro Lys Leu Ala Phe Ser Ile Val Tyr Thr Asn Gln
                        645                 650                 655
```

```
Pro Val Pro Pro Pro Trp Leu Thr Gly Gly Asp Leu Gly Arg Asp Val
            660                 665                 670

Ile Asn Tyr Tyr Phe Lys Gln Leu Gly Lys Asn Asp Lys Asn Lys Asp
        675                 680                 685

Lys Asp Lys
    690

<210> SEQ ID NO 108
<211> LENGTH: 691
<212> TYPE: PRT
<213> ORGANISM: Staphylococcus aureus

<400> SEQUENCE: 108

Met Leu Lys Arg Leu Lys Glu Lys Ser Asn Asp Glu Ile Val Gln Asn
1               5                   10                  15

Thr Ile Asn Lys Arg Ile Asn Phe Ile Phe Gly Val Ile Val Phe Ile
            20                  25                  30

Phe Ala Val Leu Val Leu Arg Leu Gly Tyr Leu Gln Ile Ala Gln Gly
        35                  40                  45

Ser His Tyr Lys Gln Ile Ile Lys Asn Asp Glu Asn Ile Thr Val Asn
    50                  55                  60

Glu Ser Val Pro Arg Gly Arg Ile Leu Asp Arg Asn Gly Lys Val Leu
65                  70                  75                  80

Val Asp Asn Ala Ser Lys Met Ala Ile Thr Tyr Thr Arg Gly Arg Lys
                85                  90                  95

Thr Thr Gln Ser Glu Met Leu Asp Thr Ala Glu Lys Leu Ser Lys Leu
            100                 105                 110

Ile Lys Met Asp Thr Lys Lys Ile Thr Glu Arg Asp Lys Lys Asp Phe
        115                 120                 125

Trp Ile Gln Leu His Pro Lys Lys Ala Lys Ala Met Met Thr Lys Glu
    130                 135                 140

Gln Ala Met Leu Ala Asp Gly Ser Ile Lys Gln Asp Gln Tyr Asp Lys
145                 150                 155                 160

Gln Leu Leu Ser Lys Ile Arg Lys Ser Gln Leu Asp Glu Leu Ser Ser
                165                 170                 175

Lys Asp Leu Gln Val Leu Ala Ile Phe Arg Glu Met Asn Ala Gly Thr
            180                 185                 190

Val Leu Asp Pro Gln Met Ile Lys Asn Glu Asp Val Ser Glu Lys Glu
        195                 200                 205

Tyr Ala Ala Val Ser Gln Gln Leu Ser Lys Leu Pro Gly Val Asn Thr
    210                 215                 220

Ser Met Asp Trp Asp Arg Lys Tyr Pro Tyr Gly Asp Thr Leu Arg Gly
225                 230                 235                 240

Ile Phe Gly Asp Val Ser Thr Pro Ala Glu Gly Ile Pro Lys Glu Leu
                245                 250                 255

Thr Glu His Tyr Leu Ser Lys Gly Tyr Ser Arg Asn Asp Arg Val Gly
            260                 265                 270

Lys Ser Tyr Leu Glu Tyr Gln Tyr Glu Asp Val Leu Arg Gly Lys Lys
        275                 280                 285

Lys Glu Met Lys Tyr Thr Thr Asp Lys Ser Gly Lys Val Thr Ser Ser
    290                 295                 300

Glu Val Leu Asn Pro Gly Ala Arg Gly Gln Asp Leu Lys Leu Thr Ile
305                 310                 315                 320

Asp Ile Asp Leu Gln Lys Glu Val Glu Ala Leu Leu Asp Lys Gln Ile
```

```
                    325                 330                 335
Lys Lys Leu Arg Ser Gln Gly Ala Lys Asp Met Asp Asn Ala Met Met
                340                 345                 350
Val Val Gln Asn Pro Lys Asn Gly Asp Ile Leu Ala Leu Ala Gly Lys
                355                 360                 365
Gln Ile Asn Lys Ser Gly Lys Met Thr Asp Tyr Asp Ile Gly Thr Phe
            370                 375                 380
Thr Ser Gln Phe Ala Val Gly Ser Ser Val Lys Gly Thr Leu Leu
385                 390                 395                 400
Ala Gly Tyr Gln Asn Lys Ala Ile Lys Val Gly Glu Thr Met Val Asp
                405                 410                 415
Glu Pro Leu His Phe Gln Gly Gly Leu Thr Lys Arg Ser Tyr Phe Asn
                420                 425                 430
Lys Asn Gly His Val Ser Ile Asn Asp Lys Gln Ala Leu Met His Ser
                435                 440                 445
Ser Asn Val Tyr Met Phe Lys Thr Ala Leu Lys Leu Ala Gly Asp Pro
450                 455                 460
Tyr Tyr Ser Gly Met Ala Leu Pro Ser Asp Ile Ser Ser Pro Ala Gln
465                 470                 475                 480
Lys Leu Arg Arg Gly Leu Asn Gln Val Gly Leu Gly Val Lys Thr Gly
                485                 490                 495
Ile Asp Leu Pro Asn Glu Thr Arg Gly Gln Ile Glu Pro Leu Thr Asn
                500                 505                 510
Asn Pro Gly Asn Tyr Leu Asp Leu Ser Ile Gly Gln Tyr Asp Thr Tyr
            515                 520                 525
Thr Pro Leu Gln Leu Ser Gln Tyr Val Ser Thr Ile Ala Asn Asp Gly
            530                 535                 540
Tyr Arg Ile Gln Pro His Ile Gly Leu Thr Ile His Glu Ser Thr Asn
545                 550                 555                 560
Lys Asp Glu Val Gly Pro Leu Lys Lys Lys Ile Asn Gly Thr Val Leu
                565                 570                 575
Asn Lys Val Asn Asn Thr Glu Lys Glu Ile Lys Gln Ile Gln Glu Gly
                580                 585                 590
Phe Lys Met Ala Phe Asn Asp Lys Asp Gly Thr Gly Tyr Val Ser Phe
            595                 600                 605
Lys Asp Thr Val Val Pro Thr Ala Gly Lys Thr Gly Thr Ala Glu Val
            610                 615                 620
Phe Gln Asn Gly Glu Pro Arg Val Asn Ser Thr Tyr Ile Gly Tyr Val
625                 630                 635                 640
Pro Ile Asp Asp Pro Lys Leu Ala Phe Ser Ile Val Tyr Thr Asn Gln
                645                 650                 655
Pro Val Pro Pro Pro Trp Leu Thr Gly Gly Asp Leu Gly Arg Asp Val
                660                 665                 670
Ile Asn Tyr Tyr Phe Lys Gln Leu Gly Lys Asp Asp Lys Asn Lys Asp
                675                 680                 685
Lys Asp Lys
    690

<210> SEQ ID NO 109
<211> LENGTH: 2076
<212> TYPE: DNA
<213> ORGANISM: Staphylococcus aureus

<400> SEQUENCE: 109
```

```
ttgttaaaaa gactaaaaga aaaatcaaat gatgaaatcg ttcaaaatac aattaacaag      60
agaattaact ttatatttgg tgtgattgta tttattttg cagtactagt actacgttta     120
ggttatttac aaatcgcaca aggctcacat tataaacaaa ttataaaaaa tgatgaaaac     180
attacagtga atgagtctgt gccaagaggt cgtattttag acagaaatgg aaagtttta      240 gttgataatg cttctaaaat ggctattaca tatactaggg gtcgaaaaac aacacaatcg     300
gaaatgttgg atacggctga aaagttatca aagctaatca agatggatac taagaaaatt     360
acagaacgtg ataagaaaga tttctggatt cagttgcatc ctaaaaaagc aaaagcaatg     420
atgacaaaag aacaagctat gttagcagat ggaagtatta acaagatca  atatgataaa     480 caactgttat cgaaaatcgg aaaatcacaa ttagatgaat tgtcttctaa agatttacaa     540
gttttagcta ttttcgaga  gatgaatgca ggaacagttt tagatccaca aatgataaaa     600
aatgaagatg tcagtgaaaa agagtatgca gcagtttctc agcaactttc caaattacca     660
ggtgttaaca cgtctatgga ttgggataga aaatatccat atggcgatac tttaagaggt     720
atattcggag atgtatcgac acctgctgaa ggtattccaa agaattgac  agaacattac     780 ttatccaaag gatattcacg caatgatcgt gttggaaaat cttacctaga atatcaatat     840
gaagatgtat tgcgtggtaa aagaaagaa atgaaataca caacggacaa atctggtaaa     900
gttacatctt cagaagtgtt aaatcctggc gctcgcggtc aagatttgaa attaacgatc     960
gatatagatc ttcaaaaaga agtagaagca ttattagata aacaaattaa gaagcttcgc    1020
agtcaaggtg ccaaagatat ggataatgca atgatggttg tacaaaatcc taaaaatgga    1080
gacattcttg cgcttgccgg aaagcagatt aataagagtg gtaaaatgac tgattatgac    1140
attggtacgt ttacttctca atttgcggtt ggatcttctg taaaaggtgg aacattatta    1200
gccggttatc agaataaagc tatcaaagtt ggagaaacaa tggtcgatga accattacat    1260
ttccaaggtg gtttgacaaa acgatcatac ttcaataaaa acgggcatgt aactattaat    1320
gataagcaag ctttgatgca ttcatcaaac gtatatatgt ttaaaacagc attaaaatta    1380
gcgggagacc ttattattc tggtatggct ttaccttcag acataagttc acctgcccaa    1440
aagctaagaa gaggattaaa tcaagtaggc ttaggtgtga aaacagggat agattttacca   1500 aatgaaacaa gaggtcaaat cgaaccatta acaataatc caggtaatta tctagattta    1560
tcaattggtc aatatgatac ctatacacca ttacaattat cacaatatgt ttcaactata    1620
gcgaatgatg gttatagaat acagccacac attggattaa cgattcatga atcaactaat    1680
aaagatgagg ttggtccact caagaagaaa attaatggca ctgtcttgaa caaggttaat    1740
aatactgaaa aggaaatcaa acaaattcaa gaaggattca aaatggcatt taatgataaa    1800
gatggtactg gatatgttag ttttaaagat acagtagtac ctactgctgg taaaacgggt    1860
accgcagaag tgttccaaaa cggagagcca agagttaact ctacttatat aggatacgcg    1920
ccaattgatg atccaaaatt agcgttttca attgtatata caaatcagcc tgtaccacca    1980
ccatggttaa caggtggaga cttaggtaga gatgtaatta actactactt taagcagtta    2040
ggtaaagatg ataaaaataa agacaaagac aaataa                             2076
```

<210> SEQ ID NO 110
<211> LENGTH: 2076
<212> TYPE: DNA
<213> ORGANISM: Staphylococcus aureus

<400> SEQUENCE: 110

```
ttgttaaaaa gactaaaaga aaaatcaaat gatgaaatcg ttcaaaatac aattaacaag      60
```

```
agaattaact ttatatttgg tgtgattata tttattttg cagtactagt actacgttta      120
ggttatttac aaatcgcaca aggctcacat tataaacaaa ttataaaaaa tgatgaaaac      180
attacagtga atgagtctgt gccaagaggt cgtattttag acagaaatgg gaaagtttta     240
gttgataatg cttctaaaat ggctattaca tatactaggg gtcgaaaaac aacacaatcg     300
gaaatgttgg atacggctga aaagttatca aagctaatca agatggatac taagaaaatt     360
acagaacgtg ataagaaaga tttctggatt cagttgcatc ctaaaaaagc aaaagcaatg     420
atgacaaaag aacaagctat gttagcagat ggaagtatta aacaagatca atatgataaa     480
caactgttat cgaaaatcgg aaaatcacaa ttagatgaat tgtcttctaa agatttacaa     540
gttttagcta ttttcgaga tgaatgca ggaacagttt tagatccaca aatgataaaa     600
aatgaagatg tcagtgaaaa agagtatgca gcagtttctc agcaactttc caaattacca     660
ggtgttaaca cgtctatgga ttgggataga aaatatccat atggcgatac tttaagaggt     720
atattcggag atgtatcgac acctgctgaa ggtattccaa aagaattgac agaacattac     780
ttatccaaag gatattcacg caatgatcgt gttggaaaat cttacctaga atatcaatat     840
gaagatgtat tgcgtggtaa gaagaaagaa atgaaataca caacgacaa atctggtaaa     900 gttacatctt cagaagtgtt aaatcctggc gctcgcggtc aagatttgaa attaacgatc     960
gatatagatc ttcaaaaaga agtagaagca ttattagata aacaaattaa gaagcttcgc    1020
agtcaaggtg ccaaagatat ggataatgca atgatggttg tacaaaatcc taaaaatgga    1080
gacattcttg cgcttgccgg aaagcagatt aataagagtg gtaaaatgac tgattatgac    1140
attggtacgt ttacttctca atttgcggtt ggatcttctg taaaaggtgg aacattatta    1200
gccggttatc agaataaagc tatcaaagtt ggagaaacaa tggtcgatga accattacat    1260
ttccaaggtg gtttgacaaa acgatcatac ttcaataaaa acgggcatgt aactattaat    1320
gataagcaag ctttgatgca ttcatcaaac gtatatatgt ttaaaacagc attaaaatta    1380
gcgggagacc cttattattc tggtatggct ttaccttcag acataagttc acctgcccaa    1440
aagctaagaa gaggattaaa tcaagtaggc ttaggtgtga aaacagggat agatttacca    1500
aatgaaacaa gaggtcaaat cgaaccatta acaaataatc caggtaatta tctagattta    1560
tcaattggtc aatatgatac ctatacacca ttacaattat cacaatatgt ttcaactata    1620
gcgaatgatg gttatagaat acagccacac attggattaa cgattcatga atcaactaat    1680
aaagatgagg ttggtccact caagaagaaa attaatggca ctgtcttgaa caaggttaat    1740
aatactgaaa aggaaatcaa acaaattcaa gaaggattca aaatggcatt taatgataaa    1800
gatggtactg gatatgttag ttttaaagat acagtagtac ctactgctgg taaaacgggt    1860
accgcagaag tgttccaaaa cggagagcca agagttaact ctacttatat aggatacgcg    1920
ccaattgatg atccaaaatt agcgttttca attgtatata caaatcagcc tgtaccacca    1980
ccatggttaa caggtggaga cttaggtaga gatgtaatta actactactt taagcagtta    2040
ggtaaaaatg ataaaaataa agacaaagac aaataa                              2076

<210> SEQ ID NO 111
<211> LENGTH: 44
<212> TYPE: DNA
<213> ORGANISM: Staphylococcus aureus

<400> SEQUENCE: 111
tttggtgtga ttgtatttat ttttgcagta ctagtactac gttt                      44
```

<210> SEQ ID NO 112
<211> LENGTH: 44
<212> TYPE: DNA
<213> ORGANISM: Staphylococcus aureus

<400> SEQUENCE: 112
tttggtgtga ttgtatttat ttttgcagta ctagtactac gttt                    44

<210> SEQ ID NO 113
<211> LENGTH: 44
<212> TYPE: DNA
<213> ORGANISM: Staphylococcus aureus

<400> SEQUENCE: 113
tttggtgtga ttgtatttat ttttgcagta ctagtactac gttt                    44

<210> SEQ ID NO 114
<211> LENGTH: 44
<212> TYPE: DNA
<213> ORGANISM: Staphylococcus aureus

<400> SEQUENCE: 114
tttggtgtga ttgtatttat ttttgcagta ctagtactac gttt                    44

<210> SEQ ID NO 115
<211> LENGTH: 44
<212> TYPE: DNA
<213> ORGANISM: Staphylococcus aureus

<400> SEQUENCE: 115
tttggtgtga ttgtatttat ttttgcagta ctagtactac gttt                    44

<210> SEQ ID NO 116
<211> LENGTH: 44
<212> TYPE: DNA
<213> ORGANISM: Staphylococcus aureus

<400> SEQUENCE: 116
tttggtgtga ttgtatttat ttttgcagta ctagtactac gttt                    44

<210> SEQ ID NO 117
<211> LENGTH: 44
<212> TYPE: DNA
<213> ORGANISM: Staphylococcus aureus

<400> SEQUENCE: 117
tttggtgtga ttatatttat ttttgcagta ctagtactac gttt                    44

<210> SEQ ID NO 118
<211> LENGTH: 44
<212> TYPE: DNA
<213> ORGANISM: Staphylococcus aureus

<400> SEQUENCE: 118
tttggtgtga ttgtatttat ttttgcagta ctagtactac gttt                    44

<210> SEQ ID NO 119
<211> LENGTH: 44
<212> TYPE: DNA
<213> ORGANISM: Staphylococcus aureus

<400> SEQUENCE: 119
tttggtgtga ttgtatttat ttttgcagta ctagtactac gttt                    44

<210> SEQ ID NO 120
<211> LENGTH: 44
<212> TYPE: DNA
<213> ORGANISM: Staphylococcus aureus

<400> SEQUENCE: 120
tttggtgtga ttgtatttat ttttgcagta ctagtactac gttt        44

<210> SEQ ID NO 121
<211> LENGTH: 44
<212> TYPE: DNA
<213> ORGANISM: Staphylococcus aureus

<400> SEQUENCE: 121
tttggtgtga ttgtatttat ttttgcagta ctagtactac gttt        44

<210> SEQ ID NO 122
<211> LENGTH: 36
<212> TYPE: DNA
<213> ORGANISM: Staphylococcus aureus

<400> SEQUENCE: 122
ggtaaagatg ataaaaataa agacaaagac aaataa              36

<210> SEQ ID NO 123
<211> LENGTH: 36
<212> TYPE: DNA
<213> ORGANISM: Staphylococcus aureus

<400> SEQUENCE: 123
ggtaaagatg ataaaaataa agacaaagac aaataa              36

<210> SEQ ID NO 124
<211> LENGTH: 36
<212> TYPE: DNA
<213> ORGANISM: Staphylococcus aureus

<400> SEQUENCE: 124
ggtaaagacg ataaaaataa agacaaagac aaataa              36

<210> SEQ ID NO 125
<211> LENGTH: 36
<212> TYPE: DNA
<213> ORGANISM: Staphylococcus aureus

<400> SEQUENCE: 125
ggtaaagatg ataaaaataa agacaaagac aaataa              36

<210> SEQ ID NO 126
<211> LENGTH: 36
<212> TYPE: DNA
<213> ORGANISM: Staphylococcus aureus

<400> SEQUENCE: 126
ggtaaagatg ataaaaataa agacaaagac aaataa              36

<210> SEQ ID NO 127
<211> LENGTH: 36
<212> TYPE: DNA
<213> ORGANISM: Staphylococcus aureus

<400> SEQUENCE: 127

```
ggtaaagatg ataaaaataa agacaaagac aaataa                               36

<210> SEQ ID NO 128
<211> LENGTH: 36
<212> TYPE: DNA
<213> ORGANISM: Staphylococcus aureus

<400> SEQUENCE: 128
ggtaaagatg ataaaaataa agacaaagac aaataa                               36

<210> SEQ ID NO 129
<211> LENGTH: 36
<212> TYPE: DNA
<213> ORGANISM: Staphylococcus aureus

<400> SEQUENCE: 129
ggtaaagatg ataaaaataa agacaaagac aaataa                               36

<210> SEQ ID NO 130
<211> LENGTH: 36
<212> TYPE: DNA
<213> ORGANISM: Staphylococcus aureus

<400> SEQUENCE: 130
ggtaaagatg ataaaaataa agacaaagac aaataa                               36

<210> SEQ ID NO 131
<211> LENGTH: 36
<212> TYPE: DNA
<213> ORGANISM: Staphylococcus aureus

<400> SEQUENCE: 131
ggtaaagatg ataaaaataa agacaaagac aaataa                               36

<210> SEQ ID NO 132
<211> LENGTH: 660
<212> TYPE: DNA
<213> ORGANISM: Staphylococcus epidermidis

<400> SEQUENCE: 132
ttgctaaaaa gattaaaaga aaaatcaaat gatgaaaaaa tgagaaacac catgaataaa     60
agaatcaatt tcatatttgg atttatagta tttatctttg ctatagtcgt attgagatta    120
ggttatttac aaatagcaca aggatctcat tacaaacaat taatcaaaaa cgatgaaaac    180
ataactgtta atgaatcagt accaagaggc cgaatactag atagaaatgg caaagtacta    240
gttgataatg cttcaaagat gtctattaca tacactagaa accgtaaaac atcacaaaag    300
gaaatgttaa atactgctaa gaaactgaca gatttaatta aaatggatac agataaaatt    360
actgagagag ataaaaagga tttttggatt caaatgtatc cgtcatctgc taaaaagtta    420
atgagaaaag aacaattaat gttagaggat ggcagtattt cacaagacca atttgatacc    480
caacttagag ataaaatagg aaaaaaacaa ttaaacagt taactaaaaa agatttgcaa     540
gttttagcaa tttatcggga aatgaacgct gggtcaactc tagatcctca aacaattaaa    600
aatgaagacg taagcgagaa agaatatgca gccgtatcac aacagctttc taaattacct    660
```